US009274101B2

(12) United States Patent
Bochner et al.

(10) Patent No.: US 9,274,101 B2
(45) Date of Patent: *Mar. 1, 2016

(54) METHODS AND KITS FOR OBTAINING A METABOLIC PROFILE OF LIVING ANIMAL CELLS

(75) Inventors: Barry Bochner, Alameda, CA (US); Larry Wiater, San Mateo, CA (US)

(73) Assignee: BIOLOG, Inc., Hayward, CA (US)

(*) Notice: Subject to any disclaimer, the term of this patent is extended or adjusted under 35 U.S.C. 154(b) by 1751 days.

This patent is subject to a terminal disclaimer.

(21) Appl. No.: 11/418,804

(22) Filed: May 5, 2006

(65) Prior Publication Data

US 2006/0286627 A1    Dec. 21, 2006

Related U.S. Application Data

(63) Continuation-in-part of application No. 11/192,161, filed on Jul. 27, 2005, now abandoned, which is a continuation of application No. 10/126,345, filed on Apr. 19, 2002, now abandoned.

(60) Provisional application No. 60/678,566, filed on May 5, 2005, provisional application No. 60/285,541, filed on Apr. 20, 2001.

(51) Int. Cl.
  *C12Q 1/02*  (2006.01)
  *G01N 33/50*  (2006.01)
  *C12N 5/07*  (2010.01)

(52) U.S. Cl.
  CPC .............. *G01N 33/5023* (2013.01); *C12N 5/06* (2013.01); *C12Q 1/025* (2013.01); *C12Q 2326/92* (2013.01)

(58) Field of Classification Search
  CPC .......... G01N 33/5023; G01N 33/5005; G01N 33/5004; C12N 5/06; C12Q 232/92; C12Q 1/0266; A01B 12/006
  See application file for complete search history.

(56) References Cited

U.S. PATENT DOCUMENTS

| | | | | |
|---|---|---|---|---|
| 4,129,483 A * | 12/1978 | Bochner | .......................... | 435/34 |
| 4,235,964 A * | 11/1980 | Bochner | .......................... | 435/34 |
| 4,241,186 A | 12/1980 | Roth | .............................. | 435/243 |
| 4,282,317 A | 8/1981 | Roth | .............................. | 435/253 |
| 4,326,052 A | 4/1982 | Kang et al. | ......................... | 536/1 |
| 4,326,053 A | 4/1982 | Kang et al. | ......................... | 536/1 |
| 5,134,063 A * | 7/1992 | Bochner | .......................... | 435/29 |
| 5,135,852 A | 8/1992 | Ebersole et al. | ................. | 435/39 |
| 5,571,723 A * | 11/1996 | Evans et al. | ...................... | 436/87 |
| 5,589,350 A | 12/1996 | Bochner | .......................... | 435/29 |
| 5,627,045 A | 5/1997 | Bochner et al. | ................. | 435/34 |
| 5,800,785 A | 9/1998 | Bochner | ....................... | 422/101 |
| 5,882,882 A | 3/1999 | Bochner et al. | ................. | 435/34 |
| 5,972,639 A | 10/1999 | Parandoosh | .................... | 435/29 |
| 5,989,853 A | 11/1999 | Bochner | .......................... | 435/34 |
| 6,046,021 A * | 4/2000 | Bochner | .......................... | 435/34 |
| 6,150,163 A | 11/2000 | McPherson et al. | .......... | 435/384 |
| 6,225,074 B1 | 5/2001 | Wright et al. | .................... | 435/15 |
| 6,271,022 B1 | 8/2001 | Bochner | ..................... | 435/287.3 |
| 6,387,651 B1 | 5/2002 | Bochner et al. | ................. | 435/34 |
| 6,414,121 B1 * | 7/2002 | Wood et al. | .................... | 530/350 |
| 6,436,631 B1 | 8/2002 | Bochner | .......................... | 435/4 |
| 6,436,660 B1 | 8/2002 | Little | .............................. | 435/32 |
| 6,573,063 B2 | 6/2003 | Hochman | ........................ | 435/29 |
| 6,686,173 B2 | 2/2004 | Bochner et al. | ................. | 435/34 |
| 6,727,076 B2 | 4/2004 | Bochner | .......................... | 435/34 |
| 6,869,931 B1 * | 3/2005 | McCrae | ........................ | 514/13.3 |
| 6,936,437 B2 * | 8/2005 | Gonzalez-Villasenor | ... | 435/69.1 |
| 2001/0039269 A1 * | 11/2001 | Peters et al. | .................. | 514/177 |
| 2002/0004458 A1 * | 1/2002 | Graham et al. | ............... | 504/320 |
| 2002/0123144 A1 * | 9/2002 | Helmstetter | ................... | 435/372 |
| 2002/0164574 A1 * | 11/2002 | Tanzer et al. | ..................... | 435/4 |
| 2006/0147512 A1 * | 7/2006 | Sabin | ............................ | 424/450 |

FOREIGN PATENT DOCUMENTS

| WO | WO 8002433 | 11/1980 | ............... C12Q 1/04 |
|---|---|---|---|
| WO | WO 9902650 | 1/1999 | ............... C12N 1/38 |

OTHER PUBLICATIONS

Burns et al. "Carbohydrate preferences of mammalian cells" J. Cell. Physiol. (1976) 88:307-316.*
Jonsson et al. "A new fluorometric assay for determination of osteoblastic proliferation: Effects of glucocorticoids and insulin-like growth factor-I" Calcif. Tissue Int. (1997) 60: 30-36.*
Bochner, B.R. Nature (1989) 339: 157-158.*
Bochner et al. Appl. Environ. Microbiol. (1977) 33: 434-444.*
Hollyer et al. Sexually Transmitted Diseases (1994) 21(5); 257-257.*
Alley et al., "Feasibility of drug screening with panels of human tumor cell lines using a microculture tetrazolium assay," *Cancer Res.*, 48:589-601 [1988].
American Public Health Association, *Standard Methods for the Examination of Water and Wastewater*, 16th ed., APHA, Washington, D.C., pp. 864-866 [1985].
Atlas in *Handbook of Microbiological Media*, CRC Press, Boca Raton, FL, p. 834 [1993].
Baughman et al., "Laboratory capacity to detect antimicrobial resistance, 1998," *MMWR*, 48:1167-1171 [2000].
Bianchi and Baneyx, "Stress responses as a tool to detect and characterize the mode of action of antimicrobial agents," *Appl. Environ. Microbiol.*, 65:5023-5027 [1999].
Black, *Microbiology: Principles and Applications*, 2nd ed., Prentice Hall, Englewood Cliffs, NJ, p. 153 [1993].
Bochner and Savageau, "Generalized indicator plate for genetic, metabolic, and taxonomic studies with microorganisms," *Appl. Environ. Microbiol.*, 33:434-444 [1977].
Bochner, "Sleuthing out bacterial identities," *Nature*, 339:157-158 [1989].

(Continued)

*Primary Examiner* — Susan Hanley
(74) *Attorney, Agent, or Firm* — Medlen & Carroll, LLP

(57) ABSTRACT

The present invention relates to growing and testing eukaryotic cells (e.g., animal or plant cells) in a multi-test format. In particular, the present invention provides methods and kits for obtaining a complex metabolic profile of animal cells. In addition, the present invention provides tools for assaying the effects of candidate compounds (e.g., hormones) on substrate utilization by mammalian cells.

31 Claims, 10 Drawing Sheets

(56) References Cited

OTHER PUBLICATIONS

Bochner, "'Breathprints' at the microbial level," *ASM News*, 55:536-539 [1990].

Braithwaite and Smith, in *Chromatographic Methods*, Chapman and Hall [eds.], London, pp. 24-50 [1985].

Butcher et al., "Organ specificity of lymphocyte migration: mediation by highly selective lymphocyte interaction with organ-specific determinants on high endothelial venules," *Eur. J. Immunol.*, 10:556-561 [1980].

Byth et al., "Assessment of a simple, non-toxic alamar blue cell survival assay to monitor tomato cell viability," *Phytochem. Anal.*, 12:340-346 [2001].

Collins et al., "Continuous growth and differentiation of human myeloid leukaemic cells in suspension culture," *Nature*, 270:347-349 [1977].

Cross, "Growth and Examination of Actinomycetes—Some Guidelines," in J. Holt et al., "The Actinomycetes," *Bergey's Manual® of Determinative Bacteriology*, 9th ed., Williams & Wilkins, Baltimore, pp. 605-609 [1994].

Dass et al., "Glutamine promotes colony formation in bone marrow and HL-60 cells; accelerates myeloid differentiation in induced HL-60 cells," In Vitro, 20:869-875 [1984].

DeRisi et al., "Exploring the metabolic and genetic control of gene expression on a genomic scale," *Science*, 278:680-686 [1997].

Garland, "Analysis and interpretation of community-level physiological profiles in microbial ecology," *FEMS Microbiol. Ecol.*, 24:289-300 [1997].

Glaser, "Functional genomics shifts drug discovery paradigm to protein expression and separation," *Genet. Engineer. News*, Sep. 15, at pp. 1 and 15 [1997].

Goffeau et al., "Life with 6000 genes," *Science*, 274:546-567 [1996].

Graan, et al., "Methyl purple, an exceptionally sensitive monitor of chloroplast photosystem I turnover: physical properties and synthesis," *Anal Biochem.*, 144:193-198 [1985].

Hansen et al., in *Healthcare Marketplace Guide Research Reports 2000*, 15th edition, vol. 1, Dorland's Biomedical, Philadelphia, PA 19102, pp. I-169 to I-172 [1999-2000].

Harch et al., "Using the Gini coefficient with BIOLOG substrate utilisation data to provide alternative quantitative measure for comparing bacterial soil communities," *J. Microbiol. Meth.*, 30:91-101 [1997].

Hindler "Antimicrobial Susceptibility Testing," in H.D. Isenberg (ed.), *Clinical Microbiology Procedures Handbook*, vol. 1, American Society for Microbiology, pp. 5.0.1-5.25.1, [1994].

Jonsson et al., "A new fluorometric assay for determination of osteoblastic proliferation: effects of glucocorticoids and insulin-like growth factor-I," *Calcif. Tissue Int.*, 60:30-36, [1997].

Jorgensen and Sahm, "Antimicrobial Susceptibility Testing: General Considerations," in Murray et al., (eds.) *Manual of Clinical Microbiology*, 6th edition, American Society for Microbiology, Washington, D.C., pp. 1277-1280 [1995].

Khurshid et al., "*Staphylococcus aureus* with reduced susceptibility to vancomycin—Illinois, 1999," *MMWR*, 48:1165-1167 [2000].

Knowles at al., "Human hepatocellular carcinoma cell lines secrete the major plasma proteins and hepatitis B surface antigen," *Science*, 209:497-499 [1980].

Marsili et al., "Small acidic peptides and peptidomimetic molecules: cell growth and differentiation," *Rivista di Biologia*, 93:175-182 [2000].

Moir et al., "Genomics and antimicrobial drug discovery," *Antimicrob. Agents Chemother.*, 43:439-446 [1999].

Mosmann, "Rapid calorimetric assay for cellular growth and survival: application to proliferation and cytotoxicity assays," *J. Immunol. Meth.*, 65:55-63 [1983].

Odani et al., "Enhancement by dimethyl sulfoxide of 1,25-dihydroxyvitamin D3-induced differentiation in human promyelocytic HL-60 leukemia cells requires dimethyl sulfoxide-induced G0/G1 arrest," *Res. Commun. Mol. Pathol. Pharmacol.*, 108:381-391 [2000].

Pennisi, "Laboratory workhorse decoded," *Science*, 277:1432-1434 [1997].

Reasoner and Geldreich, "A new medium for the enumeration and subculture of bacteria from potable water," *Appl. Environ. Microbiol.*, 49:1-7 [1985].

Sambrook et al., *Molecular Cloning: A Laboratory Manual*, 2nd ed., Cold Spring Harbor Laboratory Press, New York, pp. 16.8-16.15 [1989].

Shirling and Gottlieb, "Methods for Characterization of *Streptomyces* Species," *Intl. J. System. Bacterial.*, 16:313-330 [1966].

Smith et al., "Functional analysis of the genes of yeast chromosome V by genetic footprinting," *Science*, 274:2069-2074 [1997].

Trias and Gordon, "Innovative approaches to novel antibacterial drug discovery," *Curr. Opin. Biotechnol.*, 8:757-762 [1997].

Yamaguchi et al., "Bioassay of human granulocyte colony-stimulating factor using human promyelocytic HL-60 cells," *Biol. Pharm. Bull.*, 20:943-947 [1997].

Amersham Pharmacia Biotech, *Microcarrier Cell Culture*, edition AA pp. 115-121, [1999].

Antopol et al., "Studies of the metabolism of fibroblast cells in tissue culture utilizing neotetrazolium," *Transactions NY Academy Sciences*, 17:385-388 [1955].

Berry et al., "Production of reovirus type-1 and type-3 from Vero cells grown on solid macroporous microcarriers," *Biotechnol. Bioeng.*, 62:12-19 [1999].

Butler, "Growth limitations in microcarrier cultures," in *Advances in Biochemical Engineering/Biotechnology*, vol. 34, Springer-Verlag Berlin Heidelberg pp. 57-84 [1987].

Eagle et al., "The utilization of carbohydrates by human cell cultures," *J. Biol. Chem.*, 233:551-558 [1958].

Grohn et al., "Collagen-coated Ba2+-alginate microcarriers for the culture of anchorage-dependent mammalian cells," *BioTechniques*, 22:970-975 [1997].

Mather, "Laboratory scaleup of cell cultures (0.5-50 liters)," *Methods Cell Biol.*, 57:219-227 [1998].

Scudiero et al., "Evaluation of a soluble tetrazolium/formazan assay for cell growth and drug sensitivity in culture using human and other tumor cell lines," *Cancer Research*, 48:4827-4833 [1988].

Stanisz et al., "Comparative energy metabolism in cultured heart muscle and HeLa cells," *J. Cell. Physiol.*, 115:320-330 [1983].

van der Velden-de Groot, "Microcarrier technology, present status and perspective," *Cytotechnology*, 18:51-56 [1995].

Werner et al., "Cultivation of immortalized human hepatocytes HepZ on macroporous CultiSpher G microcarriers," *Biotechnol. Bioeng.*, 68:59-70 [2000].

Wice et al., "The continuous growth of vertebrate cells in the absence of sugar," *J. Biol. Chem.*, 256:7812-7819 [1981].

\* cited by examiner

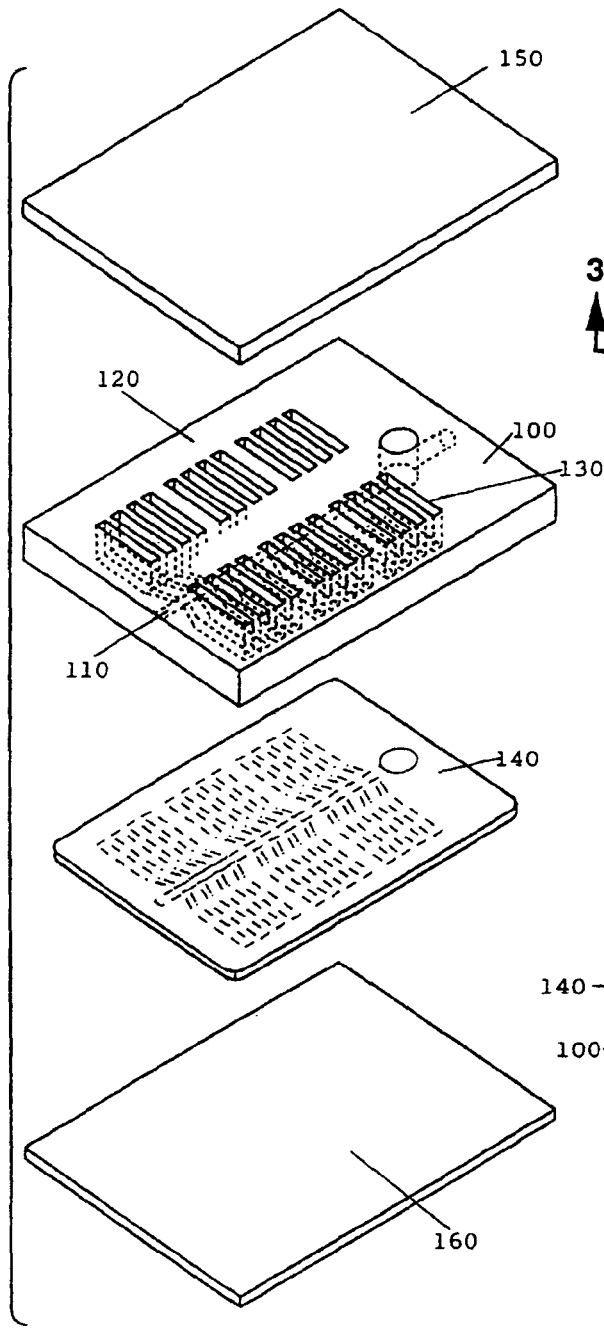
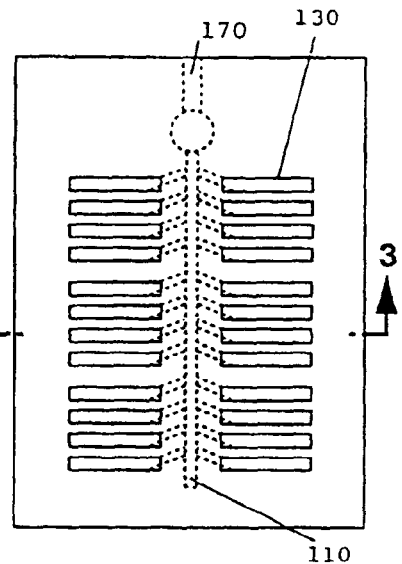
FIG. 2
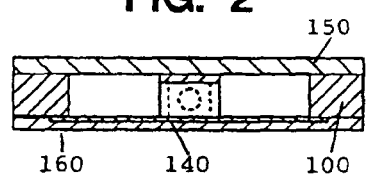
FIG. 3
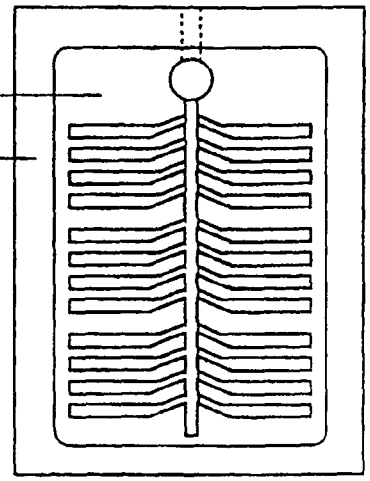
FIG. 4
FIG. 1

|  | phe 1 | phe 2 | phe 3 | phe 4 | phe 5 | phe 6 | phe 7 |
|---|---|---|---|---|---|---|---|
| NORMAL | + | + | + | + | + | + | + |
| MUTANT | − | + | + | + | + | + | + |
| NORMAL + DRUG 1 | − | + | + | + | + | + | + |
| NORMAL + DRUG 2 | − | + | + | + | − | + | + |

|  | phe 1 | phe 2 | phe 3 | phe 4 | phe 5 | phe 6 | phe 7 |
|---|---|---|---|---|---|---|---|
| NORMAL | + | + | + | + | + | + | + |
| MUTANT | − | + | + | + | + | + | + |
| NORMAL + DRUG 1 | − | + | + | + | + | + | + |
| NORMAL + DRUG 2 | + | + | + | + | − | + | + |
| NORMAL + DRUG 1 & 2 | − | + | + | + | − | − | − |

METHODS AND KITS FOR OBTAINING A METABOLIC PROFILE OF LIVING ANIMAL CELLS

This application claims the benefit of Provisional Application No. 60/678,566, filed on May 5, 2005, herein incorporated by reference. This application is also a Continuation-In-Part of U.S. application Ser. No 11/192,161, filed on Jul. 27, 2005, which is a Continuation of U.S. application Ser. No. 10/126,345, filed on Apr. 19, 2002, now abandoned, which claims benefit of Provisional Application No. 60/285,541, filed on Apr 20, 2001, all herein incorporated by reference in their entirety.

This invention was made in part with government support under grant number 9R44 MH074145-02, from the National Institutes of Health. As such, the United States government has certain rights in the invention.

FIELD OF THE INVENTION

The present invention relates to growing and testing eukaryotic cells (e.g., animal or plant cells) in a multi-test format. In particular, the present invention provides methods and kits for obtaining a complex metabolic profile of animal cells. In addition, the present invention provides tools for assaying the effects of candidate compounds (e.g., hormones) on substrate utilization by mammalian cells.

BACKGROUND OF THE INVENTION

In biological research, drug development research, and other areas of clinical, evolutionary, and basic research in microbiology and cellular biology, there remains a need for methods and compositions suitable for the characterization of cells, including but not limited to microbial cells, animal cells, and plant cells. Indeed, methods and compositions are needed for the characterization of cellular properties that may or may not change, depending upon genetic changes and changes in the intracellular and extracellular environment, including exposure of cells to biologically active chemicals.

In addition to the need for identification and characterization methods for microorganisms and other cells, there remains a need for pharmaceuticals for treatment of infectious, as well as non-infectious disease. Indeed, there is a need for methods and compositions to assess cellular phenotypes and the reaction of cells to the environment. Typically, the process of developing pharmaceuticals involves the steps of defining drug targets and testing potentially active chemicals to find the ones that specifically interact with the target to produce the desired effect without undesirable side effects. Although much work has been done in this area, there remains a need for improvements in the efficiency and effectiveness of the testing and evaluation of these chemicals.

In response to the pressures to generate more promising drug candidates, pharmaceutical and biotechnology companies have turned toward rapid, high-throughput methods to find and evaluate lead compounds. These lead compounds are typically selected by testing large libraries of compounds compiled from a wide variety of sources, using collections of extracts, chemicals synthesized by combinatorial chemistry approaches, or through rational drug design.

However, these methods have been a mixed blessing. Technologies such as combinatorial chemistry allow for rapid generation and testing (e.g., screening) of libraries of compounds against potential drug targets. Unfortunately, these technologies only look at the effect of the drugs on the proposed target, and they do not measure the effect on other cellular processes. A chemical may be an excellent candidate based on its interaction with the target protein, but it may also interact with other proteins in the cell and cause side effects. Thus, a major problem remains, in that the drug developer must sort through promising drug candidates to see how they effect other aspects of cell function, as well as how the drug candidates interact with other drugs that may be used simultaneously. Despite advances in these fields, there remains a need for highly sensitive and specific, yet cost-effective and easy-to-use methods for the identification and development of compounds (e.g., biologically active compounds) that are effective in the treatment of infectious and non-infectious diseases.

SUMMARY OF THE INVENTION

The present invention relates to growing and testing eukaryotic cells (e.g., animal or plant cells) in a multi-test format. In particular, the present invention provides methods and kits for obtaining a complex metabolic profile of animal cells. In addition, the present invention provides tools for assaying the effects of candidate compounds (e.g., hormones) on substrate utilization by mammalian cells.

Methods for obtaining a metabolic profile of animal cells are provided by the present invention. The methods comprise the steps of: providing a testing device comprising a plurality of testing wells and a plurality of testing substrates, wherein each of the testing wells contains at least one unique testing substrate of the plurality of testing substrates; suspending a sample comprising animal cells in a suspension medium to produce a suspension of animal cells, wherein the suspension medium is an aqueous solution comprising extraneous substrates; introducing the suspension of animal cells into the testing wells of the testing device; incubating the animal cells in the testing device under conditions suitable for depleting the suspension medium of extraneous substrates (pre-incubation or adaptation step); introducing a redox dye mix into the testing wells of the testing device; incubating the animal cells in the testing device under conditions suitable for color development upon utilization of at least one testing substrate by the animal cells (incubation step); and measuring the color development to obtain a metabolic profile of the animal cells. In some preferred embodiments, the plurality of testing substrates comprises at least 24 testing substrates, more preferably at least 48, 96, 192, or 384 testing substrates. In a subset of these embodiments, the plurality of testing substrates comprises but is not limited to three or more of glucose, mannose, fructose, D-galactose, D-ribose, D-xylose, L-arabinose, D-talose, D-psicose, trehalose, turanose, palatinose, cellobiose, melibiose, D-lactose, D-tagatose, sorbitol, arbutin, uridine, cytidine, inosine, 5'-uridine monophosphate, 2'-uridine monophosphate, 3'-uridine monophosphate, 5'-cytidine monophosphate, 5'-inosine monophosphate, 5'-xanthosine monophosphate, alpha-glycerolphosphate, pyruvate, succinate, lactate, L-alpha-aminobutyrate, L-arginine, L-glutamine, and L-glutamine diepeptides. In other embodiments, the plurality of testing substrates comprises but is not limited to three or more of alpha-Cyclodextrin, Sodium hexanoate, Dextrin, Tween 20, Glycogen (oyster), Tween 40, Maltitol, Tween 80, Maltotriose, Gelatin (porcine skin) Type A, D-(+)-Maltose monohydrate, Sodium 4-hydroxybenzoate, alpha-Trehalose Dihydrate, 4-Hydroxyphenylacetic acid, D-(+) Cellobiose, (±)-Octopamine, beta-Gentiobiose, 2-Phenylethylamine, L-Glucose, Tryptamine, D-(+)-Glucose, Tyramine, Cys-Gly, Phe-Ala, Gly-Cys, Phe-Asp, Gly-Ala, Phe-Glu, Gly-Arg, Phe-Gly, Gly-Asn, Phe-Ile, Gly-Asp, Phe-Met, Gly-Gly, Phe-Phe, Gly-His, Phe-Pro, Gly-Ile, Phe-Ser, Gly-Leu, Phe-Trp, Gly-Lys.HCl, Phe-Tyr, D-Glucose-6-phosphate, L-Alaninamide, alpha-D-Glucose 1-phosphate hydrate, L-Alanine, 3-O-Methyl-D-glucopyranose, D-Alanine, Methyl alpha-D-glucoside, L-Arginine, Methyl beta-D-glucoside, L-Asparagine, D-(−)-Salicin, L-Aspartic acid monohydrate, D-Sorbitol, D-Aspartic Acid, N-Acetyl-D-glucosaminitol, L-Glutamic acid hydrate, N-Acetyl-D-glucosamine, D-Glutamic Acid, D-(+)-Glucosamine, L-Glutamine, D-Glucosaminic acid, Glycine HCl, D-Gluconic acid, L-Histidine, Gly-Met, Phe-Val, Gly-Phe, Pro-Ala, Gly-Pro, Pro-Arg, Gly-Ser, Pro-Asn, Gly-Thr, Pro-Asp, Gly-Trp, Pro-Glu, Gly-Tyr, Pro-Gln, Gly-Val, Pro-Gly, His-Ala, Pro-Hyp, His-Asp, Pro-Ile, His-Glu, Pro-Leu, His-Gly, Pro-Lys, D-Glucuronic acid, L-Homoserine, Chondroitin 6-sulfate, trans-4-Hydroxy-L-Proline, Mannan, L-Isoleucine, D-Mannose, L-Leucine, Methyl alpha-D-Mannopyranoside, L-Lysine, D-Mannitol, L-Methionine, N-Acetyl-D-mannosamine, L-Ornithine HCL, D-(+)-Melezitose monohydrate, L-Phenylalanine, Sucrose, L-Proline, Palatinose, L-Serine, D-(+)-Turanose, D-Serine, D-Tagatose, L-Threonine, His-His, Pro-Phe, His-Leu, Pro-Pro, HCl, His-Lys.HBr, Pro-Ser, His-Met, Pro-Trp, His-Pro, Pro-Tyr, His-Ser, Pro-Val, His-Trp, Ser-Ala, His-Tyr, Ser-Asn, His-Val, Ser-Asp, Ile-Ala, Ser-Glu, Ile-Arg, Ser-Gln, Ile-Asn, Ser-Gly, L-(−)-Sorbose, D-Threonine, L-Rhamnose monohydrate, L-Tryptophan, L-Fucose, L-Tyrosine, D-Fucose, L-Valine, Fructose, Ala-Ala, D-Fructose 6-phosphate dihydrate, Ala-Arg, Stachyose, Ala-Asn, D-(+)-Raffinose pentahydrate, Ala-Asp, D-Lactitol monohydrate, Ala-Glu, Lactulose, Ala-Gln, Lactose monohydrate, Ala-Gly, Melibionic Acid, Ala-His, Ile-Gln, Ser-His, Ile-Gly, Ser-Leu, Ile-His, Ser-Met, Ile-Ile, Ser-Phe, Ile-Leu, Ser-Pro, Ile-Met, Ser-Ser, Ile-Phe, Ser-Tyr, Ile-Pro, Ser-Val, Ile-Ser, Thr-Ala, Ile-Trp, Thr-Arg, Ile-Tyr, Thr-Asp, Ile-Val, Thr-Glu, D-Melibiose, Ala-Ile, D-Galactose, Ala-Leu, Methyl alpha-D-galactopyranoside, Ala-Lys·HCl, Methyl-beta-D-galactopyranoside, Ala-Met, N-Acetyl-neuraminic acid, Ala-Phe, Pectin (apple), Ala-Pro, Sedoheptulose anhydride monohydrate, Ala-Ser, Thymidine, Ala-Thr, Uridine, Ala-Trp, Adenosine, Ala-Tyr, Inosine, Ala-Val, D-Ribose, Arg-Ala, Leu-Ala, Thr-Gln, Leu-Arg, Thr-Gly, Leu-Asn, Thr-Leu, Leu-Asp, Thr-Met, Leu-Glu, Thr-Phe, Leu-Gly, Thr-Pro, HCl, Leu-His, Thr-Ser, Leu-Ile, Trp-Ala, Leu-Leu, Trp-Arg·, Leu-Met, Trp-Asp, Leu-Phe, Trp-Glu, Leu-Pro.HCl, Trp-Gly, Ribitol, Arg-Arg, L-Arabinose, Arg-Asp, D-Arabinose, Arg-Gln, D-Xylose, Arg-Glu, Methyl beta-D-Xylopyranoside, Arg-Ile, Xylitol, Arg-Leu, myo-Inositol, Arg-Lys, meso-Erythritol, Arg-Met, Propylene glycol, Arg-Phe, Ethanolamine, Arg-Ser, Glycerol, Arg-Trp, rac-Glycerol 3-phosphate, Arg-Tyr, Leu-Ser, Trp-Leu, Leu-Trp, Trp-Lys, Leu-Tyr, Trp-Phe, Leu-Val, Trp-Ser, Lys-Ala, Trp-Trp, Lys-Arg, Trp-Tyr, Lys-Asp, Trp-Val, Lys-Glu, Tyr-Ala, Lys-Gly·HCl, Tyr-Gln, Lys-Ile, Tyr-Glu, Lys-Leu, Tyr-Gly, Lys-Lys·2 HCl, Tyr-His, Citric acid, Arg-Val, Tricarballylic Acid, Asn-Glu, Sodium DL-lactate 60% (w/w) Syrup, Asn-Val, Methyl D-lactate, Asp-Ala, Methyl pyruvate, Asp-Asp, Pyruvate, Asp-Glu, 2-oxoglutarate, Asp-Gln, Succinamic acid, Asp-Gly, succinate, Asp-Leu, mono-Methyl hydrogen succinate, Asp-Lys, L-(−)-Malic acid, Asp-Phe, D-(+)-Malic acid, Asp-Trp, Lys-Met, Tyr-Ile, Lys-Phe.HCl, Tyr-Leu, Lys-Pro, Tyr-Lys, Lys-Ser, Tyr-Phe, Lys-Thr, Tyr-Trp, Lys-Trp, Tyr-Tyr, Lys-Tyr, Tyr-Val, Lys-Val, Val-Ala, Met-Arg, Val-Arg, Met-Asp, Val-Asn, Met-Gln, Val-Asp, Met-Glu, Val-Glu, meso-Tartaric acid, Asp-Val, acetoacetate, Glu-Ala, gamma-Amino-N-butyric acid, Glu-Asp, Sodium 2-oxobutyrate, Glu-Glu, Sodium 2-hydroxybutyrate, Glu-Gly, DL-beta-Hydroxybutyric acid, Glu-Ser, 4-Hydroxybutyric acid, Glu-Trp, Sodium butyrate, Glu-Tyr, 2,3-Butanediol, Glu-Val, 3-Hydroxy 2-Butanone, Gln-Glu, Propionic acid, Gln-Gln, Sodium acetate, Gln-Gly, Met-Gly, Val-Gln, Met-His, Val-Gly, Met-Ile, Val-His, Met-Leu, Val-Ile, Met-Lys, Val-Leu·HCl, Met-Met, Val-Lys, Met-Phe, Val-Met, Met-Pro, HCl, Val-Phe, Met-Thr, Val-Pro, Met-Trp, Val-Ser, Met-Tyr, Val-Tyr, Met-Val, and Val-Val. In some preferred embodiments, the suspension of animal cells comprises 50,000 to 800,000 cells/ml, preferably 100,000 to 400,000 cells/ml. In some preferred embodiments, the suspension medium comprises vitamins, salts, and free amino acids, in the absence of D-glucose, sodium pyruvate, and phenol red, wherein the free amino acids are at a concentration of less than 1.2 mM (preferably about 0.3 mM). The present invention also provides embodiments in which the extraneous substrates are provided as a serum supplement to the suspension medium (e.g., 1-20% serum such as fetal, neonatal, calf, horse, etc). In a subset of these embodiments, the serum is dialyzed. In some preferred embodiments, the first incubating step (pre-incubation or adaptation step) comprises incubating the animal cells for a period of 12 to 60 hours (e.g., pre-incubation or adaptation period in the absence of the redox dye mix), preferably 24 to 48 hours, more preferably about 36 hours. In some preferred embodiments, the second incubating step (incubation step) comprises incubating the animal cells for a period of 0.5 to 36 hours (e.g., incubation period in the presence of the redox dye mix), preferably 6 to 24 hours.

Moreover, the present invention provides kits for obtaining a metabolic profile of animal cells. The kits comprise: a testing device comprising a plurality of testing wells and a plurality of testing substrates, wherein each of the testing wells contains at least one unique testing substrate; a redox dye mix; and instructions for suspending animal cells in a suspension medium to produce a suspension of animal cells, and for using the suspension with the testing device and the redox dye mix for testing responses of the animal cells to each of the plurality of testing substrates to obtain a metabolic profile of the animal cells. In some embodiments, the plurality of testing substrates comprises at least 24 testing substrates, more preferably at least 48, 96, 192, or 384 testing substrates. In some embodiments, the plurality of testing substrates comprises but is not limited to three or more of alpha-Cyclodextrin, Sodium hexanoate, Dextrin, Tween 20, Glycogen (oyster), Tween 40, Maltitol, Tween 80, Maltotriose, Gelatin (porcine skin) Type A, D-(+)-Maltose monohydrate, Sodium 4-hydroxybenzoate, alpha-Trehalose Dihydrate, 4-Hydroxyphenylacetic acid, D-(+) Cellobiose, (±)-Octopamine, beta-Gentiobiose, 2-Phenylethylamine, L-Glucose, Tryptamine, D-(+)-Glucose, Tyramine, Cys-Gly, Phe-Ala, Gly-Cys, Phe-Asp, Gly-Ala, Phe-Glu, Gly-Arg, Phe-Gly, Gly-Asn, Phe-Ile, Gly-Asp, Phe-Met, Gly-Gly, Phe-Phe, Gly-His, Phe-Pro, Gly-Ile, Phe-Ser, Gly-Leu, Phe-Trp, Gly-Lys.HCl, Phe-Tyr, D-Glucose-6-phosphate, L-Alaninamide, alpha-D-Glucose 1-phosphate hydrate, L-Alanine, 3-O-Methyl-D-glucopyranose, D-Alanine, Methyl alpha-D-glucoside, L-Arginine, Methyl beta-D-glucoside, L-Asparagine, D-(−)-Salicin, L-Aspartic acid monohydrate, D-Sorbitol, D-Aspartic Acid, N-Acetyl-D-glucosaminitol, L-Glutamic acid hydrate, N-Acetyl-D-glucosamine, D-Glutamic Acid, D-(+)-Glucosamine, L-Glutamine, D-Glucosaminic acid, Glycine HCl, D-Gluconic acid, L-Histidine, Gly-Met, Phe-Val, Gly-Phe, Pro-Ala, Gly-Pro, Pro-Arg, Gly-Ser, Pro-Asn, Gly-Thr, Pro-Asp, Gly-Trp, Pro-Glu, Gly-Tyr, Pro-Gln, Gly-Val, Pro-Gly, His-Ala, Pro-Hyp, His-Asp, Pro-Ile, His-Glu, Pro-Leu, His-Gly, Pro-Lys, D-Glucuronic acid, L-Homoserine, Chondroitin 6-sulfate, trans-4-Hydroxy-L-Proline, Mannan, L-Isoleucine, D-Mannose, L-Leucine, Methyl alpha-D-Mannopyranoside, L-Lysine, D-Mannitol, L-Methionine, N-Acetyl-D-mannosamine, L-Ornithine HCL, D-(+)-Melezitose monohydrate, L-Phenylalanine, Sucrose, L-Proline, Palatinose, L-Serine, D-(+)-Turanose, D-Serine, D-Tagatose, L-Threonine, His-His, Pro-Phe, His-Leu, Pro-Pro, HCl, His-Lys-HBr, Pro-Ser, His-Met, Pro-Trp, His-Pro, Pro-Tyr, His-Ser, Pro-Val, His-Trp, Ser-Ala, His-Tyr, Ser-Asn, His-Val, Ser-Asp, Ile-Ala, Ser-Glu, Ile-Arg, Ser-Gln, Ile-Asn, Ser-Gly, L-(−)-Sorbose, D-Threonine, L-Rhamnose monohydrate, L-Tryptophan, L-Fucose, L-Tyrosine, D-Fucose, L-Valine, Fructose, Ala-Ala, D-Fructose 6-phosphate dihydrate, Ala-Arg, Stachyose, Ala-Asn, D-(+)-Raffinose pentahydrate, Ala-Asp, D-Lactitol monohydrate, Ala-Glu, Lactulose, Ala-Gln, Lactose monohydrate, Ala-Gly, Melibionic Acid, Ala-His, Ile-Gln, Ser-His, Ile-Gly, Ser-Leu, Ile-His, Ser-Met, Ile-Ile, Ser-Phe, Ile-Leu, Ser-Pro, Ile-Met, Ser-Ser, Ile-Phe, Ser-Tyr, Ile-Pro, Ser-Val, Ile-Ser, Thr-Ala, Ile-Trp, Thr-Arg, Ile-Tyr, Thr-Asp, Ile-Val, Thr-Glu, D-Melibiose, Ala-Ile, D-Galactose, Ala-Leu, Methyl alpha-D-galactopyranoside, Ala-Lys.HCl, Methyl-beta-D-galactopyranoside, Ala-Met, N-Acetyl-neuraminic acid, Ala-Phe, Pectin (apple), Ala-Pro, Sedoheptulose anhydride monohydrate, Ala-Ser, Thymidine, Ala-Thr, Uridine, Ala-Trp, Adenosine, Ala-Tyr, Inosine, Ala-Val, D-Ribose, Arg-Ala, Leu-Ala, Thr-Gln, Leu-Arg, Thr-Gly, Leu-Asn, Thr-Leu, Leu-Asp, Thr-Met, Leu-Glu, Thr-Phe, Leu-Gly, Thr-Pro, HCl, Leu-His, Thr-Ser, Leu-Ile, Trp-Ala, Leu-Leu, Trp-Arg-, Leu-Met, Trp-Asp, Leu-Phe, Trp-Glu, Leu-Pro.HCl, Trp-Gly, Ribitol, Arg-Arg, L-Arabinose, Arg-Asp, D-Arabinose, Arg-Gln, D-Xylose, Arg-Glu, Methyl beta-D-Xylopyranoside, Arg-Ile, Xylitol, Arg-Leu, myo-Inositol, Arg-Lys, meso-Erythritol, Arg-Met, Propylene glycol, Arg-Phe, Ethanolamine, Arg-Ser, Glycerol, Arg-Trp, rac-Glycerol 3-phosphate, Arg-Tyr, Leu-Ser, Trp-Leu, Leu-Trp, Trp-Lys, Leu-Tyr, Trp-Phe, Leu-Val, Trp-Ser, Lys-Ala, Trp-Trp, Lys-Arg, Trp-Tyr, Lys-Asp, Trp-Val, Lys-Glu, Tyr-Ala, Lys-Gly.HCl, Tyr-Gln, Lys-Ile, Tyr-Glu, Lys-Leu, Tyr-Gly, Lys-Lys.2 HCl, Tyr-His, Citric acid, Arg-Val, Tricarballylic Acid, Asn-Glu, Sodium DL-lactate 60% (w/w) Syrup, Asn-Val, Methyl D-lactate, Asp-Ala, Methyl pyruvate, Asp-Asp, Pyruvate, Asp-Glu, 2-oxoglutarate, Asp-Gln, Succinamic acid, Asp-Gly, succinate, Asp-Leu, mono-Methyl hydrogen succinate, Asp-Lys, L-(−)-Malic acid, Asp-Phe, D-(+)-Malic acid, Asp-Trp, Lys-Met, Tyr-Ile, Lys-Phe.HCl, Tyr-Leu, Lys-Pro, Tyr-Lys, Lys-Ser, Tyr-Phe, Lys-Thr, Tyr-Trp, Lys-Trp, Tyr-Tyr, Lys-Tyr, Tyr-Val, Lys-Val, Val-Ala, Met-Arg, Val-Arg, Met-Asp, Val-Asn, Met-Gln, Val-Asp, Met-Glu, Val-Glu, meso-Tartaric acid, Asp-Val, acetoacetate, Glu-Ala, gamma-Amino-N-butyric acid, Glu-Asp, Sodium 2-oxobutyrate, Glu-Glu, Sodium 2-hydroxybutyrate, Glu-Gly, DL-beta-Hydroxybutyric acid, Glu-Ser, 4-Hydroxybutyric acid, Glu-Trp, Sodium butyrate, Glu-Tyr, 2,3-Butanediol, Glu-Val, 3-Hydroxy 2-Butanone, Gln-Glu, Propionic acid, Gln-Gln, Sodium acetate, Gln-Gly, Met-Gly, Val-Gln, Met-His, Val-Gly, Met-Ile, Val-His, Met-Leu, Val-Ile, Met-Lys, Val-Leu.HCl, Met-Met, Val-Lys, Met-Phe, Val-Met, Met-Pro, HCl, Val-Phe, Met-Thr, Val-Pro, Met-Trp, Val-Ser, Met-Tyr, Val-Tyr, Met-Val, and Val-Val. In some embodiments, the kits comprise an aqueous suspension medium comprising vitamins, salts, and free amino acids, in the absence of D-glucose, sodium pyruvate, and phenol red, wherein the free amino acids are at a concentration of less than 1.2 mM (preferably less than 0.3 mM).

In addition, the present invention provides methods for obtaining a multiplexed metabolic profile of animal cells. The methods comprise the steps of: providing a testing device comprising a plurality of testing wells and a plurality of testing substrates, wherein each of the testing wells contains at least one unique testing substrate; suspending multiple samples comprising animal cells in multiple suspension media to produce multiple suspensions, wherein the multiple suspension media comprise three or more of a low serum medium, an intermediate serum medium, a high serum medium, a whole serum medium, a dialyzed serum medium, an amino acid-rich medium, an amino acid poor-medium, or a combination thereof; introducing the multiple suspensions of animal cells into the testing wells of the testing device; incubating the animal cells in the testing device under conditions suitable for depleting the suspension medium of extraneous substrates; introducing a redox dye mix into the testing wells of the testing device; incubating the animal cells in the testing device under conditions suitable for color development upon utilization of at least one testing substrate by the animal cells; and measuring the color development to obtain a multiplexed metabolic profile of the animal cells, comprising multiple metabolic profiles (three or more of a low serum [1-5%] metabolic profile, an intermediate serum [6-10%] metabolic profile, a high serum [11-25%] metabolic profile, a whole serum metabolic profile, a dialyzed serum metabolic profile, an amino acid-rich metabolic profile [0.3 mM or more], and an amino acid-poor [less than 0.1 mM] metabolic profile).

Furthermore, the present invention provides methods for observing effects of a candidate compound on substrate utilization by animal cells, comprising the steps of: providing a testing device comprising a plurality of testing wells containing a range of concentrations of a testing substrate and a range of concentrations of a candidate compound (e.g., cross-titration); suspending a sample comprising animal cells in a suspension medium to produce a suspension of animal cells, wherein the suspension medium is an aqueous solution comprising extraneous substrates; introducing the suspension of animal cells into the testing wells of the testing device; incubating the animal cells in the testing device under conditions suitable for depleting the suspension medium of the extraneous substrates (e.g., pre-incubation or adaptation period); introducing a redox dye mix into the testing wells of the testing device; incubating the animal cells in the testing device under conditions suitable for color development upon utilization of the testing substrate by the animal cells; and measuring the color development to obtain a metabolic profile of the animal cells. In preferred embodiments, the range of concentrations of the testing substrate comprises a low end, a middle, and a high end, wherein the low end comprises a concentration of testing substrate that is wholly depleted, the middle comprises a concentration of testing substrate this is partially depleted, and the high end comprises a concentration of testing substrate that is not depleted, prior to introduction of the redox dye mix at completion of the pre-incubation or adaptation period. In a subset of the embodiments, the low end of the range is between 0.025 and 0.5 mM (preferably about 0.25 mM) and the high end of the range is between 2.5 and 50 mM (preferably 2.5 mM). Some methods of the present invention further comprise determining that the candidate compound increases substrate utilization by the animal cells when color development is observed to decrease with increasing concentrations of the candidate compound (preferably when color development is also observed to increase with increasing concentrations of the testing substrate and/or when animal cell toxicity is not observed to increase with increasing concentrations of the candidate compound, as determined by methods known in the art). Other methods of the present invention further comprise determining that the candidate compound decreases substrate utilization by the animal cells when color development is observed to increase with increasing concentrations of the candidate compound. In preferred embodiments, the testing substrate comprises a carbon source such as glucose, and the candidate compound comprises a hormone such as insulin (other preferred candidate compounds comprise receptor agonists and receptor antagonists).

In one preferred embodiment of the kits, the testing substrates are selected from the group consisting of carbon sources, nitrogen sources, sulfur sources, phosphorus sources, amino peptidase substrates, carboxy peptidase substrates, oxidizing agents, reducing agents, mutagens, amino acid analogs, sugar analogs, nucleoside analogs, base analogs, dyes, detergents, toxic metals, inorganics, and drugs (e.g., antimicrobials). Indeed, it is not intended that the present invention be limited to any particular testing substrates, as it is contemplated that any testing substrate suitable for use with the present invention will be utilized. In some particularly preferred embodiments, the testing device further comprises a colorimetric indicator selected from the group consisting of chromogenic substrates, oxidation-reduction indicators, and pH indicators. In alternate preferred embodiments, the oxidation-reduction indicator is tetrazolium violet, while in other embodiments the oxidation-reduction indicator is redox purple. In yet other preferred embodiments, the testing device is at least one micro titer plate (e.g., MICROPLATE testing plates), while in other preferred embodiments the testing device is a miniaturized test plate or card (e.g., MICROCARD miniaturized testing cards). In still other embodiments, the response is a kinetic response.

The present invention also provides methods for comparing at least two cell preparations, comprising the steps of: providing a testing device comprising a plurality of testing wells, wherein the wells contain at least one test substrate selected from the group consisting of nitrogen sources, phosphorus sources, sulfur sources, and auxotrophic supplements; preparing a first suspension comprising a first cell preparation in an aqueous solution, and a second suspension comprising a second cell preparation in an aqueous solution; introducing the first and second suspensions into the wells of the testing device; detecting the response of the first and second cell preparations to the testing substrate; and comparing the response of the first and second cell preparations. In some embodiments of these methods, the first and second cell preparations comprise microorganisms selected from the group consisting of bacteria and fungi. In still other embodiments, the first and second cell preparations contain cells of the same genus and species, while in other embodiments, the first and second cell preparations contain cells that differ in one or more genes. In further embodiments, the first and second cell preparations are animal or plant cells.

The present invention provides methods for testing the response of a cell to at least one biologically active chemical comprising the steps of: a) providing a testing device having at least two wells, wherein each well of the testing device contains at least one substrate selected from the group consisting of carbon sources, nitrogen sources, phosphorus sources, sulfur sources, growth stimulating nutrients, drugs (e.g., antimicrobials), and chromogenic testing substrates; and a suspension comprising at least one cell and at least one biologically active chemical; b) inoculating the suspension into the wells of the testing device; and c) observing the response of the cell to the biologically active chemical(s). In some embodiments, the testing device is selected from the group consisting of microtiter plates and microtiter cards. In other embodiments, the suspension further comprises a gelling agent. In still other embodiments, the testing device further comprises a gel-initiating agent in the wells. In some preferred embodiments, the suspension further comprises a calorimetric indicator, while in other preferred embodiments the testing device further comprises a colorimetric indicator in the wells. In further embodiments, the observing is visual, while in other particularly preferred embodiments the observing is performed by an instrument.

For example, in some embodiments the present invention provides methods for testing animal or plant cells, comprising providing a testing device comprising a plurality of testing wells, wherein the testing wells of the testing device contain at least one testing substrate selected from the group consisting of carbon sources, nitrogen sources, phosphorus sources, sulfur sources, biologically active chemicals, and chromogenic compounds; preparing a suspension comprising a pure culture of cells in a suspension medium; introducing the suspension into the wells of the testing device; and observing at least one response of the cells to the testing substrate. In some embodiments, the testing device is selected from the group including, but not limited to a MICROPLATE and a MICROCARD.

The present invention is not limited to a particular carbon source. A variety of carbon source are contemplated including, but not limited to: D-Trehalose, D-Mannose, Dulcitol, L-Arabinose, N-Acetyl-D-Glucosamine, D-Saccharic Acid, Succinic Acid, D-Galactose, L-Aspartic Acid, L-Proline, D-Alanine, D-Serine, Formic Acid, D-Mannitol, L-Glutamic Acid, D-Sorbitol, Glycerol, L-Fucose, D-Glucuronic Acid, D-Gluconic Acid, D,L-α-Glycerol-Phosphate, D-Xylose, L-Lactic Acid, D-Glucose-6-Phosphate, Maltose, D-Melibiose, Thymidine, D-Galactonic Acid-γ-Lactone, D,L-Malic Acid, D-Ribose, Tween 20, L-Rhamnose, D-Fructose, Acetic Acid, α-D-Glucose, L-Asparagine, Lactulose, Sucrose, Uridine, D-Aspartic Acid, D-Glucosaminic Acid, 1,2-Propanediol, Tween 40, α-Keto-Glutaric Acid, α-Keto-Butyric Acid, α-Methyl-D-Galactoside, α-D-Lactose, L-Glutamine, Maltotriose, 2'-Deoxy Adenosine, Adenosine, m-Tartaric Acid, D-Glucose-1-Phosphate, D-Fructose-6-Phosphate, Tween 80, α-Hydroxy Glutaric Acid-γ-Lactone, α-Hydroxy Butyric Acid, β-Methyl-D-Glucoside, Adonitol, Glycyl-L-Aspartic Acid, Glyoxylic Acid, D-Cellobiose, Inosine, Citric Acid, m-Inositol, D-Threonine, Fumaric Acid, Bromo Succinic Acid, Propionic Acid, Mucic Acid, Glycolic Acid, Glycyl-L-Glutamic Acid, Methyl Pyruvate, D-Malic Acid, L-Malic Acid, Tricarballylic Acid, L-Serine, L-Threonine, L-Alanine, L-Alanyl-Glycine, Acetoacetic Acid, N-Acetyl-β-D-Mannosamine, Mono Methyl Succinate, Glycyl-L-Proline, D-Galacturonic Acid, Phenylethylamine, 2-Aminoethanol, p-Hydroxy Phenyl Acetic Acid, M-Hydroxy Phenyl Acetic Acid, Tyramine, D-Psicose, L-Lyxose, Glucuronamide, Pyruvic Acid, L-Galactonic Acid-γ-Lactone, Laminarin, Mannan, Pectin, Chondroitin Sulfate C, α-Cyclodextrin, β-Cyclodextrin, γ-Cyclodextrin, Dextrin, Gelatin, Glycogen, Inulin, N-Acetyl-D-Galactosamine, i-Erythritol, D-Fucose, 3-0-β-D-Galacto-pyranosyl-D-Arabinose, N-Acetyl-Neuraminic Acid, β-D-Allose, Amygdalin, D-Arabinose, D-Arabitol, L-Arabitol, Arbutin, 2-Deoxy-D-Ribose, Gentiobiose, α-Methyl-D-Mannoside, β-Methyl-D-Xyloside, Palatinose, L-Glucose, Lactitol, D-Lyxose, Maltitol, α-Methyl-D-Galactoside, β-Methyl-D-Galactoside, 3-Methyl Glucose, β-Methyl-D-Glucuronic Acid, D-Raffinose, γ-Amino Butyric Acid, δ-Amino Valeric Acid, Butyric Acid, Salicin, Sedoheptulosan, L-Sorbose, Stachyose, D-Tagatose, Turanose, Xylitol, L-Xylose, Capric Acid, β-Hydroxy Pyruvic Acid, Itaconic Acid, 5-Keto-D-Gluconic Acid, Caproic Acid, Citraconic Acid, Citramalic Acid, Dihydroxy Fumaric Acid, 2-Hydroxy Benzoic Acid, 4-Hydroxy Benzoic Acid, β-Hydroxy Butyric Acid, γ-Hydroxy Butyric Acid, D-Lactic Acid Methyl Ester, Succinarnic Acid, D-Tartaric Acid, L-Tartaric Acid, Malonic Acid, Melibionic Acid, Oxalic Acid, Oxalomalic Acid, Quinic Acid, D-Ribono-1,4-Lactone, Sebacic Acid, Sorbic Acid, Acetamide, L-Leucine, L-Lysine, L-Methionine, L-Alaninamide, N-Acetyl-L-Glutamic Acid, L-Arginine, Glycine, L-Histidine, L-Homoserine, Hydroxy-L-Proline, L-Isoleucine, L-Ornithine, 2,3-Butanediol, 2,3-Butanone, 3-Hydroxy 2-Butanone, L-Phenylalanine, L-Pyroglutamic Acid, L-Valine, D,L-Carnitine, Sec-Butylamine, D,L-Octopamine, Putrescine, Dihydroxy Acetone, Ala-Lys, Ala-Phe, Ala-Pro, Ala-Ala, Ala-Arg, Ala-Asn, Ala-Glu, Ala-Gly, Ala-His, Ala-Leu, Ala-Ser, Arg-Ile, Arg-Leu, Arg-Lys, Ala-Thr, Ala-Trp, Ala-Tyr, Arg-Ala, Arg-Arg, Arg-Asp, Arg-Gln, Arg-Glu, Arg-Met, Asp-Glu, Asp-Leu, Asp-Lys, Arg-Phe, Arg-Ser, Arg-Trp, Arg-Tyr, Arg-Val, Asn-Glu, Asn-Val, Asp-Asp, Asp-Phe, Glu-Ser, Glu-Trp, Glu-Tyr, Asp-Trp, Asp-Val, Cys-Gly, Gln-Gln, Gln-Gly, Glu-Asp, Glu-Glu, Glu-Gly, Glu-Val, Gly-Phe, Gly-Pro, Gly-Ser, Gly-Ala, Gly-Arg, Gly-Cys, Gly-Gly, Gly-His, Gly-Leu, Gly-Lys, Gly-Met, Gly-Thr, His-Pro, His-Ser, His-Trp, Gly-Trp, Gly-Tyr, Gly-Val, His-Asp, His-Gly, His-Leu, His-Lys, His-Met, His-Tyr, Ile-Phe, Ile-Pro, Ile-Ser, His-Val, Ile-Ala, Ile-Arg, Ile-Gln, Ile-Gly, Ile-His, Ile-Ile, Ile-Met, Ile-Trp, Leu-Leu, Leu-Met, Leu-Phe, Ile-Tyr, Ile-Val, Leu-Ala, Leu-Arg, Leu-Asp, Leu-Glu, Leu-Gly, Leu-Ile, Lys-Leu, Lys-Lys, Lys-Phe, Leu-Ser, Leu-Trp, Leu-Val, Lys-Ala, Lys-Arg, Lys-Glu, Lys-Ile, Lys-Pro, Met-Glu, Met-Gly, Met-His, Lys-Ser, Lys-Thr, Lys-Trp, Lys-Tyr, Lys-Val, Met-Arg, Met-Asp, Met-Gln, Met-Ile, Phe-Gly, Phe-Ile, Phe-Phe, Met-Leu, Met-Lys, Met-Met, Met-Phe, Met-Pro, Met-Trp, Met-Val, Phe-Ala, Phe-Pro, Pro-Phe, Pro-Pro, Pro-Tyr, Phe-Ser, Phe-Trp, Pro-Ala, Pro-Asp, Pro-Gln, Pro-Gly, Pro-Hyp, Pro-Leu, Ser-Ala, Ser-Val, Thr-Ala, Thr-Arg, Ser-Gly, Ser-His, Ser-Leu, Ser-Met, Ser-Phe, Ser-Pro, Ser-Ser, Ser-Tyr, Thr-Glu, Trp-Gly, Trp-Leu, Trp-Lys, Thr-Gly, Thr-Leu, Thr-Met, Thr-Pro, Trp-Ala, Trp-Arg, Trp-Asp, Trp-Glu, Trp-Phe, Tyr-Leu, Tyr-Lys, Tyr-Phe, Trp-Ser, Trp-Trp, Trp-Tyr, Tyr-Ala, Tyr-Gln, Tyr-Glu, Tyr-Gly, Tyr-His, Tyr-Trp, Val-Tyr, Val-Val, γ-Glu-Gly, Tyr-Tyr, Val-Arg, Val-Asn, Val-Asp, Val-Gly, Val-His, Val-Ile, Val-Leu, Asp-Gly, Glu-Ala, Gly-Asn, Ala-Asp, Ala-Gln, Ala-lle, Ala-Met, Ala-Val, Asp-Ala, Asp-Gln, Gly-Asp, Leu-Pro, Leu-Tyr, Lys-Asp, Gly-lle, His-Ala, His-Glu, His-His, Ile-Asn, Ile-Leu, Leu-Asn, Leu-His, Lys-Gly, Phe-Val, Pro-Arg, Pro-Asn, Lys-Met, Met-Thr, Met-Tyr, Phe-Asp, Phe-Glu, Gln-Glu, Phe-Met, Phe-Tyr, Pro-Glu, Ser-Glu, Thr-Asp, Thr-Gln, Pro-lle, Pro-Lys, Pro-Ser, Pro-Trp, Pro-Val, Ser-Asn, Ser-Asp, Ser-Gln, Thr-Phe, Val-Met, Val-Phe, Val-Pro, Thr-Ser, Trp-Val, Tyr-lle, Tyr-Val, Val-Ala, Val-Gln, Val-Glu, Val-Lys, Val-Ser, D-Leu-D-Leu, D-Leu-Gly, D-Leu-Tyr, β-Ala-Ala, β-Ala-Gly, β-Ala-His, Met-β-Ala,β-Ala-Phe, D-Ala-D-Ala, D-Ala-Gly, D-Ala-Leu, γ-Glu-Gly, Phe-β-Ala, Ala-Ala-Ala, D-Ala-Gly-Gly, γ-D-Glu-Gly, Gly-D-Ala, Gly-D-Asp, Gly-D-Ser, Gly-D-Thr, Gly-D-Val, Leu-β-Ala, Leu-D-Leu, Gly-Gly-Ala, Leu-Leu-Leu, Phe-Gly-Gly, Tyr-Gly-Gly, Gly-Gly-D-Leu, Gly-Gly-Gly, Gly-Gly-lle, Gly-Gly-Leu, Gly-Gly-Phe, Val-Tyr-Val, Gly-Phe-Phe, and Leu-Gly-Gly.

The present invention is not limited to a particular nitrogen source. A variety of nitrogen sources are contemplated including, but not limited to: L-Aspartic Acid, L-Cysteine, L-Glutamic Acid, Ammonia, Nitrite, Nitrate, Urea, Biuret, L-Alanine, L-Arginine, L-Asparagine, L-Glutamine, L-Serine, L-Threonine, L-Tryptophan, Glycine, L-Histidine, L-Isoleucine, L-Leucine, L-Lysine, L-Methionine, L-Phenylalanine, L-Proline, L-Tyrosine, L-Citrulline, L-Homoserine, L-Ornithine, L-Valine, D-Alanine, D-Asparagine, D-Aspartic Acid, D-Glutamic Acid, D-Lysine, D-Serine, D-Valine, N-Acetyl-D,L-Glutamic Acid, Ethylenediamine, Putrescine, Agmatine, N-Phthaloyl-L-Glutamic Acid, L-Pyroglutamic Acid, Hydroxylamine, Methylamine, N-Amylamine, N-Butylamine, Ethylamine, Ethanolamine, Histamine, D-Mannosamine, N-Acetyl-D-Glucosamine, N-Acetyl-D-Galactosamine, β-Phenylethylamine, Tyramine, Acetamide, Formamide, Glucuronamide, D,L-Lactamide, D-Glucosamine, D-Galactosamine, N-Acetyl-D-Mannosamine, Uracil, Uridine, Inosine, Adenine, Adenosine, Cytidine, Cytosine, Guanine, Guanosine, Thymine, Thymidine, Xanthine, D,L-α-Amino-Caprylic Acid, δ-Amino-N-Valeric Acid, α-Amino-N-Valeric Acid, Xanthosine, Uric Acid, Alloxan, Allantoin, Parabanic Acid, D,L-α-Amino-N-Butyric Acid, γ-Amino-N-Butyric Acid, ε-Amino-N-Caproic Acid, Ala-Asp, Gly-Glu, Gly-Met, Met-Ala, Ala-Gln, Ala-Glu, Ala-Gly, Ala-His, Ala-Leu, Ala-Thr, Gly-Asn, Gly-Gln, Ala-Lys, Ala-Phe, Ala-Pro, Ala-Ala, Ala-Arg, Ala-Asn, Ala-Glu, Ala-Gly, Ala-His, Ala-Leu, Ala-Ser, Arg-Ile, Arg-Leu, Arg-Lys, Ala-Thr, Ala-Trp, Ala-Tyr, Arg-Ala, Arg-Arg, Arg-Asp, Arg-Gin, Arg-Glu, Arg-Met, Asp-Glu, Asp-Leu, Asp-Lys, Arg-Phe, Arg-Ser, Arg-Trp, Arg-Tyr, Arg-Val, Asn-Glu, Asn-Val, Asp-Asp, Asp-Phe, Glu-Ser, Glu-Trp, Glu-Tyr, Asp-Trp, Asp-Val, Cys-Gly, Gln-Gln, Gln-Gly, Glu-Asp, Glu-Glu, Glu-Gly, Glu-Val, Gly-Phe, Gly-Pro, Gly-Ser, Gly-Ala, Gly-Arg, Gly-Cys, Gly-Gly, Gly-His, Gly-Leu, Gly-Lys, Gly-Met, Gly-Thr, His-Pro, His-Ser, His-Trp, Gly-Trp, Gly-Tyr, Gly-Val, His-Asp, His-Gly, His-Leu, His-Lys, His-Met, His-Tyr, Ile-Phe, Ile-Pro, Ile-Ser, His-Val, Ile-Ala, Ile-Arg, Ile-Gln, Ile-Gly, Ile-His, Ile-Ile, Ile-Met, Ile-Trp, Leu-Leu, Leu-Met, Leu-Phe, Ile-Tyr, Ile-Val, Leu-Ala, Leu-Arg, Leu-Asp, Leu-Glu, Leu-Gly, Leu-Ile, Lys-Leu, Lys-Lys, Lys-Phe, Leu-Ser, Leu-Trp, Leu-Val, Lys-Ala, Lys-Arg, Lys-Glu, Lys-Ile, Lys-Pro, Met-Glu, Met-Gly, Met-His, Lys-Ser, Lys-Thr, Lys-Trp, Lys-Tyr, Lys-Val, Met-Arg, Met-Asp, Met-Gln, Met-Ile, Phe-Gly, Phe-Ile, Phe-Phe, Met-Leu, Met-Lys, Met-Met, Met-Phe, Met-Pro, Met-Trp, Met-Val, Phe-Ala, Phe-Pro, Pro-Phe, Pro-Pro, Pro-Tyr, Phe-Ser, Phe-Trp, Pro-Ala, Pro-Asp, Pro-Gln, Pro-Gly, Pro-Hyp, Pro-Leu, Ser-Ala, Ser-Val, Thr-Ala, Thr-Arg, Ser-Gly, Ser-His, Ser-Leu, Ser-Met, Ser-Phe, Ser-Pro, Ser-Ser, Ser-Tyr, Thr-Glu, Trp-Gly, Trp-Leu, Trp-Lys, Thr-Gly, Thr-Leu, Thr-Met, Thr-Pro, Trp-Ala, Trp-Arg, Trp-Asp, Trp-Glu, Trp-Phe, Tyr-Leu, Tyr-Lys, Tyr-Phe, Trp-Ser, Trp-Trp, Trp-Tyr, Tyr-Ala, Tyr-Gln, Tyr-Glu, Tyr-Gly, Tyr-His, Tyr-Trp, Val-Tyr, Val-Val, γ-Glu-Gly, Tyr-Tyr, Val-Arg, Val-Asn, Val-Asp, Val-Gly, Val-His, Val-Ile, Val-Leu, Asp-Gly, Glu-Ala, Gly-Asn, Ala-Asp, Ala-Gln, Ala-lle, Ala-Met, Ala-Val, Asp-Ala, Asp-Gln, Gly-Asp, Leu-Pro, Leu-Tyr, Lys-Asp, Gly-lle, His-Ala, His-Glu, His-His, Ile-Asn, Ile-Leu, Leu-Asn, Leu-His, Lys-Gly, Phe-Val, Pro-Arg, Pro-Asn, Lys-Met, Met-Thr, Met-Tyr, Phe-Asp, Phe-Glu, Gln-Glu, Phe-Met, Phe-Tyr, Pro-Glu, Ser-Glu, Thr-Asp, Thr-Gln, Pro-Ile, Pro-Lys, Pro-Ser, Pro-Trp, Pro-Val, Ser-Asn, Ser-Asp, Ser-Gln, Thr-Phe, Val-Met, Val-Phe, Val-Pro, Thr-Ser, Trp-Val, Tyr-lle, Tyr-Val, Val-Ala, Val-Gln, Val-Glu, Val-Lys, Val-Ser, D-Leu-D-Leu, D-Leu-Gly, D-Leu-Tyr, β-Ala-Ala, β-Ala-Gly, β-Ala-His, Met-β-Ala, β-Ala-Phe, D-Ala-D-Ala, D-Ala-Gly, D-Ala-Leu, γ-Glu-Gly, Phe-β-Ala, Ala-Ala-Ala, D-Ala-Gly-Gly, γ-D-Glu-Gly, Gly-D-Ala, Gly-D-Asp, Gly-D-Ser, Gly-D-Thr, Gly-D-Val, Leu-β-Ala, Leu-D-Leu, Gly-Gly-Ala, Leu-Leu-Leu, Phe-Gly-Gly, Tyr-Gly-Gly, Gly-Gly-D-Leu, Gly-Gly-Gly, Gly-Gly-Ile, Gly-Gly-Leu, Gly-Gly-Phe, Val-Tyr-Val, Gly-Phe-Phe, and Leu-Gly-Gly.

The present invention is not limited to a particular phosphorus source. A variety of phosphorus sources are contemplated including, but not limited to: Adenosine-5'-Monophosphate, Adenosine-2',3'-Cyclic Monophosphate, Adenosine-3',5'-Cyclic Monophosphate, Phosphate, Pyrophosphate, Trimetaphosphate, Tripolyphosphate, Triethyl Phosphate, Hypophosphite, Adenosine-2'-Monophosphate, Adenosine- 3'-Monophosphate, Thiophosphate, Guanosine-5'-Monophosphate, Guanosine-2',3'-Cyclic Monophosphate, Guanosine-3',5'-Cyclic Monophosphate, Dithiophosphate, D,L-α-Glycerol Phosphate, β-Glycerol Phosphate, L-α-Phosphatidyl-D,L-Glycerol, D-2-Phospho-Glyceric Acid, D-3-Phospho-Glyceric Acid, Guanosine-2'-Monophosphate, Guanosine-3'-Monophosphate, Phosphoenol Pyruvate, Cytidine-5'-Monophosphate, Cytidine-2',3'-Cyclic Monophosphate, Cytidine-3',5'-Cyclic Monophosphate, Phospho-Glycolic Acid, D-Glucose-1-Phosphate, D-Glucose-6-Phosphate, 2-Deoxy-D-Glucose 6-Phosphate, D-Glucosamine-6-Phosphate, 6-Phospho-Gluconic Acid, Cytidine-2'-Monophosphate, Cytidine-3'-Monophosphate, D-Mannose-1-Phosphate, Uridine-5'-Monophosphate, Uridine-2',3'-Cyclic Monophosphate, Uridine-3',5'-Cyclic Monophosphate, D-Mannose-6-Phosphate, Cysteamine-S-Phosphate, Phospho-L-Arginine, O-Phospho-D-Serine, O-Phospho-L-Serine, O-Phospho-L-Threonine, Uridine-2'-Monophosphate, Uridine-3'-Monophosphate, O-Phospho-D-Tyrosine, Thymidine-5'-Monophosphate, Inositol Hexaphosphate, Thymidine 3',5'-Cyclic Monophosphate, O-Phospho-L-Tyrosine, Phosphocreatine, Phosphoryl Choline, O-Phosphoryl-Ethanolamine, Phosphono Acetic Acid, 2-Aminoethyl Phosphonic Acid, Methylene Diphosphonic Acid, and Thymidine-3'-Monophosphate.

The present invention is also not limited to a particular sulfur source. A variety of sulfur sources are contemplated including, but not limited to: L-Cysteic Acid, Cysteamine, L-Cysteine Sulfinic Acid, Sulfate, Thiosulfate, Tetrathionate, Thiophosphate, Dithiophosphate, L-Cysteine, D-Cysteine, L-Cysteinyl-Glycine, N-Acetyl-L-Cysteine, N-Acetyl-D,L-Methionine, L-Methionine Sulfoxide, L-Methionine Sulfone, S-Methyl-L-Cysteine, Cystathionine, Lanthionine, Glutathione, D,L-Ethionine, L-Methionine, D-Methionine, Glycyl-L-Methionine, L-Djenkolic Acid, 2-Hydroxyethane Sulfonic Acid, Methane Sulfonic Acid, Tetramethylene Sulfone, Thiourea, 1-Thio-β-D-Glucose, D,L-Lipoamide, Taurocholic Acid, Taurine, Hypotaurine, p-Amino Benzene Sulfonic Acid, and Butane Sulfonic Acid.

In some embodiments, the suspension medium is depleted of carbon when the testing substrate is carbon sources, depleted of nitrogen when the testing substrate is nitrogen sources, depleted of phosphorus when the testing substrate is phosphorus sources, and depleted of sulfur when the testing substrate is sulfur sources. In some embodiments, at least one of the testing wells further comprises a gel-initiating agent (e.g., a divalent a divalent metal salt). In certain embodiments, the suspension medium further comprises a gelling agent (e.g., including, but not limited to, gellan gum, carrageenan, and alginate salts). In other embodiments, the suspension medium further comprises a suspending agent (e.g., including, but not limited to, agar, agarose, gellan gum, arabic gum, xanthan gum, carageenan, alginate salts, bentonite, ficoll, pluronic polyols, CARBOPOL, polyvinylpyrollidone, polyvinyl alcohol, polyethylene glycol, methyl cellulose, hydroxymethyl cellulose, hydroxyethyl cellulose, carboxymethyl cellulose, carboxymethyl chitosan, chitosan, poly-2-hydroxyethyl-methacrylate, polylactic acid, polyglycolic acid, collagen, gelatin, glycinin, sodium silicate, silicone oil, and silicone rubber).

In some embodiments, the cells are grown attached to a transferable matrix prior to preparing the cell suspension. In some embodiments, the suspension medium further comprises a transferable matrix. In some embodiments, the transferable matrix comprises a material including, but not limited to, polystyrene and its derivatives, latex, dextran, gelatin, glass, cellulose and extracellular matrix proteins and their derivatives. In other embodiments, the transferable matrix is a microcarrier bead. The present invention is not limited to a particular microcarrier bead. A variety of microcarrier beads are contemplated including, but not limited to, CYTODEX 3, CYTODEX 2, CYTODEX 1, CULTISPHER S, CULTISPHER G, PRONECTIN F coated, FACT-coated, collagen coated, gelatin coated plastic. In some embodiments, the testing device further comprises a time-release composition.

In some embodiments, the observing step comprises observation of a colorimetric indicator. In some embodiments, the colorimetric indicator is included in the suspension medium, while in other embodiments the colorimetric indicator is included in the testing device. The present invention is not limited to a particular colorimetric indicator. For example, in some embodiments, the calorimetric indicator comprises a compound selected from the group including, but not limited to, chromogenic compounds, reducible or oxidizable chromogenic compounds, oxidation-reduction indicators, pH indicators, fluorochromic compounds, fluorogenic compounds, and luminogenic compounds. In some embodiments, the reducible or oxidizable chromogenic compound is selected from the group including, but not limited to, tetrazolium compounds, redox purple, thionin, dihydroresorufin, resorufin, resazurin, ALAMAR BLUE, dodecyl-resazurin, janus green, rhodamine 123, dihydrorhodamine 123, rhodamine 6G, tetramethylrosamine, dihydrotetramethylrosamine, 4-dimethylaminotetramethylrosamine, and tetramethylphenylenediamine.

In some embodiments, the calorimetric indicator calorimetric indicator further comprises an electron carrier compound (e.g., including, but not limited to, phenazine ethosulfate, phenazine methosulfate, 1-methoxy-phenazine methosulfate, 2-amino-phenazine methosulfate, menadione sodium bisulfite, menadione and other 1,4-naphthoquinones, ubiquinone and other 1,4-benzophenones, anthraquinone-2, 6-disulfonate, alloxazines, meldola's blue, ferricyanide salts, ferrocyanide salts, and other ferric and cupric salts).

In some embodiments, the suspension medium further comprises a biologically active chemical. In some embodiments, the observing is visual assisted, while in other embodiments, it is instrument assisted. In some embodiments, the response is a kinetic response. In still further embodiments, the response is selected from the group including, but not limited to, an altered growth rate, differentiation and dedifferentiation.

The present invention further provides a method for comparing at least two animal or plant cell preparations, comprising the steps of: providing a testing device comprising a plurality of testing wells, wherein the testing wells contain at least one testing substrate selected from the group consisting of carbon sources, nitrogen sources, phosphorus sources, sulfur sources, biologically active chemicals, and chromogenic compounds; preparing a first suspension comprising a first cell preparation in an aqueous solution, and a second suspension comprising a second cell preparation in an aqueous solution; introducing the first and second suspensions into separate testing wells of the testing device; observing at least one first response of the first cell preparation to the testing substrate and at least one second response of the second cell preparations to the testing substrate; and comparing the first and second responses. In some embodiments, the testing device is selected from the group including but not limited to a MICROPLATE and a MICROCARD.

The present invention additionally provides a testing system for measuring at least 95 phenotypes of at least one plant or animal cell, comprising a testing device having a plurality of testing wells, wherein the testing wells contain at least one test substrate selected from the group consisting of carbon sources, nitrogen sources, phosphorus sources, sulfur sources, biologically active chemicals, and chromogenic compounds; and an instrument configured for incubating and recording at least one response of the at least one plant or animal cell placed in the testing device. In some embodiments, the testing device is selected from the group including, but not limited to a MICROPLATE and a MICROCARD.

In still further embodiments, the present invention provides a kit for testing animal or plant cells, comprising: a testing device containing a plurality of testing wells, wherein the testing wells contain one or more testing substrates selected from the group consisting of carbon sources, nitrogen sources, phosphorus sources, sulfur sources, biologically active chemicals, and chromogenic compounds; and a cell suspension medium. In some embodiments, the testing device is selected from the group including, but not limited to a MICROPLATE and a MICROCARD.

DESCRIPTION OF THE FIGURES

FIG. 1 is an exploded perspective view of one embodiment of the device of the present invention.

FIG. 2 is a top plan view of the device shown in FIG. 1.

FIG. 3 is a cross-sectional view of the device shown in FIG. 2 along the lines of 3-3.

FIG. 4 is a bottom plan view of the device shown in FIG. 1.

GENERAL DESCRIPTION OF THE INVENTION

Figure 5:
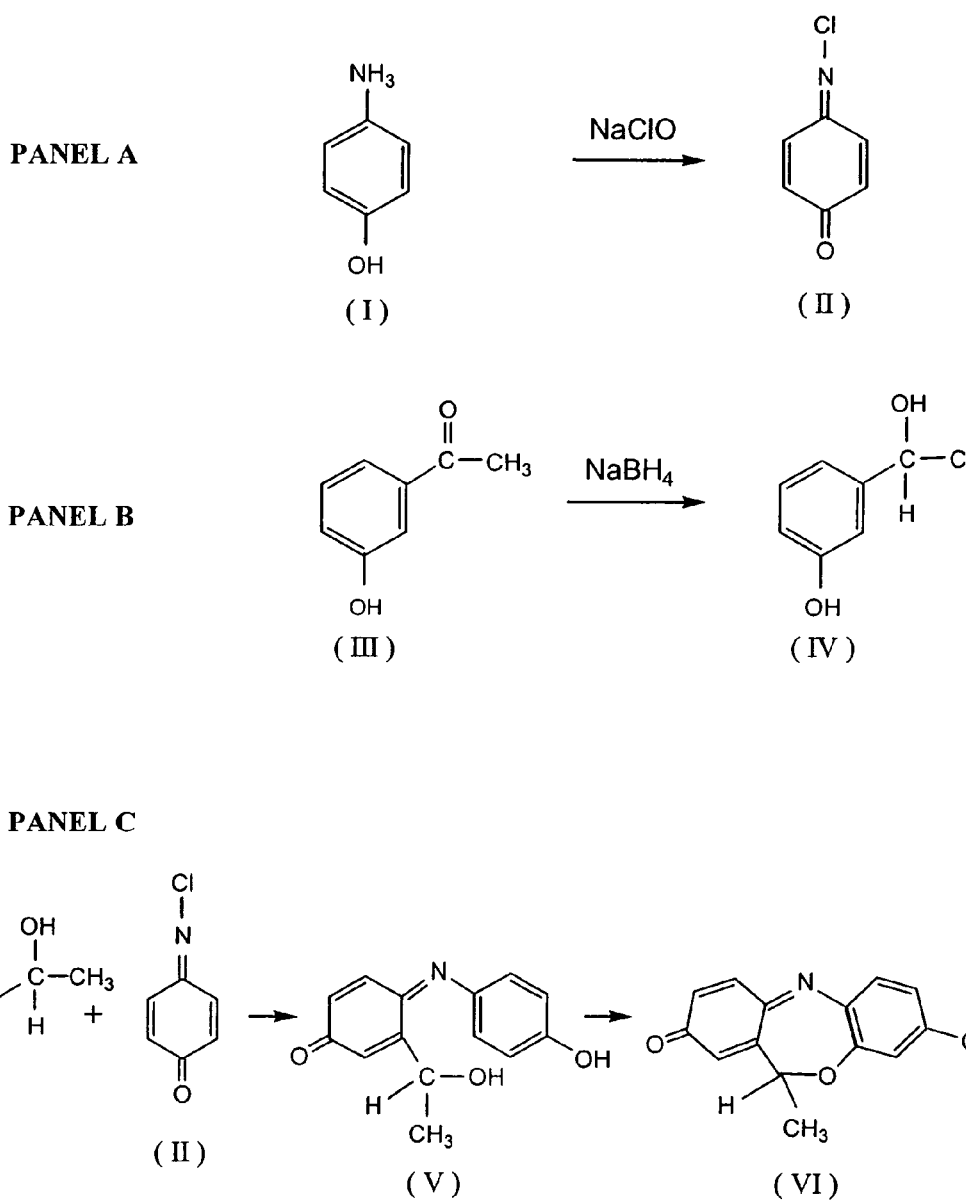
FIG. 5 shows the synthesis pathway of redox purple.

One embodiment of the present invention is based in part on the discovery that various cells (e.g., microbial strains) can be differentiated based on differential biochemical reactions. Surprisingly, it was determined during the development of the present invention that in some cases, the biochemical reactions work best when the cells are contained within a gel matrix. In preferred embodiments, the present invention is suitable for the comparative phenotype testing of microorganisms and other cells. It is intended that comparative phenotypic testing will find use in functional genomics (i.e., whereby cells and/or microbial strains that differ in a defined set of genetic traits are compared).

In one preferred method, the present invention encompasses methods and compositions for the phenotypic testing of *E. coli* and *S. cerevisiae* (i.e., important prokaryotic and eukaryotic "model" organisms for many biological systems). However, it is not intended that the present invention be limited to these organisms. Indeed, it is contemplated that the present invention will find use in analyzing organisms of medical, veterinary, industrial, and environmental importance and/or interest. Thus, it is contemplated that the present invention will find use with various eubacterial and archaebacterial species.

It is not intended that the invention be limited to a particular genus, species, nor group of organisms or cells. In addition to commonly isolated organisms, the range of cell types that can be tested using the methods and compositions of the present invention includes cells that undergo complex forms of differentiation, filamentation, sporulation, etc. Indeed, it is also intended that the present invention will find use with cells of any type, including, but not limited to cells maintained in cell culture, cell lines, etc., including mammalian and insect cells. The compositions and methods of the present invention are particularly targeted toward some of the most economically important organisms, as well as species of clinical importance. As various cells may be characterized using the PHENOTYPE MICROARRAY (PM) testing panels of the present invention, it is not intended that the choice of primary isolation or culture media be limited to particular formulae.

As indicated above, the present invention finds use with prokaryotic (e.g., bacteria) cells, as well as eukaryotic cells. For example, the present invention finds use with cells obtained from various animal and other eukaryotic species. For example, the present invention finds use with mammalian, insect, avian, piscine, reptilian, and amphibian cells. Thus, mammalian cells, including but not limited to human and non-human animal cells, including cells from laboratory, domestic and livestock animals (e.g., canines, felines, equines, bovines, porcines, caprines, ovines, avians [e.g., chickens, turkeys, ostriches, etc.], lagomorphs [e.g., rabbits and hares], rodents [e.g., rats, mice, hamsters, guinea pigs, etc.], and non-human primates), as well as cells obtained from zoo, feral, and wild animals, find use with the present invention. Thus, the present invention finds use with any number of vertebrate, as well as invertebrate animal cells. Examples of invertebrate cells that find use with the present invention include, but are not limited to insects such as fruit flies, cockroaches, mosquitoes, beetles, moths, butterflies, and worms (e.g., *C elegans*). Indeed, it is not intended that the present invention be limited to cells from any particular species. As cell culture methods and techniques for cells from various classes of animals (e.g., mammals, reptiles, amphibians, and insects) are well-known to those in the art, those in the art recognize that the present invention is suitable for use with cells from any animal source.

In addition to animal cells, the present invention finds use with other eukaryotic cells, including but not limited to fungal cells. For example, the present invention finds use with yeasts (e.g., *Candida, Cryptococcus, Saccharomyces, Schizosaccharomyces, Torulopsis,* and *Rhodotorula*) and molds (e.g.,

*Aspergillus, Alternaria, Coccidioides, Histoplasma, Blastomyces, Paracoccidiodes, Penicillium, Fusarium*, etc.). Thus, the present invention encompasses use with dimorphic fungi, as well as fungal species with only one form (i.e., mold or yeast).

The present invention also finds use with such organisms as the actinomycetes (members of the order *Actinomycetales*), which includes a large variety of organisms that are grouped together on the basis of similarities in cell wall chemistry, microscopic morphology, and staining characteristics. Nonetheless, this is a very diverse group of organisms. For example, genera within this group range from the strict anaerobes to the strict aerobes. Some of these organisms are important medical pathogens, while many are saprophytic organisms, which benefit the environment by degrading dead biological or organic matter.

In addition to bacterial and animal cells, the present invention finds use with cells obtained from plants, including but not limited to commercially important plants such as rice, tobacco, maize, and arabidopsis. Indeed, the present invention finds use with agriculturally useful (e.g., crops for food and feed), as well as horticulturally (e.g., decorative plants and flowers) useful plants, and wild plants. It is not intended that the present invention be limited to any particular plant or type of plant. In addition, various plant cells (e.g., root, stem, leaf, flower, etc.) find use with the present invention.

In addition, the present invention finds use with cells from various organs and tissues (e.g., skin, respiratory system, digestive system, urinary tract, reproductive tract, circulatory system, skeletal system, sensory system [e.g., sight, smell, taste, etc.], muscle, and connective tissue). In addition, the present invention finds use with various embryological cell types and cells in various stages of development (e.g., stem cells, oocytes, zygotes, blastocoeles, fibroblasts, etc.). Thus, it is not intended that the present invention be limited to cells of any particular type. Indeed, as cell culture methods and techniques for cells from various organs, tissues, and bodily systems, (e.g., mammals, reptiles, amphibians, and insects) are well-known to those in the art, those in the art recognize that the present invention is suitable for use with cells from any source.

The present invention finds use with normal eukaryotic and prokaryotic cells, as well as abnormal cells, (e.g., cancer cells, cells undergoing apoptosis, mutant cells, pre-cancerous cells, diseased cells, etc.). Cells that have been infected with a pathogenic or other organism (e.g., viruses, bacteria, mycoplasmas, parasites, fungi, etc.), also find use with the present invention. Thus, it is not intended that the present invention be limited to cells in any particular stage of development (e.g., fetal, adult, senescent cells, etc.) or health. Mutant cells such as those that naturally occur, as well as genetically engineered cells (e.g., knock-outs, knock-ins), plasmid-containing cells, transfected cells, transformed cells, chemically-induced mutant cells, radiation-induced mutant cells, etc., also find use with the present invention. The following Table lists a few in vitro tumor cell lines that find use with the present invention. However, it is not intended that the present invention be limited to the few cell lines listed herein.

TABLE 1

Examples of In Vitro Human Tumor Cell Lines

| Colon | CNS | Leukemia | Lung | Mammary | Melanoma | Ovarian | Prostate | Renal |
|---|---|---|---|---|---|---|---|---|
| COLO 205 | SF-268 | CCRF-CEM | A549/ATCC | MCF-7 | LOX IMVI | IGROV1 | DU-145 | 786-O |
| HCC-2998 | SF-295 | HL-60 (TB) | EKVX | MCF-7/ADR-RES | M14 | OVCAR-3 | PC-3 | A498 |
| HCT-15 | SF-539 | K-562 | HOP-62 | HS578T | MALME-3M | OVCAR-4 | | ACHN |
| HCT-116 | SNB-19 | MOLT-4 | HOP-92 | MDA-MB-231/ATCC | SK-MEL-2 | OVCAR-5 | | CAKI-1 |
| HT29 | SNB-75 | RPMI-8226 | NCI-H23 | MDA-MB-435 | SK-MEL-5 | OVCAR-8 | | RXF 393 |
| KM12 | U251 | SR | NCI-H226 | MDA-N | SK-MEL-28 | SK-OV-3 | | SN12C |
| SW-620 | | | NCI-H322M | BT-549 | UACC-62 | | | TK-10 |
| | | | NCI-H460 NCI-H522 | T-47D | UACC-257 | | | UO-31 |

The present invention further finds use with cultured cells, including but not limited to primary cultured cells, cell lines, cell strains, and other cells maintained in cell cultures. Numerous cell lines and strains are available from depositories such as the American Type Culture Collection (ATCC). For example, cell lines such as HeLa, Vero, MDCK, A-9, HFF, CHO, MRC-5, HeP-2, CV-1, BGMK, BHK, BHK-21, A549, Mv1Lu, HEK-293, HT-29, MCF-7, AC-133, CD-4, C3A, hTERT-RPE1, KB, 3T3, Jurkat, IMR-90, F9, PC13, LNCaP, PC-3, US7, HUH-7, NCI-460, NCI-H23, MB-MDA-237, HME, MKN45, CD80-AT, A2780, OVCAR-3, SK-OV-3, NBS-1LB, MCF-10, Rat-1, RTS34St, etc., as well as McCoy and other cells maintained in culture systems, are readily available and suitable for use with the present invention.

In addition, the present invention finds use with cells with selectable markers (i.e., the use of a gene which encodes an enzymatic activity that confers resistance to an antibiotic or drug upon the cell in which the selectable marker is expressed). Selectable markers may be "dominant"; a dominant selectable marker encodes an enzymatic activity, which can be detected in any mammalian cell line. Examples of dominant selectable markers include the aminoglycoside 3' phosphotransferase gene (also referred to as the neo gene) which confers resistance to the drug G418 in mammalian cells, the hygromycin G phosphotransferase (hyg) gene which confers resistance to the antibiotic hygromycin, the bacterial xanthine-guanine phosphoribosyl transferase gene (also referred to as the gpt gene) which confers the ability to grow in the presence of mycophenolic acid, and the chloramphenical acetyl transferase gene (also referred to as the cat gene) which confers resistance to chloramphenicol acetyl transferase. Other selectable markers are not dominant in that their use must be in conjunction with a cell line that lacks the relevant enzyme activity. Examples of non-dominant selectable markers include the thymidine kinase (tk) gene which is used in conjunction with tk⁻ cell lines, the cad gene (i.e., encoding the CAD protein, which possesses the first three enzymatic activities of de novo uridine biosynthesis), which is used in conjunction with CAD-deficient cells (i.e., UrdA mutants), and the mammalian hypoxanthine-guanine phosphoribosyl transferase (hprt) gene which is used in conjunction with hprt⁻ cell lines. A review of the use of selectable markers in mammalian cell lines is provided in Sambrook et al., (Sambrook et al., Molecular Cloning: A Laboratory Manual, 2nd ed., Cold Spring Harbor Laboratory Press, New York [1989], at pp. 16.9-16.15.)

In some embodiments, plates essentially similar in structure and/or function to microtiter plates commonly used in the art and commercially available from numerous scientific supply sources (e.g., MICROPLATE testing plates from Biolog) are used. It is also intended that the present invention encompasses various testing formats, including but not limited to other multi-well devices. Thus, in addition to standard microtiter plate testing methods, the present invention finds use with various gelling agents, including but not limited to alginate, carrageenan, and gellan gum (e.g., GELRITE and/or PHYTAGEL), as described in U.S. Pat. Nos. 5,627,045, and 5,882,882, and 5,989,853, as well as the MICROCARD miniaturized testing plates described in U.S. Pat. Nos. 5,589,350 and 5,800,785, all of which are herein incorporated by reference.

Thus, in some further embodiments, the present invention is used with various gelling agents, including but not limited to alginate, carrageenan, and gellan gum (e.g., GELRITE and/or PHYTAGEL). Because the cells are trapped within the gel matrix, these embodiments of the present invention provide great improvements over standard microtiter plate testing methods in which liquid cultures are used. Unlike the liquid format, the gel matrix of the present invention does not spill from the microtiter plate, even if the plate is completely inverted. This safety consideration highlights the suitability of the present invention for use with organisms or other cells that are easily aerosolized. The present invnetion finds use in the educational setting, where safety is a primary concern. The present invention permits novices to work with bacteria and study their biochemical characteristics with a reduced chance of contamination, as compared to other testing systems. In addition, the present invention permits novices to work with infected cells (e.g., virally-infected cells harvested from cell cultures), with a reduced chance of contamination.

The gel matrix system of the present invention also offers other important advantages. For example, over incubation periods of several hours, cells will often sink to the bottom of testing wells and/or attach or clump to other cells, resulting in a non-uniform suspension of cells within the wells. This non-uniformity can result in a non-uniform response of the cells in the well. Clumping artifacts perturb the optical detection of cellular responses. Thus, because the present invention provides methods and compositions, which trap the cells in a gel matrix within the wells, the cells are uniformly suspended, and have uniform access to nutrients and other compounds in the wells. Thus, the present invention serves to make this type of cell testing as reproducible and homogenous as possible. Furthermore, in natural settings, cells often grow attached to surfaces or in contact with other cells (e.g., in biofilms or monolayers). By providing contact between the cells and a semi-solid, gel support, the gel matrix of the present invention simulates the natural state of cell growth. In addition, the gel matrix decreases the diffusion of oxygen to the cells and helps protect them from oxidative damage.

In some embodiments, cells that are anchorage-dependent are utilized in the methods of the present invention. For these cells, methods known in the art are used to culture the cells in vitro. In some cases, cells are grown on microcarrier beads, which are then readily homogenously suspended in a gel. In other embodiments, cells (i.e., anchorage-independent cells) are grown in suspension prior to testing.

As indicated above, various cells may be characterized using the present invention. Thus, it is not intended that the choice of primary isolation or culture media be limited to particular formulae. In addition to commonly isolated organisms, the range of cell types that can be tested using the methods and compositions of the present invention includes cells that undergo complex forms of differentiation filamentation, sporulation, etc. For example, in one embodiment, organisms such as the actinomycetes are grown on an agar medium, which stimulates the production of aerial conidia. This greatly facilitates the harvesting of organisms for inoculation in the present invention. However, it is not intended that the present invention be limited to actinomycetes. Indeed, the present invention provides methods and compositions for the testing of fungi (e.g., yeasts and molds), as well as bacteria other than actinomycetes. As with the actinomycetes, these organisms may be grown on any primary isolation or culture medium that is suitable for their growth, although it is preferred that the primary isolation or culture medium used promotes the optimal growth of the organisms. For cell lines and cell cultures (i.e., mammalian, plant, and/or insect cells maintained in vitro), the cells are grown in cell culture media (e.g., Eagle's Minimal Essential Medium, etc.), suitable for cell growth.

In one embodiment, a microtiter plate (e.g., a MICROPLATE testing plate) format is used. In this embodiment, the gel-forming matrix containing suspended cells is used to inoculate the wells of a MICROPLATE or another receptacle. At the time of inoculation, the gel-forming matrix is in liquid form, allowing for easy dispensing of the suspension into the compartments. These compartments contain dried biochemicals and cations. Upon contact of the gel-forming matrix with the cations, the suspension solidifies to form a soft gel, with the cells evenly distributed throughout. This gel is sufficiently viscous or rigid that it will not fall out of the MICROPLATE should the plate be inverted. However, it is not intended that the present invention be limited to these gel-forming matrix embodiments, as solutions also find use with the present invention.

In another embodiment, a microcard format is used. As shown in FIGS. 1-4, one embodiment of the device of the present invention comprises a housing (100) with a liquid entry port through which the sample is introduced. The housing further contains a channel (110) providing communication to a testing region (120) so that a liquid (not shown) can flow into a plurality of wells or compartments (130). The channel (110) is enclosed by the surface of a hydrophobic, gas-venting membrane (140) adapted for forming one surface of the wells (130) and attached to one side of the housing (100). The housing (100) can be sealed on its other side by a solid base (150). In other embodiments, a flexible tape (not shown) may be substituted for the solid base (150) or the solid base (150) may be molded so as to be integral with the housing (100).

After filling the device with the gel-forming matrix containing cells, (not shown) an optional non-venting material such as tape (e.g., polyester tape) (160) can be adhered to the outer surface of the gas-venting membrane (140) to seal it against evaporation of the gel matrix within the device through the gas-venting membrane. At the time of delivery, the gel-forming matrix with suspended cells is in liquid form. Once the liquid comes into contact with the compounds present in the testing region, a gel matrix is produced, trapping the suspended cells. However, it is not intended that the present invention be limited to these gel-forming matrix embodiments, as solutions also find use with the present invention.

BACs

Biologically active chemicals (BACs) constitute major, important commercial product lines. These compounds are generally focused toward enhancing the health of humans, other animals and plants. The largest markets are for drugs, especially antimicrobials and pharmaceuticals for human use. Because of the large market, major efforts and expenditures are made annually, in the pursuit of better and more effective BACs.

Antimicrobials constitute a major category of BACs. Although many antimicrobials have been developed and marketed, there remains a critical need for novel antimicrobials acting at novel targets. To some extent, this need is driven by the rapid emergence of antimicrobial-resistant pathogens. The appearance of strains resistant to all available drugs (e.g., enterococci), and the lag in the discovery of new antimicrobials has resulted in a renewed search for compounds effective against these resistant organisms. Despite this critical need and substantial research efforts, no new chemical entity has been approved by the U.S. Food and Drug Administration (FDA) for bacterial disease treatment for more than 20 years (Trias and Gordon, Curr. Opin. Biotechnol., 8:757-762 [1997]; See also, Bianchi and Baneyx, Appl. Environ. Microbiol., 65:5023-5027 [1999]).

The situation is particularly desperate in the area of nosocomial infections, as infections with methicillin-resistant *Staphylococcus aureus* (MRSA) and vancomycin-resistant *Enterococcus faecium* (VRE) have increased in frequency. There is a very real fear that high-level vancomycin resistance will spread within the staphylococci. Indeed, since 1996, vancomycin-intermediate *S. aureus* isolates (VISA; with vancomycin minimum inhibitory concentration [MIC] of 8-16 µg/ml), have been identified in Europe, Asia, and the United States. This emergence of reduced vancomycin susceptibility in *S. aureus* increases the chances that some strains will become fully resistant, and currently used antimicrobials will become ineffective against such strains. This is of special concern because the emergence of community-acquired MRSA infections, has led to the increasing use of vancomycin against these organisms. Because very few therapies are available for treatment of MRSA, the confirmed reports of VISA strains demonstrating reduced susceptibility to vancomycin, the drug of last resort to treat MRSA, is of great concern (See e.g., Khurshid et al., MMWR, 48:1165-1167 [2000]; See also, Baughman et al., MMWR 48:1167-1171 [2000]).

Currently, the most commonly used antimicrobials are directed against a surprisingly small number of cellular functions as targets (e.g., cell wall, DNA, RNA, and protein biosynthesis). Table 2 summarizes these targets, gene products, and some antimicrobial classes that interact with the targets currently used. Instances of organism resistance to these antimicrobials are well-documented and widespread. Thus, it is clear that new antimicrobials are needed to counter the problem of increasing antimicrobial resistance.

The efforts to discover new, effective antimicrobials typically involve two steps. In the first step, one or more drug targets are defined. Targeting of new pathways beyond those shown in Table 2 will likely play an important role in this stage of development. In the second step, potentially active chemicals are tested and evaluated to find those that have the desired activity without engendering undesirable side effects.

TABLE 2

Targets of Some Widely Used Antimicrobials*

| Target Category and Gene Product | Antimicrobial Class |
| --- | --- |
| Protein Synthesis | |
| 30S Ribosomal Subunit | Aminoglycosides, Tetracyclines |
| 50S Ribosomal Subunit | Macrolides, Chloramphenicol |
| tRNA$^{ILE}$ Synthetase | Mupirocin |
| Elongation Factor G | Fusidic Acid |
| Nucleic Acid Synthesis | |
| DNA Gyrase A Subunit; Topoisomerase IV | Quinolones |
| DNA Gyrase B Subunit | Novobiocin |
| RNA Polymerase Beta Subunit | Rifampin |
| DNA | Metronidazole |
| Cell Wall Peptidoglycan Synthesis | |
| Transpeptidases | Beta-lactams |
| D-Ala-D-Ala Ligase Substrate | Glycopeptides |
| Antimetabolites | |
| Dihydrofolate Reductase | Trimethoprim |
| Dihydropteroate Synthesis | Sulfonamides |
| Fatty Acid Synthesis | Isoniazid |

*After, Moir et al., Antimicrob. Agents Chemother., 43: 439–446 [1999]).

Another major category of BACs are pharmaceuticals designed to counteract human diseases. Diseases can be viewed as abnormalities in physiological pathways of cells. The main components of these pathways are proteins (enzymes, receptors, etc.) encoded by genes and expressed within the cells affected by the disease. These drugs usually exert their pharmaceutical effect by interacting with key proteins (i.e., drug targets) to restore the normal functioning of the protein or to inactivate the protein and compensate for a physiological pathway abnormality.

As with antimicrobials, the process of developing pharmaceuticals involves two steps: (1) defining targets and then, (2) testing potential active chemicals to find the ones that specifically interact with the target to produce the desired effect without undesirable side effects. Although much work has been done in this area, there remains a need for improvements in the efficiency and effectiveness of the testing and evaluation of these chemicals.

In response to the pressures to generate more promising drugs, pharmaceutical and biotechnology companies have turned toward more rapid high-throughput methods to find and evaluate lead compounds. These lead compounds are typically selected by testing (e.g., screening) large libraries of compounds compiled from a wide variety of sources, using collections of extracts, chemicals synthesized by combinatorial chemistry approaches, or through rational drug design. Unfortunately, technologies such as combinatorial chemistry only look at the effect of the drugs on the proposed target, and they do not measure the effect on other cellular processes. A chemical may be an excellent candidate based on its interaction with the target protein, but it may also interact with other proteins in the cell and cause side effects. Thus, a major problem remains, in that the drug developer must sort through promising drug candidates to see how they effect other aspects of cell function, as well as how the drug candidates interact with other drugs that may be used simultaneously. Despite advances in these fields, there remains a need for highly sensitive and specific, yet cost-effective and easy-to-use methods for the identification and development of BACs that are effective in the treatment of disease.

DETAILED DESCRIPTION OF THE INVENTION

The present invention is predicated in part on the discovery that various cells or cell types may be identified, differentiated, and characterized based on differential biochemical reactions. The multiple test medium of the present invention permits presumptive and rapid testing of various specimens and cells. In particular, this invention in the form of a kit, is suitable for the easy and rapid biochemical testing of various cells, including commonly isolated bacteria, as well as actinomycetes and fungi (i.e., yeasts and molds), in addition to animal (e.g., mammalian and insect cells, etc.), and plant cells. In particular, the present invention provides compositions and methods for the phenotypic analysis of cells.

Phenotypic Analysis

The Darwinian belief in a common ancestry of Earth's gene pool and the concept of evolution by gene duplication, mutation, and rearrangement are at the foundation of the new field of genomics, a field that has evolved rapidly in recent years by successfully utilizing microorganisms as models. In genomic analysis, genes whose function(s) and coded protein are known in one cell type are used as a basis for extrapolation when a similar coding sequence is found in another cell type.

Initially, the pace of genomic research was limited by DNA sequencing technology. However, with new techniques developed in recent years, the pace of genomic sequencing has greatly accelerated and the sequencing effort is no longer considered a rate-limiting step. Great strides have been made in the sequencing of various microorganisms, including many with relatively small genomes (approx. 470 genes in the bacterium *Mycoplasma genitalium* to approx. 12,000 genes in the protozoan *Oxytricha similis*). As of September, 1997, the complete genomic sequences of 12 microbes had been obtained (See, Pennisi, Science 277:1432-1434 [1997]), representing the three domains of cellular life: eubacteria (e.g., *Escherichia coli*, and *Bacillus subtilis*), archaea (e.g., *Methanococcus jannaschii*, and *Methanobacterium thermoautotrophicum*), and eucarya (e.g., *Saccharomyces cerevisiae*). The annotation of genes corresponding to open reading frames (ORFs) relies heavily on microorganisms, especially *E. coli*. Often the extrapolation from DNA sequence to enzyme or regulatory function is based upon sequence data from the best studied microbes (e.g., *E. coli*, *B. subtilis*, and *S. cerevisiae*) or from heterologous sequences that are cloned into *E. coli*. Yet even with a great deal of extrapolation, the percentage of genes with an "ascribed function" ranges from only 44% to 69%. There is a tremendous amount of functional information that remains to be determined and understood. Indeed, genome sequencing has reached a turning point, as indicated by Smith et al., "The next important challenge is to determine, in an efficient and reliable way, something about the function of each gene in the genomes" (Smith et al, Science 274:2069-2074 [1997]).

Over the past three decades, biologists have sought tools that would allow them to understand the workings of cells by analyzing all of the cell's genes simultaneously. The first breakthrough in this endeavor of "global analysis" came in the early 1970s with the introduction of one dimensional protein electrophoresis, which allowed the separation and observation of nearly all of a cell's proteins. This innovation was soon followed by the superior resolution obtained by two dimensional separation methods. One-dimensional methods were next developed for DNA and mRNA analysis (i.e., Southern and Northern blot analysis). Nucleic acid arrays (See e.g., DeRisi et al., Science 278:680-686 [1997]) and gene fusion arrays (See e.g., Glaser, Genet. Engineer. News, Sep. 15, 1997, at pages 1 and 15), have been developed which can analyze the genotype and gene expression levels of cells.

By determining the function of genes, the analysis can go a step further, through the ascertainment of groups of genes which are regulated similarly and which, by implication, are likely to provide related functions in the cell. Though clearly of great value, these technologies still do not indicate the function of the gene, nor do they describe the phenotypic changes that occur in the cell of interest due to the presence of different alleles of that gene. The present invention solves these problems, by providing methods and compositions to assay the function of genes directly in cells. Unlike previous methods and compositions, the present invention permits the analysis of thousands of cell phenotypes simultaneously. This cellular approach is nicely complementary to the molecular techniques; it is contemplated that those skilled in the art will utilize the present invention in conjunction with molecular methods to characterize a wide variety of cell types.

As indicated above, the present invention is intended for use with eukaryotic, as well as prokaryotic cells. Indeed, the ease of finding phenotypic changes has also been demonstrated recently in yeast. As of 1996, of the 6000 genes in the chromosome of *S. cerevisiae*, less than one half had been known, and 30% could not be assigned a function (Goffeau et al., Science 274:546-567 [1996]). Subsequently, Smith and coworkers developed a method that allowed the introduction of Ty1 insertion mutations into 97% of the genes on chromosome V. Testing this collection with only seven phenotypic tests based on the growth rate of the organism on certain media, they found detectable changes in 61.6% of the mutant strains (Smith et al., Science 274:2069-2074 [1996]). Moreover, these authors observed that disruption of many genes resulted in multiple phenotypes, and in fact uncovered previously undetected phenotypes for previously described genes, some of which were quite unexpected. In contrast, the present invention provides a much larger number, as well as more narrow phenotypic tests that provide much more detailed information about the change(s) in cell physiology detectable in yeast cells.

The present invention provides useful, practical, efficient and cost-effective systems, including in some embodiments, an instrument which is used in conjunction with disposable testing panels, to allow the direct and simultaneous analysis of cells and cell lines for thousands of phenotypes. The present invention provides methods and compositions for the phenotypic analysis of prokaryotic, as well as eukaryotic cells. Indeed, the present invention is not limited to any particular organism, cell, or testing format.

In many embodiments, the present invention provides one or more testing panels, with each test panel including substrates for 95 phenotypic tests. However, in other embodiments, each test panel includes substrates for many more than 95 phenotypic tests (e.g., 384). It is not intended that the present invention be limited to any particular format of test panel or any particular number of test substrates utilized per panel. Indeed, it is intended that the present invention provides a flexible testing format that is suitable for customization to the number of substrates, test panels, etc., as needed by the user.

In one embodiment, the substrates in the test panel include various carbon sources, while in other embodiments, the test panels include nitrogen, sulfur, phosphorus, and/or other substrates. Thus, it is intended that the present invention encompasses testing panels with test substrates of any type suitable for the phenotypic testing of various cells.

In one preferred method, the present invention encompasses methods and compositions for the phenotypic testing of *E. coli*, which is an important "model" organism for many biochemical systems. In another embodiment, the present invention provides methods and compositions for the testing of isogenic strains with known mutations, in order to identify and characterize unexpected and/or misleading phenotypes.

In other preferred embodiments, the present invention provides methods and compositions to determine the function of genes of interest. For example, the present invention provides means to analyze and compare source strains and daughter strains for their phenotypic differences. Thus, in one embodiment, the gene of interest, with an unknown function in the source strain, is completely or partially inactivated by creating an altered allele in an isogenic daughter strain. Then, the source strain and the daughter strains are cultured simultaneously under identical conditions and tested in the testing panels described above in order to determine the phenotypic consequences of the alteration of gene function.

In other embodiments, a third cell strain or cell line is created. This third cell strain or cell line is a revertant of the mutation, derived from the daughter strain. It is intended that this approach will find use in situations in which the cells contain mutations that strongly select for secondary suppressor mutations in the cell line that otherwise can easily go unnoticed. By analyzing a revertant along with the source and daughter strains, one can tell whether any and all phenotypic differences between source and daughter are due to the original mutation or to second site mutations.

In still other embodiments, a gene of interest from another cell type is sequenced and its homolog is mutated in *E. coli* and/or *S. cerevisiae*. In yet other embodiments, a gene of interest from another cell type is cloned and expressed at a physiologically appropriate level in *E. coli* and/or *S. cerevisiae*. In addition, the present invention provides methods and compositions for the direct phenotypic analysis of cells that have been mutated. The present invention further contemplates knocking out expression of genes transiently with antisense RNA, and performing phenotypic analysis on cells with a transiently inactivated gene.

One limitation of the current phenotypic testing methods is the range of phenotypic tests covered, which is currently limited to carbon source oxidation tests. In contrast, the present invention provides methods and compositions for the analysis of thousands of phenotypic characteristics. For example, in some embodiments, one or more sets of 95 (or more) tests will be aimed toward each of the following groups of tests, which encompass the majority of the catabolic functions of cells, as well as the majority of the biosynthetic functions of cells, and much of the macromolecular machinery of the cell including the ribosome, DNA and RNA polymerases, cellular respiration, transport and detoxification systems, cell wall, and inner and outer membranes: (1) carbon source oxidation tests (including peptide substrates), (2) carbon source fermentation tests, (3) amino and/or carboxy peptidase tests, (4) nitrogen source tests, (5) phosphorus source tests, (6) sulfur source tests, (7) auxotrophic tests for all essential metabolites such as amino acids, vitamins, polyamines, fatty acids, and/or nucleosides; (8) sensitivity tests for antimicrobials (including antibiotics and other drugs); (9) sensitivity tests for amino acid analogs, sugar analogs, nucleoside and base analogs, and/or mutagens, (10) sensitivity tests for dyes, detergents, heavy metals, oxidizing and/or reducing agents, and (11) other tests of general physiological interest such as growth at different pH concentrations, salt concentrations, utilization of different osmotic balancers, and/or ability to traverse various diauxic "shift-downs." The general issues in designing each group of tests are discussed below.

In addition to the carbon sources in such commercially available testing panels as the ES MICROPLATE testing plate (Biolog), it is contemplated that any number of additional carbon sources of interest will be included in the present invention. For example, it is contemplated that peptides be included as carbon sources, as during the development of the present invention, it was observed that these carbon sources can provide very useful phenotypic tests. For example, it has been determined that *E. coli* can use D- and L-alanine, D- and L-serine, D- and L-threonine, D- and L-aspartate, L-asparagine, L-glutamine, L-glutamate, and L-proline as carbon sources. It is further contemplated that various chromogenic amino and carboxypeptidase substrates be used in the present invention.

Carbon source fermentation tests measure acid production from a variety of sugars, and therefore they can provide phenotypic information that is different from carbon source oxidation tests. These tests are performed using a chromogenic pH indicator, including, but not limited to such compounds as bromthymol blue, bromcresol purple, and neutral red.

The present invention also provides methods and compositions to observe utilization of nitrogen, phosphorus, and/or sulfur sources, using an indicator system (e.g., tetrazolium reduction) to demonstrate substrate utilization. Various nitrogen sources are contemplated for use in the present invention, including, but not limited to D-alanine, L-alanine, L-arginine, D-asparagine, L-asparagine, D-aspartic acid, L-aspartic acid, L-cysteine, L-cystine, D-glutamic acid, L-glutamic acid, L-glutamine, glycine, L-histidine, L-homoserine, D,L-B-hydroxy-glutamic acid, L-isoleucine, L-leucine, L-phenylalanine, L-proline, D-serine, L-serine, L-tryptophan, L-tyrosine, glutathione (as well as any peptide containing the above amino acids), adenosine, deoxyadenosine, cytosine, cytidine, deoxycytidine, D-glucosamine, D-galactosamine, D-mannosamine, N-acetyl-D-glucosamine, N-acetyl-D-galactosamine, N-acetyl-D-mannosamine, methylamine, ethylamine, butylamine, isobutylamine, amylamine, ethanolamine, ethylenediamine, pentamethylenediamine, hexamethylenetriamine, phenylethylamine, histamine, piperidine, pyrrole, B-alanine, glycocol, acetylglycocol, phenylglycine-o-carbonic acid, hippuric acid, urocanic acid, α-aminovaleric acid, γ-aminovaleric acid, α-aminoisovaleric acid, γ-aminoisovaleric acid, α-aminocaproic acid, γ-aminocaprylic acid, acetamide, lactamide, glucuronamide, formamide, propionamide, methoxylamine, thio-acetamide, cyanate, urea, diethylurea, tetraethylurea, biuret, parabanic acid, alloxan, alloxantine, allantoin, uric acid, theobromine, guanine, and xanthine. Example 18 provides a description of experiments conducted using various nitrogen sources.

Various phosphorous sources are contemplated for use in the present invention, including, but not limited to pyrophosphate, trimetaphosphate, 2'-mononucleotides, 3'-mononucleotides, 5'-mononucleotides, 2',3'-cyclic nucleotides, 3',5'-cyclic nucleotides, aryl-phosphates (e.g., p-nitrophenyl phosphate), phosphonates (e.g., aminoethyl phosphonate), sugar phosphates (e.g., glucose-1-phosphate), acid phosphates (e.g., 2-phospho-glyceric acid), aldehyde phosphates (e.g., glyceraldehyde-3phosphate), α-glycerol phosphate, β-glycerol phosphate, inositol phosphates (e.g., phytic acid), phosphite, hypophosphite, and thiophosphate. Example 18 provides a description of experiments conducted using various phosphorous sources.

Various sulfur sources are contemplated for use in the present invention, including, but not limited to sulfur, thiosulfate, thiophosphate, metabisulfite, dithionite, tetrathionate, polysufide, cysteine, cystine, cysteic acid, cysteamine, cysteine sulphinic acid, cystathionine, lanthionine, ethionine, methionine, N-acetyl-methionine, N-acetyl-cysteine, glycyl-methionine, glycyl-cysteine, glutathione, L-djenkolic acid, L-2-thiohistidine, S-methyl-cysteine, S-ethyl-cysteine, methionine sulfoxide, methionine sulfone, taurine, thiourea, and thioglycolate. Example 18 provides a description of experiments conducted using various sulfur sources.

In addition, various amino and carboxy peptidases are contemplated for use in the present invention, including, but not limited to dipeptides containing all natural L-amino acids on the amino terminal, and all natural L-amino acids on the carboxy terminal, as well as suitable non-protein occurring amino acids, such as pyroglutamate, ornithine, α-amino butyrate, D-amino acids, etc.

The present invention also provides methods and compositions for auxotrophic testing using a minimal medium supplemented with various single nutrients. In one embodiment, the growth in the well where the organism is capable of using the nutrient results in a color change via tetrazolium reduction. Thus, mutations that result in auxotrophy cause the strain to fail to grow in all wells except the one containing the necessary nutrient. In some cases, the wells contain more than one nutrient, in order to allow analysis of genes that affect more than one biosynthetic pathway (e.g., isoleucine+valine (ilv), arginine+uracil (car), and purine+pyrimidine+histidine+tryptophan+nicotinamide (prs)). Various compounds are contemplated for use in this embodiment of the present invention, including, but not limited to L-amino acids, D-glutamic acid, D-aspartic acid, D-alanine, vitamins, nucleosides, polyamines, and fatty acids. In an alternative embodiment, a "drop out" medium or substrate is used. In this system, a complex defined supplement is used and one nutrient is missing in the substrate dispensed in each well (i.e., the medium lacks one nutrient of the substrate complex). Example 18 provides a description of experiments conducted to determine the auxotrophic requirements of an organism.

It is contemplated that for some embodiments of the present invention for sensitivity testing, a minimal medium is used, while in other cases, an enriched and/or defined medium is preferable. Furthermore, it is not intended that the present invention be limited to any particular testing substrates, as it is contemplated that any testing substrate suitable for use with the present invention will be utilized. In addition, as in other reactions, in one embodiment, growth in the wells can result in a color change via tetrazolium reduction. For each toxic agent, the optimal concentration for use in testing for sensitivity/resistance is determined for the cell type to be tested. Various sensitivity tests are contemplated, including tests utilizing compounds including, but not limited to oxidizing agents, reducing agents, mutagens, antibiotics, amino acid analogs, sugar analogs, nucleoside and base analogs, dyes, detergents, toxic metals, and toxic organics.

The present invention also provides methods and compositions for testing growth at extremes of pH and salt, and the compensatory effect of several compatible solutes. In addition, diauxic testing is performed with a limiting amount of a favored nutrient present in a well. In this embodiment, the cells need to adapt from a more favored to a less favored nutrient, and the lag and growth kinetics for numerous substrates can be measured quickly and efficiently in a micro titer plate format.

It is also contemplated that in some embodiments, the present invention be used with various gelling agents, including, but not limited to agar, pectin, carrageenan, alginate, alginic acid, silica, gellans and gum. In one embodiment, the pectin medium of Roth (U.S. Pat. Nos. 4,241,186, and 4,282,317; herein incorporated by reference) is used. However, this is not a preferred embodiment, as pectin is not a colorless compound itself. In one particularly preferred embodiment, the gellan of Kang et al. (U.S. Pat. Nos. 4,326,052 and 4,326,053, herein incorporated by reference) is used. In another preferred embodiment, carrageenan is used as the gelling agent. In a particularly preferred embodiment, carrageenan type II or any carrageenan which contains predominantly the iota form of carrageenan is used. In these embodiments, the cells to be tested are mixed in a suspension comprising a gelling agent, and then inoculated into a well, compartment, or other receptacle, which contains the biochemical(s) to be tested, along with a gel-initiating agent such as various cations. Upon contact of the gelling agent with the gel-initiating agent (e.g., cations), the suspension solidifies to form a viscous colloid or gel, with the cells evenly distributed throughout.

Indicator Plates of the Present Invention

The present invention also provides multitest indicator plates that are generally useful in the phenotypic characterization of various cells, as well as identification and antimicrobial sensitivity testing of microorganisms. This medium and method are particularly targeted toward some of the most economically important organisms, as well as species of clinical importance. However, it is not intended that the invention be limited to a particular genus, species nor group of organisms. Indeed, it is contemplated that any cell type (e.g., microorganisms, as well as plant, mammalian, and insect cells) will find use in the present invention.

The present invention contemplates a testing device that is a MICROPLATE similar in structure to commonly used microtiter plates commonly used in the art and commercially available from numerous scientific supply sources (e.g., Biolog, Fisher, etc.). Thus, in one embodiment, standard 96-well microtiter plates are used. In other embodiments, microtiter plates with more wells are used (e.g., 384 well and 1536 well microtiter plates). Furthermore, the microtiter plate format is suited for methods for kinetic analysis of substrate utilization by cells.

For example, in one embodiment, a test panel for detailed phenotypic testing of *E. coli* and *S. typhimurium* called the "ES MICROPLATE" testing plate (Biolog) was used. This panel contains 95 carbon sources, which can be utilized by most strains of these species. To perform a test, identical cell suspensions of isogenic parental and mutant strains are prepared and pipetted into the 96 wells of a microtiter plate (e.g., a MICROPLATE testing plate). The cells are incubated for approximately 16-24 hours and if a substrate oxidation occurs in a given well, a violet/purple color is produced due to coupled reduction of a tetrazolium dye. Quantitation of the intensity of color is possible through use of a microplate reader or comparable instrument, or the plates can be compared by eye. For observation of differences at a finer level, the MICROPLATE testing plates can be read at frequent time intervals to determine the kinetics of color formation (i.e., carbon source oxidation rates) in each of the 96 wells. For a typical strain, perhaps 80 to 85 wells provide positive reactions and useful data.

An alternate embodiment of the invention generally relates to a "micro titer card" (i.e., such as the MICROCARD developed by Biolog) device for the multiparameter testing of chemical, biochemical, immunological, biomedical, or microbiological samples in liquid or liquid suspension form in a small, closed, easy-to-fill device, and is particular suitable for multiparameter testing and identification of microorganisms. It is not intended that the present invention be limited to a particular sized device. Rather, this definition is intended to encompass any device smaller than the commonly used, 96-well microtiter plates. In one particularly preferred embodiment, the miniaturized cards (e.g., MICROCARD) is approximately 75 mm in width and 75 mm in length, and approximately 3 mm in depth. Approximately one-tenth the volume of cells is used to inoculate the compartments of the device, as compared to standard microtiter plates. Indeed, the present invention contemplates a device comprising: a) a housing; b) a testing region contained within the housing; c) a liquid receiving means on an external surface of the housing; d) a liquid flow-directing means providing liquid communication between the testing region and the liquid receiving means; and e) a gas-venting, liquid barrier in fluidic communication with the testing region.

After the device has been filled, a non-venting, sealing tape can be applied to the device to cover the gas-venting, liquid barrier to reduce the evaporation of the liquid from the device. In some embodiments, the tape can permit the molecular diffusion of oxygen and/or carbon dioxide into or out of the device to maintain the desired chemical or biochemical environment within the device for successful performance of the test. Where the liquid receiving means comprises liquid entry ports, a similar closing tape can be applied to close the port or ports to prevent spilling and evaporation of the liquid therefrom.

With any of the testing formats, the visual result that is detected by eye or by instrument can be any optically perceptible change such as a change in turbidity, a change in color, a change in fluorescence, or the emission of light, such as by chemiluminescence, bioluminescence, or by Stokes shift. Color indicators may be, but are not limited to, redox indicators (e.g., tetrazolium, resazurin, and/or redox purple), pH indicators, or various dyes and the like. Various dyes are described in U.S. Pat. Nos. 4,129,483, 4,235,964 and 5,134,063 to Barry R. Bochner, hereby incorporated by reference. See also B. R. Bochner, Nature 339:157 (1989); and B. R. Bochner, ASM News 55:536 (1990). A generalized indicator useful for practice of the present invention is also described by Bochner and Savageau. See B. Bochner and M. Savageau, Appl. Environ. Microbiol., 33:434 (1977).

Testing based on the redox technology is extremely easy and convenient to perform. A cell suspension is prepared and introduced into the testing compartments of the device. Each compartment is prefilled with a different substrate.

In a preferred embodiment, all wells are prefilled with test formula comprising a basal medium that provides nutrients for the cells, a color-change indicator, as well as testing substrate(s) in sufficient concentration to trigger a color response when the testing substrate is utilized by the cell suspension upon inoculation into the wells for testing (i.e., each well contains either the same or a different testing substrate). In a particularly preferred embodiment, redox purple is used as a redox indicator in the present invention.

One of the principal uses of the present invention is as a method and device for simple testing and speciation of microorganisms. In some embodiments, the present invention provides microbiological testing methods and compositions based on the redox technology discussed above, wherein a sample of a pure culture of microorganism is removed from a culture medium on which it has been grown and suspended at a desired density in saline, water, gel, gelling agent, buffer, or solution (e.g., PPS). This suspension is then introduced into the compartments of the testing device, which have been prefilled with basal medium, indicator, and substrate chemicals. The method is extremely easy and convenient to perform, and, unlike other approaches, the method and device do not require skilled personnel and cumbersome equipment.

In other preferred embodiments, the present invention involves the use of instruments such as the Biolog MICROSTATION, an instrument system that allows the reading of testing panels inoculated with cells, and analyzes the data obtained from the testing panels. This allows the rapid analysis of multiple phenotypic characteristics for many cell types (e.g., microbial strains) in a short time.

Bac Testing of the Present Invention

The present invention also provides multitest panels, referred to herein as "PHENOTYPE MICROARRAYS," or "PMs," to improve the effectiveness, throughput, and efficiency of testing and commercial development of biologically active compounds (BACs), in particular those useful in human, animal, and plant health.

Although particularly preferred embodiments of the present invention involve BACs such as antimicrobials and other compounds commonly used to treat disease or disease symptoms, the present invention also encompasses a wide range of BACs, including but not limited to drugs, nutrients, hormones, growth stimulating compounds, nutritional supplements, vitamins, metabolism-modifying compounds, insecticides, rodenticides, fungicides, herbicides, algicides, etc. It is further intended that the present invention encompasses BACs from any source. Thus, the present invention provides means to assess BACs from any source, as well as for any suitable application.

As indicated above, major problems are associated with traditional methods utilized in drug discovery and development. For example, a major problem remains, in that the drug developer must sort through drug candidates to find the promising ones and then sort through the promising drug candidates to see how they effect other aspects of cell function, as well as how they interact with other drugs that may be used simultaneously. The present invention provides methods to test this efficiently and effectively, since PMs provide cost-effective and rapid, physiologically-based analyses of in vivo drug activity.

In addition to aiding the testing of chemical libraries in an efficient, high-throughput manner, the present invention also finds use in detailed toxicological analyses. For example, it is contemplated that in assays utilizing mammalian cells, a battery of cell lines representing various organs are used to assay multiple drug candidates in an easy-to-use, high-throughput, rapid, and cost-effective manner. Based on these results, compounds that initially look promising, but that in fact cause unacceptable side effects can be eliminated from consideration before the start of costly clinical trials.

Importantly, the present invention also provides methods for the analysis of drugs used in combination. The advantages of this embodiment include the ability to assess the likely interaction of multiple drugs in vivo. For example, in some cases, drug combinations exert harmful or antagonistic interactions, while in other cases, drug combinations act synergistically to provide additional benefit to the patient. Examples of the latter include combinations such as sulfa drugs with trimethoprim, and penicillins with β-lactamase inhibitors.

As cost is always a consideration in the development of drugs and treatment regimens, the present invention provides distinct advantages over presently used methods. The present invention represents a significant time and cost savings for the development of drugs. For example, current estimates indicate that it takes an average of 14.9 years to develop a drug from first synthesis to final Food and Drug Administration (FDA) approval (See, R. Hansen, University of Rochester; S. N. Wigging, Texas A&M University; J. A. Dimasi, Tufts University Office of Technology Assessment, in *Healthcare Marketplace Guide Research Reports* 2000, 15th edition, volume 1, Dorland's Biomedical, Philadelphia, Pa. 19102, [1999-2000], at page I-172). The cost of developing a single new drug has been reported to have grown from $54 million in 1976 to the current average of $359 million (Hansen supra). In addition, billions of dollars are wasted because approximately nine out of ten drugs fail during the course of clinical trials (Hansen, supra). The ability to efficiently identify and characterize new drug candidates, as well as eliminate unsatisfactory candidates early in the drug discovery process can save pharmaceutical companies billions of dollars on an annual basis.

The present invention also provides methods and compositions suitable for determining the mode of action of a BAC of interest. In this embodiment, the invention utilizes PMs in broad assays of various cell functions. This allows the determination of which functions are most sensitively altered by the BAC. For example, if a BAC is shown to inhibit cell wall synthesis (e.g., vancomycin), the level of synergy between this test BAC and other BACs that also inhibit cell wall synthesis (e.g., cephalosporins, penicillins, etc.) can be easily and efficiently evaluated. The present invention can be used to make quantitative and qualitative determination(s) regarding the type and level of synergy between the BACs. In another example, the activity of BACs that inhibit enzymatic activity involved in biosynthesis of an amino acid such as isoleucine (e.g., sulfometuron methyl) may be observed (i.e., expected to be toxic) on minimal medium phenotypes, and the effect specifically reversed in phenotype media containing branch chain amino acids.

The present invention also finds use in determinations of the type and number of BAC targets present in cells. Such determinations are significant, in that preferred BACs have specific modes of action and no side effects. Each potential new BAC must satisfy a number of criteria prior to its approval for use.

The choice of a target is an important early step in the development of new BACs. In general, a target should provide adequate selectivity and spectrum (i.e., an antimicrobial will be highly specific and/or highly selective against the microbe with respect to the human host, and also be active against the desired pathogen spectrum); a target should be essential for the growth or viability of pathogens (i.e., at least under conditions of infection); and the function of the target should be known, so that assays and high throughput tests, such as those of the present invention can be utilized. The present invention also provides means to determine and assess the selectivity and spectrum of BACs, as well as the functionality, and degree of importance of various targets.

In some embodiments of the present invention, the activity of the BAC is determined in such a manner that side effects, such as an interaction with multiple targets, are observed. For example, in one test BAC 1 is a specific drug that inhibits one target, protein 1. This is distinguished from BAC 2, which is found to be a non-specific drug that inhibits protein 1, as well as protein 5. In the case where inhibition of protein 5 would be deleterious, this BAC would be determined to be unsuitable for use.

Figure 6:
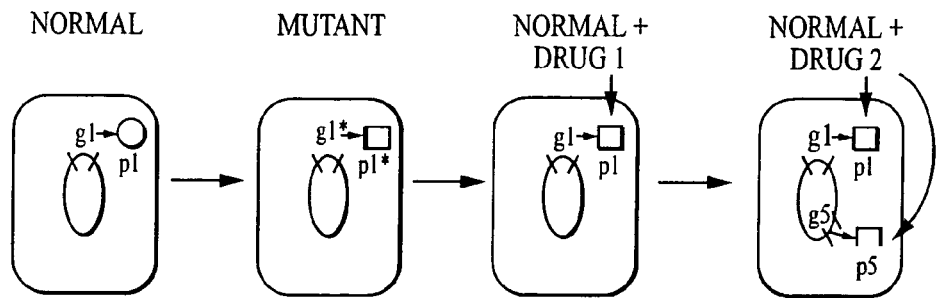
FIG. 6 provides a simple schematic of one embodiment of the present invention in which a drug target in a cell is inactivated by the addition of a drug to the cell. This testing is performed using PHENOTYPE MICROARRAY (PM) testing panels.
Figure 7:
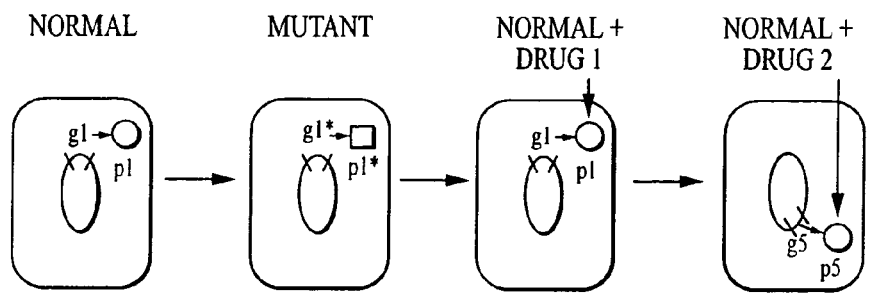
FIG. 7 provides a simple schematic of one embodiment of the present invention in which synergistic and antagonistic drug interactions are detected and characterized. This testing is also performed using PMs.

FIG. 6 provides a simplified schematic of one embodiment of the present invention designed to measure the effects of BACs on cells, using PMs. In this Figure and in FIG. 7, the "phe" designations indicate phenotypes of the cells (e.g., the growth and/or respiration of the cells in a particular well of the PHENOTYPE MICROARRAY). At the top left, FIGS. 6 and 7 show a normal cell and a mutant cell (e.g., a gene knockout), which lacks the functional activity of a normally encoded protein, which in this example, is a potential drug target. In FIGS. 6 and 7, "g1" indicates the gene that codes for protein "p1," which is the potential drug target. Most drugs work by blocking the activity of a protein, so when a drug is added, the cell now lacks the function of the target protein. Thus, in either case (i.e., the mutant cell or a normal cell exposed to a drug), the cell lacks the function of the target protein (e.g., p1). The major difference between these cells is that in the case of the mutant cell the protein function was eliminated by genetic means, whereas in the case of the normal cell exposed to the drug, the protein function was eliminated by chemical means. In FIG. 6, drug 1 is a good candidate for inactivating its target protein (p1), because it is active and specific (i.e., it only effects phenotype 1). In contrast, drug 2 is a poor candidate because it inactivates another protein, designated as protein 5 (p5), as well as p1 (i.e., it affects both phenotypes 1 and 5). Because drug 2 has non-specific effects on the cell, drug 2 is likely to cause side effects and be a less desirable compound to use in treatment regimens.

Thus, in some embodiments of the present invention, the activity of the BAC is determined in such a manner that side effects, such as an interaction with multiple targets, are observed. For example, in one test BAC 1 is a specific drug that inhibits one target, protein 1. This is distinguished from BAC 2, which is found to be a non-specific drug that inhibits protein 1, as well as protein 5. In the case where inhibition of protein 5 would be deleterious, this BAC would be determined to be unsuitable for use.

FIG. 7 provides a simplified schematic of how PMs can detect drug interactions. When a cell is simultaneously exposed to "drug 1" and "drug 2," the consequent effect is more than just the effect of drug 1 (i.e., phe 1 changed) and drug 2 (i.e., phe 5 changed), as phe 6 and phe 7 were also changed. This demonstrates an extra effect of the drugs that cannot be predicted based on the known effects of the drugs used singly. These extra effects (i.e., changes on phe 6 and phe 7) may be beneficial (i.e., synergistic) or they may be harmful (i.e., antagonistic).

Figure 8:
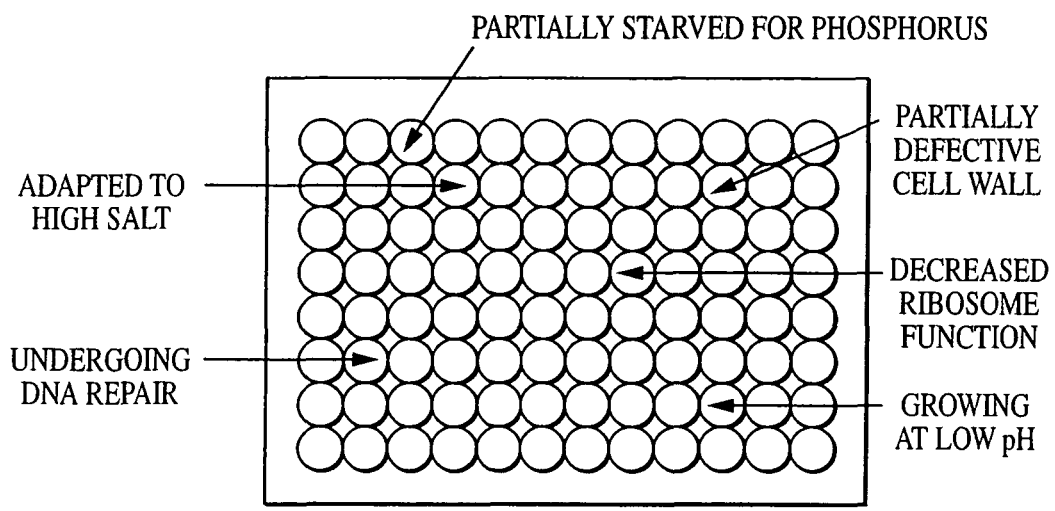
FIG. 8 provides a simplified schematic of the environmental conditions in various wells within a microtiter plate and the effect of these conditions on the cells within the wells.

As shown schematically in FIG. 8, during the testing process, the cells in various wells are placed under different environmental stresses. These stresses pressure the cells to adapt in order to survive. For example, in some wells, the cells may be partially starved for an element such as phosphorus, while in other wells the cells may be adapting to high salt conditions, undergoing DNA repair, growing at low pH, producing partially defective cell walls, or experiencing decreased ribosome function. Thus, the present invention provides means, starting from a single culture (or cell population), to expose that culture to various environmental conditions, and thereby create an array of cells in different physiological states. If an antimicrobial drug or other BAC is also added to the culture, the present invention provides means to simultaneously observe the effect of the BAC on the culture under many environmental and physiological conditions. This is very different and much more powerful than current practice for tasks such as determining the antimicrobial susceptibility patterns of organisms, which typically grow the culture only under one condition that provides for rapid growth of the organism (i.e., optimal growth conditions).

In traditional and current methods for antimicrobial susceptibility testing, every effort is made to standardize the procedure and its interpretation. Although the methods are relatively simple (e.g., Kirby-Bauer disk diffusion and tube dilution methods), they are strictly controlled in the clinical setting by the National Committee for Clinical Laboratory Standards (NCCLS) (See, Hindler, "Antimicrobial Susceptibility Testing," in Isenberg (ed.), *Clinical Microbiology Procedures Handbook*, vol. 1, American Society for Microbiology, Washington, D.C., [1994], pages 5.0.1 through 5.25.1). Indeed, the practitioner is warned to not deviate from the standard methods or misleading results may be obtained.

However, although antimicrobial susceptibility tests are one of the most important tasks of the clinical microbiology laboratory, it is recognized that these tests simply provide an in vitro prediction of how well a particular antimicrobial will work to treat a patient's disease (See, Jorgensen and Sahm, "Antimicrobial Susceptibility Testing: General Considerations, in Murray et al., (eds.) *Manual of Clinical Microbiology*, 6th edition, American Society for Microbiology, Washington, D.C. [1995], pages 1277-1280). Because the approved testing procedures are highly standardized, there is no mechanism for testing the susceptibility of organisms under different environmental stresses. This is in direct contrast to the present invention, which allows the determination of antimicrobial susceptibility (as well as the determination of other characteristics of a particular culture) under multiple and widely different conditions, such as those that the organisms may encounter in vivo.

Thus, as indicated above, the present invention further finds use in the determination of synergy and antagonism. As is known in the art, it is important to know which BAC combinations are synergistic and which are antagonistic or harmful when utilized. The present invention provides methods and compositions for determining these relationships.

The results obtained using the present invention can produce simple or complex patterns, which may be recorded quantitatively, and analyzed using standard methods known in the art. In particular, multidimenstional pattern analysis methods, including but not limited to non-metric multidimensional scaling (NMDS), principle component and canonical variate analysis, heuristic clustering analysis, distance and similarity matrix generation, data extraction and mining activities, and bioinformatics tools and practices. In methods such as ANOVA, sample sets are compared based on how closely they have the same degree of variability. ANCOVA provides information about the joint variability of data sets. It is also contemplated that principle component analysis (PCA) and canonical variate analysis (CVA) will find use in the present invention. PCA provides an algebraic analysis of the data matrix, while CVA is applied to the distance or similarity matrix associated with the same algebraic analysis of the data. Correspondence analysis and discriminate analysis provide methods to use the basic PCA algorithm. As with CVA, the difference is how the data are handled prior to application of the algorithm. Monte Carlo permutation tests are also contemplated for use in conjunction with the present invention. These tests provide an indication of the stability and reliability of cluster analysis results.

In addition, it is contemplated that use of the Gini coefficient will be used in analyzing data obtained using the present invention (See e.g., Harch et al., J. Microbiol. Meth., 30:91-101 [1997]). For example, in this analysis, the Gini coefficient can be used as a measure to quantify unequal use of certain substrates or BACs. However, the choice of statistical methods will depend upon the use of the present invention. Thus, it is not intended that the present invention be limited to any particular method for data analysis. Indeed, it is contemplated that methods such as the Shannon index, as well as other suitable approaches will be used to analyze data generated using the present invention (See also, Garland, FEMS Microbiol. Ecol., 24:289-300 [1997]).

In addition, the present invention provides methods for determining data on BAC susceptibility profiles and permitting their easy storage in a database. In preferred embodiments, the present invention is suitable for the comparative phenotype testing of microorganisms as well as other cells.

Optimization of Methods for Use with Suspensions of Animal Cells

The methods of the present invention developed for testing of bacterial and fungal cells have been revised to optimize them for testing animal cells. Importantly, the bacterial/fungal cell methods of the present invention are accomplished in a one-phase assay with a single incubation step. In contrast, the animal cells methods are accomplished in a two-phase assay with an adapting or pre-incubating step, in addition to the standard incubation step with a redox dye present. The adapting or pre-incubating step is done to reduce background, presumably by allowing the cells to deplete the suspension medium of any preferred or extraneous substrates (e.g., glucose or other nutrients from serum, excess amino acids from basal RPMI or DMEM media, etc.). This helps to insure that color development (e.g., indicator of respiration) occurs primarily in response to metabolism of the testing substrates. The length of time required for adaptation can be determined for a given animal cell suspension by measuring color development in the presence and absence of a testing substrate (e.g., glucose positive control and no substrate negative control). The inventors contemplate that the length of the requisite pre-incubation or adaptation period depends upon: (1) the concentration of the extraneous substrates, (2) the number of cells per well, and (3) the metabolic rate of the cells. Preferred adaptation periods are those resulting in little to no color in the negative control well and measurable levels of color in the positive control well (e.g., ideal adaptation periods are those resulting in the largest differences in color between the two control wells). In addition, suitable suspension media for use with animal cells can comprise some utilizable substrates (e.g., extraneous substrates such as those found in serum and/or low levels of free amino acids typically found in animal cell culture media), whereas suspension media for use with bacterial or fungal cells should not contain any significant levels of utilizable substrates.

Representative Testing Devices for Use with Suspensions of Animal Cells

In some embodiments of the present invention a testing device comprising a plurality of testing substrates is provided. In some preferred embodiments, the plurality of testing substrates comprise several of: Glycogen, D-Cellobiose, 3-0-beta-D-Galacto-pyranosyl-D-Arabinose, Gentiobiose, alpha-D-Glucose, D-Glucose-6-Phosphate, alpha-D-Lactose, Maltose, D-Mannose, Melibionic Acid, alpha-Methyl-D-Mannoside, D-Tagatose, D-Trehalose, Turanose, Inosine, Uridine, Thymidine, N-Acetyl-Neuraminic Acid, Chondroitin Sulfate C, D-Galactonic Acid-g-Lactone, L-Galactonic Acid-g-Lactone, D-Galacturonic Acid, D-Gluconic Acid, gamma-Amino Butyric Acid, alpha-Hydroxy Glutaric Acid-g-Lactone, a-Keto-Glutaric Acid, D-Lactic Acid Methyl Ester, L-Lactic Acid, L-Malic Acid, Propionic Acid, Pyruvic Acid, Succinamic Acid, Succinic Acid, Succinic Acid Monomethyl Ester, D-Ribono-1,4-Lactone, Tricarballylic Acid, L-Alaninamide, L-Alanine, L-Arginine, L-Asparagine, L-Aspartic Acid, L-Glutamic Acid, L-Glutamine, L-Histidine, L-Leucine, L-Ornithine, L-Phenylalanine, L-Proline, L-Serine, L-Threonine, D-Serine, D-Threonine, D-Ala-D-Ala, Ala-Ala, Ala-Trp, Arg-Arg, Arg-Trp, Gln-Gln, Gln-Glu, Gln-Gly, Ala-Gln, Arg-Gin, Asp-Gln, Ile-Gln, Met-Gln, Pro-Gln, Ser-Gln, Thr-Gln, Tyr-Gln, Val-Gln, Glu-Asp, Glu-Trp, Gly-Gly, Gly-Trp, His-His, His-Trp, Leu-Leu, Leu-Trp, Lys-Ile, Lys-Trp, Met-Met, Met-Trp, Trp-Asp, Phe-Trp, Pro-Ile, Pro-Trp, Ser-Ala, Thr-Ala, Thr-Ser, Trp-Trp, Trp-Val, and Tyr-Ala.

In other embodiments, the plurality of testing substrates comprise several of: alpha-Cyclodextrin, Sodium hexanoate, Dextrin, Tween 20, Glycogen (oyster), Tween 40, Maltitol, Tween 80, Maltotriose, Gelatin (porcine skin) Type A, D-(+)-Maltose monohydrate, Sodium 4-hydroxybenzoate, alpha-Trehalose Dihydrate, 4-Hydroxyphenylacetic acid, D-(+) Cellobiose, (±)-Octopamine, beta-Gentiobiose, 2-Phenyl-ethylamine, L-Glucose, Tryptamine, D-(+)-Glucose, Tyramine, Cys-Gly, Phe-Ala, Gly-Cys, Phe-Asp, Gly-Ala, Phe-Glu, Gly-Arg, Phe-Gly, Gly-Asn, Phe-Ile, Gly-Asp, Phe-Met, Gly-Gly, Phe-Phe, Gly-His, Phe-Pro, Gly-Ile, Phe-Ser, Gly-Leu, Phe-Trp, Gly-Lys.HCl, Phe-Tyr, D-Glucose-6-phosphate, L-Alaninamide, alpha-D-Glucose 1-phosphate hydrate, L-Alanine, 3-O-Methyl-D-glucopyranose, D-Alanine, Methyl alpha-D-glucoside, L-Arginine, Methyl beta-D-glucoside, L-Asparagine, D-(−)-Salicin, L-Aspartic acid monohydrate, D-Sorbitol, D-Aspartic Acid, N-Acetyl-D-glucosaminitol, L-Glutamic acid hydrate, N-Acetyl-D-glucosamine, D-Glutamic Acid, D-(+)-Glucosamine, L-Glutamine, D-Glucosaminic acid, Glycine HCl, D-Gluconic acid, L-Histidine, Gly-Met, Phe-Val, Gly-Phe, Pro-Ala, Gly-Pro, Pro-Arg, Gly-Ser, Pro-Asn, Gly-Thr, Pro-Asp, Gly-Trp, Pro-Glu, Gly-Tyr, Pro-Gln, Gly-Val, Pro-Gly, His-Ala, Pro-Hyp, His-Asp, Pro-Ile, His-Glu, Pro-Leu, His-Gly, Pro-Lys, D-Glucuronic acid, L-Homoserine, Chondroitin 6-sulfate, trans-4-Hydroxy-L-Proline, Mannan, L-Isoleucine, D-Mannose, L-Leucine, Methyl alpha-D-Mannopyranoside, L-Lysine, D-Mannitol, L-Methionine, N-Acetyl-D-mannosamine, L-Ornithine HCL, D-(+)-Melezitose monohydrate, L-Phenylalanine, Sucrose, L-Proline, Palatinose, L-Serine, D-(+)-Turanose, D-Serine, D-Tagatose, L-Threonine, His-His, Pro-Phe, His-Leu, Pro-Pro, HCl, His-Lys-HBr, Pro-Ser, His-Met, Pro-Trp, His-Pro, Pro-Tyr, His-Ser, Pro-Val, His-Trp, Ser-Ala, His-Tyr, Ser-Asn, His-Val, Ser-Asp, Ile-Ala, Ser-Glu, Ile-Arg, Ser-Gln, Ile-Asn, Ser-Gly, L-(−)-Sorbose, D-Threonine, L-Rhamnose monohydrate, L-Tryptophan, L-Fucose, L-Tyrosine, D-Fucose, L-Valine, Fructose, Ala-Ala, D-Fructose 6-phosphate dihydrate, Ala-Arg, Stachyose, Ala-Asn, D-(+)-Raffinose pentahydrate, Ala-Asp, D-Lactitol monohydrate, Ala-Glu, Lactulose, Ala-Gln, Lactose monohydrate, Ala-Gly, Melibionic Acid, Ala-His, Ile-Gin, Ser-His, Ile-Gly, Ser-Leu, Ile-His, Ser-Met, Ile-Ile, Ser-Phe, Ile-Leu, Ser-Pro, Ile-Met, Ser-Ser, Ile-Phe, Ser-Tyr, Ile-Pro, Ser-Val, Ile-Ser, Thr-Ala, Ile-Trp, Thr-Arg, Ile-Tyr, Thr-Asp, Ile-Val, Thr-Glu, D-Melibiose, Ala-Ile, D-Galactose, Ala-Leu, Methyl alpha-D-galactopyranoside, Ala-Lys·HCl, Methyl-beta-D-galactopyranoside, Ala-Met, N-Acetyl-neuraminic acid, Ala-Phe, Pectin (apple), Ala-Pro, Sedoheptulose anhydride monohydrate, Ala-Ser, Thymidine, Ala-Thr, Uridine, Ala-Trp, Adenosine, Ala-Tyr, Inosine, Ala-Val, D-Ribose, Arg-Ala, Leu-Ala, Thr-Gln, Leu-Arg, Thr-Gly, Leu-Asn, Thr-Leu, Leu-Asp, Thr-Met, Leu-Glu, Thr-Phe, Leu-Gly, Thr-Pro, HCl, Leu-His, Thr-Ser, Leu-Ile, Trp-Ala, Leu-Leu, Trp-Arg-, Leu-Met, Trp-Asp, Leu-Phe, Trp-Glu, Leu-Pro·-HCl, Trp-Gly, Ribitol, Arg-Arg, L-Arabinose, Arg-Asp, D-Arabinose, Arg-Gin, D-Xylose, Arg-Glu, Methyl beta-D-Xylopyranoside, Arg-Ile, Xylitol, Arg-Leu, myo-Inositol, Arg-Lys, meso-Erythritol, Arg-Met, Propylene glycol, Arg-Phe, Ethanolamine, Arg-Ser, Glycerol, Arg-Trp, rac-Glycerol 3-phosphate, Arg-Tyr, Leu-Ser, Trp-Leu, Leu-Trp, Trp-Lys, Leu-Tyr, Trp-Phe, Leu-Val, Trp-Ser, Lys-Ala, Trp-Trp, Lys-Arg, Trp-Tyr, Lys-Asp, Trp-Val, Lys-Glu, Tyr-Ala, Lys-Gly·-HCl, Tyr-Gln, Lys-Ile, Tyr-Glu, Lys-Leu, Tyr-Gly, Lys-Lys·2 HCl, Tyr-His, Citric acid, Arg-Val, Tricarballylic Acid, Asn-Glu, Sodium DL-lactate 60% (w/w) Syrup, Asn-Val, Methyl D-lactate, Asp-Ala, Methyl pyruvate, Asp-Asp, Pyruvate, Asp-Glu, 2-oxoglutarate, Asp-Gln, Succinamic acid, Asp-Gly, succinate, Asp-Leu, mono-Methyl hydrogen succinate, Asp-Lys, L-(−)-Malic acid, Asp-Phe, D-(+)-Malic acid, Asp-Trp, Lys-Met, Tyr-Ile, Lys-Phe.HCl, Tyr-Leu, Lys-Pro, Tyr-Lys, Lys-Ser, Tyr-Phe, Lys-Thr, Tyr-Trp, Lys-Trp, Tyr-Tyr, Lys-Tyr, Tyr-Val, Lys-Val, Val-Ala, Met-Arg, Val-Arg, Met-Asp, Val-Asn, Met-Gln, Val-Asp, Met-Glu, Val-Glu, meso-Tartaric acid, Asp-Val, acetoacetate, Glu-Ala, gamma-Amino-N-butyric acid, Glu-Asp, Sodium 2-oxobutyrate, Glu-Glu, Sodium 2-hydroxybutyrate, Glu-Gly, DL-beta-Hydroxybutyric acid, Glu-Ser, 4-Hydroxybutyric acid, Glu-Trp, Sodium butyrate, Glu-Tyr, 2,3-Butanediol, Glu-Val, 3-Hydroxy 2-Butanone, Gln-Glu, Propionic acid, Gln-Gln, Sodium acetate, Gln-Gly, Met-Gly, Val-Gln, Met-His, Val-Gly, Met-Ile, Val-His, Met-Leu, Val-Ile, Met-Lys, Val-Leu·HCl, Met-Met, Val-Lys, Met-Phe, Val-Met, Met-Pro, HCl, Val-Phe, Met-Thr, Val-Pro, Met-Trp, Val-Ser, Met-Tyr, Val-Tyr, Met-Val, and Val-Val.

Definitions

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, as well as solid tissue. These terms also refers to swabs and other sampling devices, which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

Whether biological or environmental, a sample suspected of containing plant or animal cells may (or may not) first be subjected to an enrichment means to create a "pure culture" of plant or animal cells. By "enrichment means" or "enrichment treatment," the present invention contemplates (i) conventional techniques for isolating a particular plant or animal cell of interest away from other plant or animal cells by means of liquid, solid, semi-solid or any other culture medium and/or technique, and (ii) novel techniques for isolating particular plant or animal cells away from other plant or animal cells. It is not intended that the present invention be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be analyzed by the medium and method of the present invention.

As used herein, the term "culture" refers to any sample or specimen, which is suspected of containing one or more plant or animal cells. In particularly preferred embodiments, the term is used in reference to bacteria and fungi. "Pure cultures" are cultures in which the organisms present are only of one strain of a particular genus and species. This is in contrast to "mixed cultures," which are cultures in which more than one genus and/or species of plant or animal cells are present.

As used herein, the term "eukaryote" refers to cells or organisms that have a unit membrane-bound (i.e., true) nucleus and usually have other organelles. Most eukaryotes have DNA that is complexed with histones and present in several chromosomes. The eukaryotes include algae, fungi, protozoa, plants, and animals. It is not intended that the present invention be limited to any particular eukaryotic cell or organism. Indeed, it is intended that the term encompass any organism or cell that has the characteristics typically associated with eukaryotic cells (See e.g., Brock et al., (eds), *Biology of Microorganisms,* 7th ed., Prentice Hall, N.J. [1994], at pages 86-87).

As used herein, the term "prokaryote" refers to organisms or cells that lack a unit membrane-bound (i.e., true) nucleus and other organelles (e.g., there is no nucleolus), and typically have a genome comprised of a single circular DNA. In most cases, cell walls are present. The prokaryotes include bacteria (i.e., eubacteria) and archaea (i.e., archaebacteria). It is not intended that the present invention be limited to any particular prokaryotic cell or organism. Indeed, it is intended that the term encompass any organism or cell that has the characteristics typically associated with prokaryotic cells (See e.g., Brock et al., (eds), *Biology of Microorganisms,* 7th ed., Prentice Hall, N.J. [1994], at pages 86-87).

As used herein, the term "organism" is used to refer to any species or type of microorganism, including but not limited to bacteria, yeasts and other fungi. As used herein, the term fungi, is used in reference to eukaryotic organisms such as the molds and yeasts, including dimorphic fungi.

As used herein, the term "spore" refers to any form of reproductive elements produced asexually (e.g., conidia) or sexually by such organisms as bacteria, fungi, algae, protozoa, etc. It is also used in reference to structures within microorganisms such as members of the genus *Bacillus,* which provide advantages to the individual cells in terms of survival under harsh environmental conditions. It is not intended that the term be limited to any particular type or location of spores, such as "endospores" or "exospores." Rather, the term is used in the very broadest sense.

As used herein, the terms "microbiological media" and "microbiological culture media," and "media" refer to any substrate for the growth and reproduction of microorganisms. "Media" may be used in reference to solid plated media, which support the growth of microorganisms. Also included within this definition are semi-solid and liquid microbial growth systems including those that incorporate living host organisms, as well as any type of media.

As used herein, the terms "culture media," and "cell culture media," refers to media that are suitable to support the growth of cells in vitro (i.e., cell cultures). It is not intended that the term be limited to any particular cell culture medium. For example, it is intended that the definition encompass outgrowth as well as maintenance media. Indeed, it is intended that the term encompass any culture medium suitable for the growth of the cell cultures of interest.

As used herein, the term "basal medium," refers to a medium, which provides nutrients for the microorganisms or cells, but does not contain sufficient concentrations of substrates to support growth of microorganisms or cells. In some embodiments, basal medium does not contain sufficient carbon compounds to trigger a color response from the indicator.

As used herein, the term "suspension media" refers to media that are suitable for dispersing cell samples, and which contain extraneous substrates that can be utilized by the cells. In some preferred embodiments, the "suspension medium" comprises RPMI 1640 formulated with reduced glutamine (0.3 mM), and without glucose and phenol red. In other preferred embodiments, the "suspension medium" comprises Dulbecco's Modified Eagle Medium (DMEM) formulated with reduced glutamine (0.3 mM), and without glucose, sodium pyruvate, riboflavin and phenol red. In some preferred embodiments, the suspension medium further comprises from 1-25% serum.

As used herein, the term "extraneous substrates" refers to substrates contained within the suspension medium (as opposed to the testing substrates provided in the testing devices of the present invention). In some embodiments, the extraneous substrates are from a serum supplement to the suspension media.

As used herein, the term "serum" refers to the fluid portion of the blood obtained after removal of the fibrin clot and blood cells. The term encompasses but is not limited to bovine serum, horse serum, chicken serum, goat serum, lamb serum porcine serum and rabbit serum. The serum can be obtained from fetal, newborn, or juvenile animals. In some preferred embodiments, the serum is heat inactivated.

As used herein, the term "defined medium" refers to a medium in which the components are known. For example, the term encompasses synthetic media prepared using particular ingredients of known composition. However, it is not intended that the present invention be limited to any particular medium or type of medium. In addition, the present invention encompasses defined media with additional uncharacterized components (i.e., the defined medium is the basal medium to which various compounds are added). In contrast to defined media, "undefined media" are media that contain uncharacterized or unknown constituents (e.g., trypticase soy broth, yeast extract, serum, plasma, etc.).

As used herein, the term "cell type," refers to any cell, regardless of its source or characteristics.

As used herein, the term "cell line," refers to cells that are cultured in vitro, including primary cell lines, finite cell lines, continuous cell lines, and transformed cell lines.

As used herein, the terms "primary cell culture," and "primary culture," refer to cell cultures that have been directly obtained from animal, plant or insect tissue. These cultures may be derived from adults, as well as fetal tissue.

As used herein, the term "finite cell lines," refer to cell cultures that are capable of a limited number of population doublings prior to senescence.

As used herein, the term "continuous cell lines," refer to cell cultures that have an indefinite lifespan. Some cell lines arise from spontaneous transformation, while others are engineered (e.g., by telomerization).

As used herein, the term "transformed cell lines," refers to cell cultures that have been transformed into continuous cell lines with the characteristics as described above. Transformed cell lines can be derived directly from tumor tissue and also by in vitro transformation of cells with whole virus (e.g., SV40 or EBV), or DNA fragments derived from a transforming virus using vector systems.

As used herein, the terms "monolayer," "monolayer culture," and "monolayer cell culture," refer to cells that have adhered to a substrate and grow as a layer that is one cell in thickness. Monolayers may be grown in any format, including but not limited to flasks, tubes, coverslips (e.g., shell vials), roller bottles, microplates, etc. Cells may also be grown attached to microcarriers, including but not limited to beads.

As used herein, the term "confluent" refers to adherent cells that are in contact with each other, such that there is no substrate that is uncovered by cells.

As used herein, the term "adherent" refers to cells that are "anchorage-dependent" (i.e., require attachment to a solid substrate or surface for survival and/or growth), and are attached to a solid substrate. In contrast, "anchorage-independent" cells do not require attachment to a solid substrate or surface for survival and/or growth.

As used herein, the term "contact inhibition" refers to the inhibition of cell membrane ruffling and cell motility when cells are in complete contact with other adjacent cells (e.g., in a confluent culture). This stage often precedes cessation of cell proliferation, but the two are not necessarily causally related.

As used herein, the term "suspension," and "suspension culture," refers to cells that survive and proliferate without being attached to a substrate. Suspension cultures are typically produced using hematopoietic cells, transformed cell lines, and cells from malignant tumors.

The term "transferable matrix" as used herein, refers to any material suitable for attachment of cells for ease in conveying the cells from one place to another. The term "transferable matrix" encompasses both natural and synthetic materials. Preferred "transferable matrices" include microcarrier beads, although other types of structures such as disks may also be used in different embodiments of this invention.

As used herein, the term "microcarrier beads" refer to beads that are suitable for cell attachment and growth. These beads are commercially available and are commonly used for the growth and maintenance of cells in culture. In particularly preferred embodiments, cells are grown attached to beads placed in liquid growth medium. Thus, in some embodiments, cells are grown in suspension but are attached to microcarrier beads.

As used herein, the term "mixed cell culture," refers to a mixture of at least two types of cells. In some embodiments, the cells are cell lines that are not genetically engineered, while in other preferred embodiments the cells are genetically engineered cell lines.

As used herein, the term "hybridomas," refers to cells produced by fusing at least two cell types together. Commonly used hybridomas include those created by the fusion of antibody-secreting B cells from an immunized animal, with a malignant myeloma cell line capable of indefinite growth in vitro. These cells are commonly cloned and used to prepare monoclonal antibodies.

As used herein, the term "carbon source" is used in reference to any carbon-containing compound, which may be utilized for cell growth and/or metabolism including compounds that can be oxidized to stimulate cell respiration. Carbon sources may be in various forms, including, but not limited to polymers, carbohydrates, acids, alcohols, aldehydes, ketones, amino acids, and peptides. Carbon sources may be in various forms, including, but not limited to polymers, carbohydrates, acids, alcohols, aldehydes, ketones, amino acids, and peptides.

As used herein, the term "nitrogen source" is used in reference to any nitrogen-containing compound, which may be utilized for cell growth and/or metabolism. As with carbon sources, nitrogen sources may be in various forms, such as free nitrogen, as well as compounds which contain nitrogen, including but not limited to amino acids, peptones, vitamins, and nitrogenous salts.

As used herein, the term "sulfur source" is used in reference to any sulfur-containing compound, which may be utilized as a source of sulfur for cell growth and/or metabolism. As with carbon and nitrogen sources, sulfur sources may be in various forms, such as free sulfur, as well as compounds that contain sulfur.

As used herein, the term "phosphorus source" is used in reference to any phosphorus-containing compound, which may be utilized as a source of phosphorus for cell growth and/or metabolism. As with carbon, nitrogen, and sulfur sources, phosphorus sources may be in various forms, such as free phosphorus, as well as compounds, which contain phosphorus.

The terms "biologically active chemical," "biologically active compound" and the acronym "BAC" refer to compounds, which modulate cell metabolism (e.g., increased or decreased respiration rate), cell growth and/or proliferation (e.g., alteration in cell size and/or cell numbers), and/or cell phenotype (e.g., gene expression and/or degree of differentiation). Major categories of BACs, which find use with this invention include, but are not limited to antimicrobials (e.g., antibiotics, antivirals, fungicides, insecticides, etc.) and pharmaceuticals (e.g., small molecules, recombinant proteins, hormones, cytokines, lectins, mitogens, etc.).

As used herein, the term "auxotroph" is used in reference to an organism that can be grown only in the presence of nutritional supplements (e.g., growth factors). Thus, in auxotrophic testing, auxotrophs will only grow in the presence of the supplement(s) that is/are necessary for their growth, and will not grow in media that lack the necessary supplement(s).

As used herein, the term "drug" refers to any compound that has biological activity. In some embodiments, the term is used in reference to antimicrobials, although it is not intended that the term be limited to antimicrobials. Indeed, the term encompasses pharmaceuticals and other compounds that alter cell proliferation, metabolism, and/or growth, as well as compounds that affect microbial and/or other cells (e.g., animal cells, plant cells, etc.) Thus, the term encompasses such compounds as anti-inflammatories, anti-histaminics, emetics, anti-emetics, and other compounds that cause some effect in biological systems and/or cells.

As used herein, the term "antimicrobial" is used in reference to any compound, which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorganisms.

As used herein, the term "testing substrate" is used in reference to any nutrient source (e.g., carbon, nitrogen, sulfur, phosphorus sources) that may be utilized to differentiate cells based on biochemical characteristics. For example, one species may utilize one testing substrate that is not utilized by another species. This utilization may then be used to differentiate between these two species. It is contemplated that numerous testing substrates be utilized in combination. Testing substrates may be tested individually (e.g., one substrate per testing well or compartment, or testing area) or in combination (e.g., multiple testing substrates mixed together and provided as a "cocktail").

Following exposure to a testing substrate such as a carbon or nitrogen source (or any other nutrient source), or an antimicrobial, the response of cell may be detected. This detection may be visual (i.e., by eye) or accomplished with the assistance of machine(s) (e.g., the Biolog MICROSTATION Reader). For example, the response of organisms to carbon sources may be detected as turbidity in the suspension due to the utilization of the testing substrate by the organisms. Likewise, growth can be used as an indicator that an organism is not inhibited by certain BACs. In one embodiment, color is used to indicate the presence or absence of organism growth/metabolism.

As used herein, the term "time release composition" refers to any material suitable for release of a substrate, biologically active chemical or a calorimetric indicator over time (e.g., by dissolution of a coating or a protective layer), as contrasted from immediate release of a substrate, biologically active chemical or colorimetric indicator. "Time release compositions" appropriate for use include but are not limited to those materials used to coat pharmaceutical compounds for gradual release in the gastrointestinal tract. Preferred embodiments of the invention utilize a time release composition such as agar, agarose, gellan gum, arabic gum, xanthan gum, carageenan, alginate salts, bentonite, ficoll, pluronic polyols, CARBOPOL, polyvinylpyrollidone, polyvinyl alcohol, polyethylene glycol, methyl cellulose, hydroxymethyl cellulose, hydroxyethyl cellulose, carboxymethyl cellulose, carboxymethyl chitosan, chitosan, poly-2-hydroxyethyl-methacrylate, polylactic acid, polyglycolic acid, collagen, gelatin, glycinin, sodium silicate, silicone oil, or silicone rubber, although the invention is not limited to the use of these compounds.

As used herein, the terms "chromogenic compound" and "chromogenic substrate," refer to any compound useful in detection systems by their light absorption or emission characteristics. The term is intended to encompass any enzymatic cleavage products, soluble (as well as insoluble), which are detectable either visually or with optical machinery. Included within the designation "chromogenic" are all enzymatic substrates, which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator" encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator" and "oxidation-reduction indicator" encompass all compounds commonly used for detection of oxidation/reduction potentials (i.e., "eH") including, but not limited to various types or forms of tetrazolium, resazurin, methylene blue, and quinone-imide redox dyes including the compounds known as "methyl purple" and derivatives of methyl purple. The quinone-imide redox dye known as methyl purple is referred to herein as "redox purple." In a particularly preferred embodiment, "redox purple" comprises the compound with the chemical structure shown in FIG. 5, VI. It is contemplated that analogous derivatives of the reagent (e.g., alkali salts, alkyl O-esters), with modified properties (e.g., solubility, cell permeability, toxicity, and/or modified color(s)/absorption wavelengths) will be produced using slight modifications of the methods described in Example 12. It is also contemplated that various forms of redox purple (e.g., salts, etc.), may be effectively used in combination as a redox indicator in the present invention.

As used herein, the terms "testing means" and "testing device" are used in reference to testing systems in which at least one organism is tested for at least one characteristic, such as utilization of a particular carbon source, nitrogen source, or chromogenic substrate, and/or susceptibility to a BAC. This definition is intended to encompass any suitable means to contain a reaction mixture, suspension, or test. It is intended that the term encompass microtiter plates, petri plates, miniaturized card devices, or any other supporting structure that is suitable for use. For example, a microtiter plate having at least one gel-initiating agent included in each of a plurality of wells or compartments, comprises a testing means. Other examples of testing means include microtiter plates without gel-initiating means included in the well. It is also intended that other compounds such as carbon sources or BACs will be included within the compartments. The definition encompasses the MICROPLATE testing plates (Biolog) for characterization of cells. The definition is also intended to encompass miniaturized plates or cards which are similar in function, but much smaller than standard microtiter plates (for example, many testing devices can be conveniently held in a user's hand). In particularly preferred embodiments, the microcards are the MICROCARD miniaturized testing cards described in U.S. Pat. Nos. 5,589,350, and 5,800,785, both of which are herein incorporated by reference (available from Biolog). It is not intended that the present invention be limited to a particular size or configuration of testing device or testing means. For example, it is contemplated that various formats will be used with the present invention, including, but not limited to microtiter plates (including but not limited to MICROPLATE testing plates), miniaturized testing plates (e.g., MICROCARD miniaturized testing cards), petri plates, petri plates with internal dividers used to separate different media placed within the plate, test tubes, as well as many other formats.

As used herein, the term "gelling agent" is used in a broad generic sense, and includes compounds that are obtained from natural sources, as well as those that are prepared synthetically. As used herein, the term refers to any substance, which becomes at least partially solidified when certain conditions are met. For example, one gelling agent encompassed within this definition is GELRITE, a gellan that forms a gel upon exposure to divalent cations (e.g., $Mg^{2+}$ or $Ca^{2+}$). GELRITE is a gellan gum, produced by deacetylating a natural polysaccharide produced by *Pseudomonas elodea*, and is described by Kang et al. (U.S. Pat. Nos. 4,326,052 and 4,326,053, herein incorporated by reference).

Included within the definition are various gelling agents obtained from natural sources, including protein-based as well as carbohydrate-based gelling agents. One example is bacteriological agar, a polysaccharide complex extracted from kelp. Also included within the definition are such compounds as gelatins (e.g., water-soluble mixtures of high molecular weight proteins obtained from collagen), pectin (e.g., polysaccharides obtained from plants), carrageenans and alginic acids (e.g., polysaccharides obtained from seaweed), and gums (e.g., mucilaginous excretions from some plants and bacteria). It is contemplated that various carrageenan preparations will be used in the present invention, with iota carrageenan comprising a preferred embodiment. It is also contemplated that gelling agents used in the present invention may be obtained commercially from a supply company, such as Difco, BBL, Oxoid, Marcor, Sigma, or any other source.

It is not intended that the term "gelling agent" be limited to compounds that result in the formation of a hard gel substance. A spectrum is contemplated, ranging from merely a more thickened or viscous colloidal suspension to one that is a firm gel. It is also not intended that the present invention be limited to the time it takes for the suspension to gel.

Importantly, it is intended that in some embodiments, the present invention provides a gelling agent suitable for production of a matrix in which organisms including, but not limited to, plant or animal cells may grow (i.e., a "gel matrix"). The gel matrix of the present invention is a colloidal-type suspension of organisms produced when organisms are mixed with an aqueous solution containing a gelling agent, and this suspension is exposed to a gel-initiating agent. It is intended that this colloidal-type gel suspension be a continuous matrix medium throughout which organisms may be evenly dispersed without settling out of the matrix due to the influence of gravity. The gel matrix must support the growth of organisms within, under, and on top of the gel suspension.

As used herein the term "gel-initiating agent" refers to any compound or element that results in the formation of a gel matrix, following exposure of a gelling agent to certain conditions or reagents. It is intended that "gel-initiating agent" encompass such reagents as cations (e.g., $Ca^{2+}$, $Mg^{2+}$, and $K^+$). Until the gelling agent contacts at least one gel-initiating agent, any suspension containing the gelling agent remains "ungelled" (i.e., there is no thickening, increased viscosity, nor hardening of the suspension). After contact, the suspension will become more viscous and may or may not form a rigid gel (i.e., contact will produce "gelling").

As used herein, the term "inoculating suspension" or "inoculant" is used in reference to a suspension, which may be inoculated with organisms to be tested. It is not intended that the term "inoculating suspension" be limited to a particular fluid or liquid substance. For example, inoculating suspensions may be comprised of water, saline, or an aqueous solution that includes at least one gelling agent. It is also contemplated that an inoculating suspension may include a component to which water, saline or any aqueous material is added. It is contemplated in one embodiment, that the component comprises at least one component useful for the intended cells. It is not intended that the present invention be limited to a particular component.

As used herein, the term "kit" is used in reference to a combination of reagents and other materials. It is contemplated that the kit may include reagents such as carbon sources, nitrogen sources, chromogenic substrates, antimicrobials, diluents and other aqueous solutions, as well as specialized microplates (e.g., GN, GP, ES, YT, SF—N, SF—P, and other MICROPLATES testing plates, obtained from Biolog), inoculants, miniaturized testing cards (e.g., MICROCARDS), and plated agar media. The present invention contemplates other reagents useful for the growth, identification and/or determination of the antimicrobial susceptibility of microorganisms. For example, the kit may include reagents for detecting the growth of cells following inoculation of kit components (e.g., tetrazolium or resazurin included in some embodiments of the present invention). It is not intended that the term "kit" be limited to a particular combination of reagents and/or other materials. Further, in contrast to methods and kits that involve inoculating organisms on or into a preformed matrix such as an agar surface or broth, the present invention involves inoculation of a testing plate in which the organisms are suspended within a gel-forming matrix.

As used herein, the term "primary isolation" refers to the process of culturing organisms directly from a sample. Thus, primary isolation involves such processes as inoculating an agar plate from a culture swab, urine sample, environmental sample, etc. Primary isolation may be accomplished using solid or semi-solid agar media, or in liquid. As used herein, the term "isolation" refers to any cultivation of organisms, whether it be primary isolation or any subsequent cultivation, including "passage" or "transfer" of stock cultures of organisms for maintenance and/or use.

Although embodiments have been described with some particularity, many modifications and variations of the preferred embodiment are possible without deviating from the invention.

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply: optical density (OD); eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); TSA (trypticase soy agar); YME or YEME (Yeast extract-malt extract agar); EMB (eosin methylene blue medium); MacConkey (MacConkey medium); Redigel (RCR Scientific, Goshen, Ind.); GELRITE (Merck and Co., Rahway, N.J.); PES (phenazine ethosulfate); PMS (phenazine methosulfate); Invitrogen (Invitrogen Corporation, Carlsbad, Calif.); Remel (Remel, Lenexa, Kans.); Oxoid (Oxoid, Basingstoke, England); BBL (Becton Dickinson Microbiology Systems, Cockeysville, Md.); DIFCO (Difco Laboratories, Detroit, Mich., now part of Becton-Dickinson); Acumedia (Acumedia, Baltimore, Md.); U.S. Biochemical (U.S. Biochemical Corp., Cleveland, Ohio); Fisher (Fisher Scientific, Pittsburgh, Pa.); Sigma (Sigma Chemical Co., St. Louis, Mo.); Life Technologies (Life Technologies, Rockville, Md.); Biolog (Biolog, Inc., Hayward, Calif.); ATCC (American Type Culture Collection, Rockville, Md.); CBS (Centraalbureau Voor Schimmelcultures, Delft, Netherlands); CCUG (Culture Collection of University of Gothenberg, Gothenberg, Sweden); GSU (Georgia State University, Atlanta, Ga.); NRRL (USDA Northern Regional Research Laboratory, Peoria, Ill.); and NCYC (National Collection of Yeast Cultures, Norwich, England); DMEM (Dulbecco's Modified Eagle's Medium); HBSS (Hank's Balanced Salt Solution); NCCLS (National Committee for Clinical Laboratory Standards); API (API Analytab Products, Plainview, N.Y.); Flow (Flow Laboratories, McLean, Va.); bioMerieux (bioMerieux, Hazelwood, Mo.); Trek (Trek Diagnostic Systems, Inc., Westlake, Ohio); Dojindo (Dojindo Molecular Technologies, Inc., Gaithersburg, Md.); and Molecular Devices (Molecular Devices, Mountain View, Calif.). The three-letter abbreviations conventionally used for amino acids (e.g., "ala" designates alanine or an alanine residue) are also used in some of the following Examples.

The following Tables list the principal bacterial strains used in some of the following Examples, with Table 3 listing the various actinomycetes, and Table 4 listing other species of microorganisms.

TABLE 3

Actinomycetes Tested

| Organism | Source and Number |
| --- | --- |
| *Actinomadura ferruginea* | USDA NRRL B-16096 |
| *Actinoplanes rectilineatus* | USDA NRRL B-16090 |
| *Micromonospora chalcea* | USDA NRRL B-2344 |
| *Norcardiopsis dassonvillei* | USDA NRRL B-5397 |
| *Saccharopolyspora hirsuta* | USDA NRRL B-5792 |
| *Streptomyces albidoflavus* | USDA NRRL B-1271 |
| *Streptomyces coeruleoribidus* | USDA NRRL B-2569 |
| *Streptomyces griseus* | USDA NRRL B-2682 |
| *Streptomyces hygroscopicus* | USDA NRRL B-1477 |
| *Streptomyces lavendulae* | USDA NRRL B-1230 |
| *Streptoverticillium salmonis* | USDA NRRL B-1484 |

TABLE 4

Other Organisms Tested

| Organism | Source and Number |
| --- | --- |
| *Escherichia coli* | ATCC#25922 |
| *Staphylococcus aureus* | ATCC#29213 |
| *Providencia stuartii* | ATCC#33672 |
| *Pseudomonas cepacia* | ATCC#25416 |
| *Neisseria lactamica* | CCUG#796 |
| *Xanthomonas maltophilia* | ATCC#13637 |
| *Vibrio metschnikovii* | ATCC#7708 |
| *Cedecea neteri* | ATCC#18763 |
| *Rhodococcus equi* | ATCC#6939 |
| *Dipodascus ovetensis* | ATCC#10678 |
| *Cryptococcus laurentii* | CBS#139 |
| *Cryptococcus terreus* A | CBS#1895 |
| *Kluyveromyces marxianus* | GSU#C90006070 |
| *Saccharomyces cerevisiae* A | NCYC##505 |
| *Williopsis saturnus* var. *saturnus* | GSU#WC-37 |
| *Penicillium notatum* | ATCC#9179 |
| *Penicillium chrysogenum* | ATCC#11710 |
| *Rhizomucor pusillus* | ATCC#32627 |
| *Aspergillus niger* | ATCC#16404 |
| *Tricophyton mentagrophytes* | ATCC#9129 |

Example 1

Primary Growth of Actinomycetes

In this Example, several attempts to grow various actinomycetes in R2A liquid media prepared from the recipe of Reasoner and Geldreich (Reasoner and Geldreich, Appl. Environ. Microbiol., 49:1-7 [1985]), prior to preparation of inoculum suspensions for inoculating commercially available MICROPLATES testing plates (e.g., Biolog's GN, GP, and YT MICROPLATES) are described. This method proved unsuccessful and cumbersome. Also, it was virtually impossible to obtain uniform (homogenous) cultures of satisfactory quality.

Next, these organisms were grown on the surface of various agar media. It was thought this might provide a very simple means to harvest spores from the culture, as the colonies tend to anchor into the agar matrix itself. The media used in this example included Sporulation Agar (described by R. Atlas in Handbook of Microbiological Media, CRC Press, Boca Raton, Fla., p. 834 [1993]), and YEME Agar with glucose omitted (described by E. B. Shirling and D. Gottlieb, in "Methods for Characterization of *Streptomyces* Species," Int'l J. System. Bacteriol., 16:313-330 [1966])(hereinafter referred to as YEMEWG).

Sporulation Agar (also known as m-Sporulation Agar) comprises agar (15 g/l), glucose (10 g/l), tryptose (2 g/l), yeast extract (1 g/l), beef extract (1 g/l), and $FeSO_4 \cdot 7H_2O$ (1 µg/l), pH 7.2±0.2 at 25° C. These ingredients are added to 1 liter of distilled/deionized water, and mixed thoroughly with heat to boiling. After the mixture has dissolved, it is autoclaved at 15 psi (121° C.) for 15 minutes, and dispensed into plates.

YEMEWG Agar comprises Bacto yeast extract (4 g/l; Difco), and Bacto-malt extract (10 g/l; Difco). These ingredients are added to 1 liter of distilled/deionized water and mixed thoroughly. The pH is adjusted to 7.3, and agar (20 g/l) is added to the mixture. The mixture is then autoclaved at 121° C. for 15-20 minutes, and dispensed into Petri plates after it is sufficiently cooled. YEMEWG was used because preliminary studies indicated that, while glucose-containing YEME agar was adequate for growth of the *Streptomyces* species, genera such as *Nocardiopsis* and *Actinoplanes* grew better when glucose was omitted from the medium recipe.

Because of the interest in obtaining spores, media that encourage sporulation were tried. For example, YEMEWG was found to be particularly useful, as this medium gave satisfactory growth and sporulation of most strains tested within 2-4 days of incubation at 26° C. Various agar concentrations were tested during these preliminary studies, and it was further observed that when YEMEWG was used, improved sporulation occurred in the presence of a higher agar concentration (e.g., 25 g/l, rather than the 15 g/l, traditionally used in microbiological agar media).

This approach of growing actinomycetes on a sporulation-inducing medium would have the additional benefit of standardizing the physiological state of the organisms, and would permit preparation of inocula primarily from spheroidal spores. It was usually a relatively simple matter to produce uniform, homogeneous suspensions containing spores. Occasionally, however, large clumps of the organisms and their aerial mycelia are obtained which do not readily disperse in solution. When clumps are formed, the suspension is allowed to sit for a few minutes, permitting the large fragments to settle to the bottom of the tube. Use of a light inoculum (i.e., a 1:10 dilution of an initial suspension where the initial suspension has a transmittance level of 70%) also helps avoid problems with clumping of large fragments. Therefore, clumps can be avoided in the preparation of the final inoculum because only a small, clump-free aliquot of the initial suspension is used. For those organisms that sporulate poorly, fragments of rods and/or mycelial filaments were obtained from the agar surface in the same manner.

This example highlights the advantages of the present invention for the primary growth and subsequent characterization of actinomycetes, in contrast to references that indicate growth of actinomycetes is very slow. For example, Bergey's Manual (T. Cross, "Growth and Examination of Actinomycetes—Some Guidelines," in J. Holt et al., "The Actinomycetes," Bergey's Manual of Determinative Bacteriology, 9th ed., Williams & Wilkins, Baltimore, pp. 605-609 [1994]) indicates that "mature aerial mycelium with spores may take 7-14 days to develop, and some very slow-growing strains may require up to 1 month's incubation." This is in stark contrast to the present invention, in which heavy growth and sporulation is achieved within 2-4 days of incubation.

Example 2

Preparation of Inoculum

In this experiment, a method more optimal for preparation of a homogeneous inoculum was determined. For example, it was found that an easy and reproducible method to grow the organisms was as described in Example 1 on YEMEWG prepared with 25 g/l agar, or other suitable agar medium. A low density inoculum (i.e., 0.01 to 0.1 $OD_{590}$) was then prepared by moistening a cotton swab and rubbing it across the top of the colonies to harvest mycelia and spores. It was determined that sterilized water and 0.85% sterile saline worked reasonably well as a suspension medium for all strains. However, some strains exhibited a preference for one or the other. For example, Streptomyces coeruleoribidus, S. hygroscopicus, and S. albidoflavus produced an average of ten additional positive reactions when water was used as the suspension medium, whereas thirteen additional positive reactions were observed for S. lavendulae when saline was used as the suspension medium. The majority of the Actinomycetes performed better when water was used. Therefore, water was used routinely to prepare the suspensions.

Example 3

Preparation of Multi-Test Plates

The inocula prepared as described in Example 2 were used to inoculate various Biolog MICROPLATE testing plates, including the commercially available GN, GP, and YT MICROPLATE testing plates. A few strains worked well upon inoculation into the GN or GP MICROPLATE testing plates (e.g., S. lavendulae). However, for most strains (e.g., A. ferruginea, and N. dassonvillei) no positive reactions were observed. In addition, positive reactions were observed in all of the test wells for some organisms (e.g., S. hirsuta), indicating that there was a problem with false positive results.

Much improved results were obtained when the wells located in the bottom five rows of the YT MICROPLATE testing plate were used. It was thought that this observation was due to the absence of tetrazolium in these wells, as the tetrazolium present in the other wells appeared to inhibit the growth of the organisms. This was confirmed by testing the ability of the organisms to grow on YEMEWG agar media containing various concentrations of tetrazolium (20, 40, 60 and 80 mg/l). Many strains (e.g., S. coeruleoribidus, S. hygroscopicus, S. Iavendulae, M. chalcea, N. dassonvillei, and A. rectilineatus) were inhibited at all of these tetrazolium concentrations. Other organisms, such as S. griseus, S. albidoflavus, and S. hirsuta, were somewhat inhibited at the higher tetrazolium concentrations, but grew in tetrazolium concentrations of 20 and 40 mg/l.

Based on these experiments, MICROPLATE testing plates containing no tetrazolium (e.g., "SF—N" [GN MICROPLATE testing plate without tetrazolium], and "SF—P" [GP MICROPLATE testing plate without tetrazolium] MICROPLATE testing plate) were then tested. These plates were inoculated with water or saline suspensions of various actinomycetes, and incubated at 26° C. for 1-4 days. Increased turbidity (i.e., growth of the organisms) was readable visually, or with a microplate reader (e.g., a Biolog MICROSTATION Reader testing plate reader, commercially available from Biolog), in as little as 24 hours for some strains. For the slow growing strains, growth was readable and the results interpretable within 3-4 days, representing a significant improvement over the 7-10 day incubation period required using routine methods.

Example 4

Use of GELRITE

Although growth was observable in the multi-test system described in Example 3, the results were still not completely satisfactory, due to the unique growth characteristics of the actinomycetes. Many of these strains adhered to the plastic walls of the microplate wells, thereby making detection of increased turbidity less than optimal. When the inoculating suspension is a liquid, turbidity often was concentrated along the outer circumference of the wells, rather than producing a uniform dispersion of turbidity throughout the wells.

In order to facilitate uniform dispersion of the inoculating suspension throughout the well, a gelling agent was added to the suspension to prevent individual cells from migrating to the well walls. For example, preparations of GELRITE (commercially available from Sigma, under this name, as well as "Phytagel") were found to be highly satisfactory. GELRITE does not form a gel matrix until it is exposed to gel-initiating agents, in particular, positively charged ions such as divalent cations (e.g., $Mg^{2+}$ and $Ca^{2+}$). As soon as the GELRITE comes into contact with the salts present in the bottom of the microplate wells, the gelling reaction begins and results in the formation of a gel matrix within a few seconds.

Various concentrations of GELRITE were tested, including 0.1, 0.2, 0.3, 0.4, 0.5 and 0.6%. All concentrations gelled in the microplate, with the higher concentrations producing a harder gel.

In view of the fact that most of the actinomycetes are obligate aerobes, there was a concern that the oxygen concentration within the gel must be sufficient to permit growth. Thus, various gel depths were tested by using 50, 100, or 150 μl suspensions of organisms in the wells. Each of these depths resulted in good growth of organisms, although it was observed that 0.4% GELRITE and an inoculum of 100 μl produced optimal results, even with organisms such as Streptomyces lavendulae, a species that is strongly hydrophobic and clings to the walls of wells when it is suspended in water. The 0.4% concentration of GELRITE was found to produce an appropriate degree of viscosity to readily permit preparation of microbial suspensions and still be easily pipetted.

The entire procedure for growth and testing of the actinomycetes required a total of 3-7 days, including primary inoculation on YEMEWG medium and other suitable media to determination and analysis of the final results. Importantly, a minimum amount of personnel time was required (i.e., just the few minutes necessary to inoculate the primary growth medium and then prepare the suspension for biochemical testing). Thus, the present invention provides a much improved means for the rapid and reliable identification of actinomycetes.

Example 5

Comparison of Water and GELRITE

In this Example, the eleven actinomycetes listed in Table 3 were tested in both water and gel suspensions. For each organism, a water suspension of organisms with an optical transmittance of 70%, was diluted 1:10 in either water or 0.4% GELRITE. Thus, two samples of each organism were produced, one sample being a water suspension and one sample being a suspension which included GELRITE.

One hundred microliters of each sample were inoculated into SF—P MICROPLATES (GP MICROPLATE testing plates without tetrazolium; commercially available from Biolog). The MICROPLATE testing plates were incubated at 27° C. for 48 hours, and observed for growth. As shown in the table below, the number of positive reactions increased dramatically for the organisms suspended in GELRITE, as compared to water.

TABLE 5

Growth of Selected *Streptomyces* Species

|  | Number of Positive/ Borderline Reactions in Water Suspensions (+/b) | Number of Positive/ Borderline Reactions in Gel Suspensions (+/b) |
| --- | --- | --- |
| *Streptomyces coeruleorubidus* | 5/35 | 35/25 |
| *Streptomyces griseus* | 30/15 | 43/12 |
| *Streptomyces lavendulae* | 8/18 | 24/12 |

Example 6

Use of Resazurin

In this Example, three concentrations of resazurin dye (25 mg/l, 50 mg/l, and 75 mg/l) were used as a redox color indicator of organism growth and metabolism. All of the eleven actinomycete strains listed in Table 3 were tested using these three concentrations of resazurin, and 0.4% GELRITE.

The expected color reaction, a change from blue to pink and eventually to colorless, as the dye is progressively reduced, occurred with all test organisms after 48 hours of incubation at 27° C. This observation provides a supplemental indicator of organism metabolism in addition to turbidity. No single resazurin concentration provided uniformly optimal results. For example, *N. dassonvillei* produced a good differential pattern of color change at 25 mg/l and 50 mg/l, whereas *S. lavendulae* produced false positive results (i.e., all colorless wells) at the lower concentrations (25 mg/l and 50 mg/l), but a good differential pattern of color change at 75 mg/l.

Although the resazurin concentration may need to be adjusted depending upon the organism tested, the use of resazurin as a color indicator may provide additional valuable information to characterize organisms at the species or strain level.

In the course of these experiments, it was also observed that pigments produced by some actinomycetes in the various carbon sources tended to create very distinct and unique patterns. The unexpected observation was made that pigment production was enhanced by using a gel-forming substance in the inoculant.

Thus, different color patterns were obtained with the differing resazurin dye concentrations in combination with the natural pigments produced. For example, at 50 mg/l resazurin, *M. chalcea* produced a range of color intensities from colorless to light pink to bright pink and purple. *S. hygroscopicus* produced a range of colors from yellow and orange, to colorless, pink and blue. Other species exhibited other distinct color patterns in the wells. This additional information related to pigmentation and resazurin dye reduction, may be valuable to taxonomists and others interested in characterizing specific strains and/or species of actinomycetes.

Example 7

Use of Alternative Gelling Agents

Other gelling agents were tested in this Example. In addition to GELRITE, alginic acid, carrageenan type I, carrageenan type II, and pectin were tested for their suitability in the present invention. All of these compounds are commercially available from Sigma.

Of these compounds, pectin was found to be unsuitable when tested by adding 1% pectin to SF—P MICROPLATE testing plates. Pectin has a yellowish cast to it, and is therefore not a colorless or clear compound. Furthermore, gelling was dependent upon the presence of sugars in the microplate wells. Because many of the substrates tested in this multitest format do not contain sugars, gelling did not occur uniformly in all wells.

All of these gelling agents with the exception of pectin, were tested with the eleven actinomycetes listed in Table 3. The same MICROPLATE testing plates (SF—P), incubation time and temperature, as described in Example 5 above, were used. The only variables were the different gelling agents and varying concentrations of these agents.

The optimal viscosity and performance for each gelling agent was determined. Optimal viscosity and performance was achieved at 1% alginic acid; 0.2% was optimum for both types of carrageenan; and 0.4% was optimum for GELRITE. All of these gelling agents were also diluted to half the above concentrations and found to be useful even at these lower concentrations.

Overall, the results for GELRITE and carrageenan types I and II were similar, and the difference in gel concentration did not affect the results significantly. However, the results for alginic acid were not as clearcut when the MICROPLATE testing plates were observed by eye, as compared to the use of an automatic plate reader (e.g., Biolog MICROSTATION Reader, Biolog). Indeed, when read by eye, the results with alginic acid were somewhat inferior to those obtained with GELRITE. Carrageenan type II was slightly better than type I and it was also comparable to or better than GELRITE. Surprisingly, the carrageenan type II functions as effectively as the GELRITE, although the carrageenan does not form a rigid gel. This indicates that it is not necessary that a rigid gel be formed in order for the beneficial effects of these colloidal gelling agents to be observed.

Example 8

Testing of Other Bacterial Species

In addition to the actinomycetes, the present invention is also suitable for the rapid characterization of numerous and diverse organisms, such as those listed in Table 4. The gram-negative bacteria tested covered a range of genera and tribes, including *Pseudomonas cepacia, Providencia stuartii, Neisseria lactamica, Xanthomonas maltophilia, Vibrio metschnikovii, Cedecea neteri*, and *Escherichia coli*. Various gram-positive bacteria were also tested, including *Rhodococcus equi* and *Staphylococcus aureus*.

These organisms were tested basically as described in Example 5 above, with GN MICROPLATE testing plates (Biolog) used to test the gram-negative organisms, and GP MICROPLATE testing plates (Biolog) used to test the gram-positive organisms. In addition, ES MICROPLATE testing plates (Biolog) were also tested with some of the gram-negative species. Inoculation in 0.4% GELRITE was compared to inoculation in 0.85% saline. The inoculation densities used were those normally recommended for these MICROPLATE test kits (55% transmittance for the gram-negative organisms, and 40% for the gram-positive organisms). Following inoculation of the MICROPLATE test plates with 150 µl suspensions of organisms in either saline or GELRITE per well, the MICROPLATE testing plates were incubated at 35° C. for 16-24 hours.

All of these organisms performed well in the gel, with most producing better results in gel than in saline. For example, in the ES MICROPLATE testing plates, *E. coli* produced 43 positive reactions within 24 hours when the gel was used, but only 36 positive reactions when saline was used. A correct identification of *C. neteri* was obtained after only 4 hours of incubation in the GELRITE, whereas overnight incubation was required for saline. Thus, a correct identification of this organism is possible in a much shorter time period than the 24 hour incubation usually required for traditional testing methods.

In contrast to conventional biochemical testing materials and methods traditionally used, the present invention often achieves a definitive identification in a significantly shorter time period.

Example 9

Testing of Eukaryotic Microorganisms—Yeasts

This experiment was designed to determine the suitability of the present invention for use in identification of eukaryotic microorganisms, such as yeasts. In this experiment, two types of reactions were observed to establish a metabolic pattern: a) assimilation reaction tests which are based on turbidity increases due to carbon utilization by the organisms; and b) oxidation tests, which also test for carbon utilization, but which detect utilization via a redox color change of the organism suspension.

In this experiment, yeasts were first grown on BUY Agar (Biolog) a solid agar medium, and harvested from the agar surface as described in Example 2 above. The organisms included in this example are listed in Table 4 (*D. ovetensis, C. laurentii, C. terreus, K. marxianus, S. cerevisiae,* and *W. saturnus*). Biolog YT MICROPLATE testing plates (available commercially from Biolog) were then inoculated with an inoculum having an optical transmittance of 50%, in either water or 0.4% GELRITE. Each well of the YT MICROPLATE testing plate was inoculated with 100 µl of either the water or 0.4% GELRITE suspension of organisms. Thus, there were two sets of 6 MICROPLATE testing plates each. The inoculated MICROPLATE testing plates were incubated at 27° C., and the results observed at 24, 48, and 72 hours of incubation.

With the oxidation tests, in most cases, the color changes developed more rapidly in the plates with GELRITE used as the inoculant, compared to the plates with water as the inoculant. For example, *D. ovetensis, W saturnus, K marxianus,* and *C. laurentii* gave stronger reactions at 48 hours with GELRITE. In contrast, *S. cerevisiae* and *C. terreus* gave stronger reactions at 48 hours with water.

With the assimilation tests, in all cases the GELRITE was superior or equivalent to the water inoculant. The data shown in the Tables below clearly demonstrate that more positive (+) and borderline (b) reactions were obtained overall, when GELRITE was used.

TABLE 6

Positive (+) and Borderline (b) Reactions After One Day of Incubation

| Organism | Water (+/b) | GELRITE (+/b) |
|---|---|---|
| D. ovetensis | 0/5 | 17/7 |
| K. marxianus | 14/3 | 16/9 |
| W. saturnus | 9/7 | 40/9 |
| C. terreus A | 4/14 | 33/3 |
| C. laurentii | 61/5 | 67/8 |
| S. cerevisiae A | 24/5 | 22/2 |

TABLE 7

Positive (+) and Borderline (b) Reactions After Two Days of Incubation

| Organism | Water (+/b) | GELRITE (+/b) |
|---|---|---|
| D. ovetensis | 9/2 | 22/2 |
| K. marxianus | 14/5 | 39/4 |
| W. saturnus | 23/7 | 46/5 |
| C. terreus A | 21/7 | 45/4 |
| C. laurentii | 65/0 | 77/3 |
| S. cerevisiae A | 24/6 | 24/0 |

TABLE 8

Positive (+) and Borderline (b) Reactions After Three Days of Incubation

| Organism | Water (+/b) | GELRITE (+/b) |
|---|---|---|
| D. ovetensis | 21/9 | 23/7 |
| K. marxianus | 27/5 | 43/7 |
| W. saturnus | 48/6 | 52/3 |
| C. terreus A | 20/8 | 58/5 |
| C. laurentii | 68/6 | 78/5 |
| S. cerevisiae A | 24/8 | 24/2 |

In these experiments, the surprising observation was made that some organisms could be identified faster due to better growth (i.e., growth that appeared much more rapidly and at a greater density), in the plate with the GELRITE, as compared to the plate with water. For example, *Dipodascus ovetensis* developed a metabolic reaction pattern sufficient for correct identification after 24 hours of incubation in the GELRITE plate, while 48 hours of incubation was required to make the proper identification in the water plate.

In addition, many of the limitations and deficiencies of currently commercially available yeast identification systems, such as the Minitek (BBL), API 20 C (API), expanded Uni-Yeast-Tek System (Flow), and Vitek (Biomerieux) were overcome or avoided in the present example (see e.g., G. A. Land (ed.), "Mycology," in H. D. Isenberg (ed.), *Clinical Microbiology Procedures Handbook*, American Society for Microbiology, in particular "Commercial Yeast Identification Systems," pp. 6.10.1 through 6.10.5, [1994]). For example, in the Vitek system, heavily encapsulated yeasts and isolates with extensive mycelial growth are sometimes difficult to suspend. As indicated above, this limitation is avoided by the present invention, allowing for reliable and reproducible testing procedures and systems. In summary, GELRITE was shown to be clearly superior to water for the rapid identification of eukaryotic microorganisms.

Example 10

Testing of Eukaryotic Microorganisms—Molds

This experiment was designed to determine the suitability of the present invention for use in identification of eukaryotic microorganisms, such as molds.

In this experiment, the molds were first grown on modified Sabouraud-Dextrose agar (commercially available from various sources, including Difco). This medium is prepared by thoroughly mixing dextrose (20 g/l), agar (20 g/l), and neopeptone (1 g/l) in 1 liter of distilled/deionized water. Heat is applied, until the mixture boils. The medium is autoclaved for 15 minutes at 15 psi (121° C.). After cooling, the medium is distributed into petri plates.

The organisms included in this Example are listed in Table 4 (*P. notatum, P. chrysogenum, R. pusillus, A. niger* and *T. mentagrophytes*). After they were grown on Sabouraud-Glucose agar, an inoculum was prepared as described in Example 1. YT and SP—F MICROPLATE testing plates (Biolog) were then inoculated with a 1:10 dilution of a starting inoculum having an optical transmittance of 70%, in water, 0.2% carrageenan type II, or 0.4% GELRITE.

Each well of the SF—P MICROPLATE testing plates was inoculated with 100 µl of organisms suspended in either water, 0.2% carrageenan type II, or 0.4% GELRITE. For the YT plates, 100 µl of organisms suspended in either water, or 0.4% GELRITE were used to inoculate the wells. The inoculated MICROPLATE testing plates were incubated at 25° C., and the results observed by eye and by using a MICROSTATION Reader (Biolog) at 24 hour increments for a total of 4 days of incubation.

In nearly all cases, the turbidity changes developed more rapidly in the plates with carrageenan or GELRITE used as the inoculant, compared to the plates with water as the inoculant. The data shown in the Tables below clearly demonstrate that for most organisms, more positive (+) and borderline (b) reactions were obtained overall, when carrageenan or GELRITE was used, as compared to water. The results listed in these Tables were those observed with the MICROSTATION Reader (Biolog).

It was also observed that the improvement in the results using GELRITE or carrageenan as the gelling agent were sometimes more apparent when the test results were read visually, rather than by a machine (Biolog's MICROSTATION Reader). This was the case with *T. mentagrophytes*, where the improved results obtained with carrageenan were in fact, also obtained with GELRITE, although the reader did not detect this accurately at 72 hours. However, with longer incubation periods (e.g., 4-5 days), the visual and machine readings agreed very well in nearly all cases.

TABLE 9

Positive(+)/Borderline (b) Reactions
After 72 Hours of Incubation in SF-P MICROPLATE Testing Plates

| Organism | Carrageenan (+/b) | GELRITE (+/b) | Water (+/b) |
|---|---|---|---|
| P. notatum | 54/11 | 52/14 | 47/11 |
| P. chrysogenum | 56/13 | 54/11 | 50/17 |
| R. pusillus | 4/13 | 5/5 | 2/6 |
| A. niger | 23/17 | 29/12 | 17/10 |
| T. mentagrophytes | 16/12 | 3/6 | 5/1 |

TABLE 10

Positive(+)/Borderline(b) Reactions
After 72 Hours of Incubation in YT MICROPLATE Testing Plates

| Organism | GELRITE (+/b) | Water (+/b) |
|---|---|---|
| P. notatum | 78/5 | 67/4 |
| P. chrysogenum | 81/1 | 75/10 |
| R. pusillus | 17/22 | 13/26 |
| A. niger | 78/2 | 51/11 |
| T. mentagrophytes | 2/1 | 2/1 |

Example 11

Antimicrobial Susceptibility Testing

In this Example, the suitability of a gel matrix for use in antimicrobial susceptibility testing was investigated. Two organisms, *Staphylococcus aureus* (ATCC #29213) and *Escherichia coli* (ATCC#25922) were tested against a panel of three antimicrobial agents: ampicillin, kanamycin, and tetracycline. All three antimicrobials were obtained from Sigma. Biolog's MT MICROPLATE testing plates (Biolog), were used with 12.5 µl of a 10% glucose solution added to each well. Kanamycin and tetracycline were dissolved in sterile water. Ampicillin was dissolved in phosphate buffer (pH 8.0)(0.1 M/l $NaH_2PO_4 \cdot H_2O$). For each antimicrobial agent, a dilution series ranging from 0.25 µg/ml to 32 µg/ml final concentration, was prepared. A 15 µl aliquot of each dilution was pipetted into the wells of the MICROPLATE testing plates, with water used to dilute the kanamycin and tetracycline, and phosphate buffer (pH 6.0)(0.1 M/l $NaH_2PO_4 \cdot H_2O$) used to dilute the ampicillin. For each MICROPLATE testing plate, a row of eight wells without antimicrobials was used as a control. In the MT MICROPLATE testing plates, tetrazolium is included as a color indicator. Unlike the actinomycetes, the most commonly isolated gram-negative and gram-positive bacteria are not significantly inhibited by the presence of tetrazolium in these MICROPLATE testing plates.

In addition to the MT MICROPLATE testing plates, Biolog's SF—N MICROPLATE testing plates (GN MICROPLATE testing plates without tetrazolium), and SF—P MICROPLATE testing plates (GP MICROPLATE testing plates without tetrazolium) were tested (all of these plates were obtained from Biolog). *E. coli* was inoculated into the SF—N MICROPLATE testing plates, and *S. aureus* was inoculated into the SF—P MICROPLATE testing plates. In these MICROPLATE testing plates, 25 mg/l of resazurin was added as a color indicator as an alternative to tetrazolium. In addition, 12.5 µl of 10% glucose solution and 15 µl of each antimicrobial dilution were added to each well, as described in the paragraph above.

All of the wells in all of the MICROPLATE testing plates were inoculated with 100 µl of a very light suspension (e.g., a 1:100 dilution of a 55% transmittance suspension of *E. coli*, or a 1:100 dilution of a 40% transmittance suspension of *S. aureus*), and incubated overnight at 35° C.

For each organism and each MICROPLATE testing plates, 0.85% saline and 0.4% GELRITE were compared, by looking visually for the lowest antimicrobial concentration that inhibited dye (tetrazolium or resazurin) reduction. The minimum inhibitory concentration (MIC) for each organism was determined after 18 hours of incubation at 35° C. The MIC values for each organism, as determined from these experiments, are provided in the Tables below.

TABLE 11

MIC Determinations for *E. coli*
in MT MICROPLATE Testing Plates Containing Tetrazolium
and SF-N MICROPLATE Testing Plates Containing Resazurin

| | Antimicrobial | | |
|---|---|---|---|
| Diluent | Ampicillin | Kanamycin | Tetracycline |
| Saline | 1–2 | 16–32 | 0.5–1 |
| GELRITE | 2–4 | 8–16 | 0.5–1 |
| NCCLS Expected Result | 2–8 | 1–4 | 1–4 |

TABLE 12

MIC Determinations for *S. aureus*
in SF-P MICROPLATE Testing Plates Containing Resazurin

| | Antimicrobial | | |
|---|---|---|---|
| Diluent | Ampicillin | Kanamycin | Tetracycline |
| Saline | 1–4 | 16–32 | 0.25–2 |
| GELRITE | 1–2 | 16–32 | 0.25–1 |
| NCCLS Expected Results | 0.25–1 | 1–4 | 0.25–1 |

As shown in these tables, the results in the GELRITE agreed with the results obtained with saline as an inoculant within one two-fold dilution. This is considered satisfactory according to the National Committee on Clinical Laboratory Standards (NCCLS) guidelines (see e.g., J. Hindler (ed.), "Antimicrobial Susceptibility Testing," in H. D. Isenberg (ed.), *Clinical Microbiology Procedures Handbook*, American Society for Microbiology, pp. 5.0.1 through 5.25.1, [1994]). In one instance, the MIC was slightly lower in saline as compared to GELRITE. In three instances, the MIC's were slightly lower in GELRITE, than in saline. Thus, the present invention provides a novel and useful alternative method for determination of antimicrobial sensitivities of microorganisms. Another advantage of this invention is that the test may be conducted in a format that cannot be accidentally spilled.

Example 12

Synthesis of Redox Purple

In this Example, the redox indicator referred to as "Redox Purple" was synthesized for use in the present invention. In this Example, the method of Graan et al. (T. Graan, et al, "Methyl Purple, an Exceptionally Sensitive Monitor of Chloroplast Photosystem I Turnover: Physical Properties and Synthesis," Anal Biochem., 144:193-198 [1985]) was used with modifications. This synthesis is shown schematically in FIG. 5 and the Roman numerals (i.e., I, II, III, IV and V) used in this Example refer to those shown in FIG. 5. Unless otherwise indicated, the chemicals used in this Example were obtained from commercial sources such as Sigma.

Briefly, the benzoquinone-4-chloroimide (FIG. 5, II) was produced by dissolving 5 g 4-aminophenol (FIG. 5, I) in 1 N aqueous HCl (75 mL) (0° C.), followed by the addition of 200 mL sodium hypochlorite (NaClO, 5% w/v) to produce a chloroimide derivative shown in FIG. 5, Panel A. In this reaction, the solution was continuously stirred and the temperature maintained below 4° C. during addition of the sodium hypochlorite. After stirring at room temperature for 12 hours, the yellow to orange colored product was isolated by filtration, washed with cold distilled water and dried in air and in vacuo. In this step, the product was vacuum filtered using a Buchner funnel, washed with a minimal amount of ice-cold water (approximately 30 ml) in the funnel, dried in air for approximately 24 hours, and dried overnight in a vacuum desiccator.

The synthesis of 1-(3-hydroxyphenyl)-ethanol (FIG. 5, IV) was performed immediately prior to its use, by the reduction of 5 g 1-(3-hydroxyphenyl)-ethanone (available as m-hydroxyacetophenone from Tokyo Kasei Kogyo Co., Ltd. Fukaya, Japan, with TCI America, in Portland, Oreg., being the U.S. distributor) (FIG. 5, III) in water (300 mL) with sodium borohydride (NaBH$_4$, 1.5 g), as shown in FIG. 5, Panel B. The reaction was warmed as necessary to dissolve the starting material and stirred until the evolution of H$_2$ ceased (approximately 1 hour). The pH was decreased to 2.0 (i.e., with concentrated HCl) to remove excess borohydride, followed by addition of 150 ml saturated sodium borate.

The synthesis of redox purple was initiated by addition of the chloroimide derivative (II) to the freshly prepared solution of 1-(3-hydroxyphenyl)-ethanol (IV), in borate buffer (Na$_2$B$_4$O$_7$/H$_3$BO$_3$). Sodium arsenite (NaASO$_2$, 10 g) (Sigma) was added to the reaction solution, in order to promote the formation of the indophenol, as well as minimize the occurrence of side reactions. This reaction solution was stirred at room temperature for 2 hours, during which the blue color of the indophenol (FIG. 5, V) appeared. The reaction mixture was then allowed to sit at room temperature for 7-8 days, during which the closure of the heterocyclic ring was allowed to occur due to formation of an oxymethylene group bridge between the two phenolic residues of the quinoneimide. The ring closure was accompanied by a change in the solution color to a dark purple.

The reaction mixture was filtered and the precipitate washed with minimal cold water as described above. The filtrate was saturated with an excess of solid sodium chloride (approximately 100 g), the solution was decanted off the excess salt on the bottom of the container, and the solution extracted with diethylether (5×100 mL) until no more orange-colored material was removed from the aqueous phase. Vigorous shaking of the ether and aqueous phases was avoided, as this was found in some experiments to result in formation of an intractable emulsion. The combined ether layers were back-extracted with 70 mM aqueous sodium carbonate solution (25 mL), the pH of the sodium carbonate solution reduced to 4.5 with glacial acetic acid, and the resulting mixture refrigerated overnight at 4° C. The redox purple precipitated as the free acid. Additional redox purple was obtained by acidifying the original aqueous phases with glacial acetic acid (pH 4.5) and repeating the above purification. The total yield obtained by this synthesis method was approximately 25%.

The purity of the redox purple synthesized according to this method was 95-98%, as determined by thin-layer chromatography, a method that is well know in the art (A. Braithwaite and F. J. Smith, in "Chromatographic Methods" Chapman and Hall [eds.], London [1985], pp. 24-50.). It was found that the redox purple compound was not very soluble in water as the free acid, but was quite soluble in slightly basic solutions (e.g., 1 N NaHCO$_3$), or in organic solvents (e.g. methanol, ethanol, dimethyl sulfoxide [DMSO], dimethyl formamide [DMF], etc.). The compound was observed to be a deep purple color (i.e., of approximately 590 nm as an absorption wavelength) in basic solution and an orange-red color (470 nm) in acidic solution. It is contemplated that analogous derivatives of the reagent (e.g., alkali salts, alkyl O-esters), with modified properties (e.g., solubility, cell permeability, toxicity, and/or modified color(s)/absorption wavelengths)

will be produced using slight modifications of the methods described here. It is also contemplated that various forms of redox purple (e.g., salts, etc.), may be effectively used in combination as a redox indicator in the present invention.

Example 13

Redox Purple and E. coli Identification

In this Example, redox purple was used as the redox indicator in the test system. E. coli 287 (ATCC #11775) was cultured overnight at 35° C., on TSA medium supplemented with 5% sheep blood. A sterile, moistened, cotton swab was used to harvest colonies from the agar plate and prepare six identical suspensions of organisms in glass tubes containing 18 ml of 0.85% NaCl, or 0.2% carrageenan type II. The cell density was determined to be 53-59% transmittance. One saline and one carrageenan suspension were used to inoculate Biolog GN MICROPLATE testing plates, with 150 µl aliquots placed into each well. The wells of this plate contain tetrazolium violet as the redox indicator. Two ml of a 2 mM solution of redox purple (sodium salt)(prepared as described in Example 12), or two ml of a 2 mM solution of resazurin (sodium salt) were added to the other tubes, to produce a final dye concentration of 200 µM. These suspensions were used to inoculate Biolog SF—N MICROPLATE testing plates. As with the GN MICROPLATE testing plates, aliquots of 150 µl were added to each well in the plates. The SF—N MICROPLATE testing plates are identical to the GN MICROPLATE testing plates, with the exception being the omission of tetrazolium violet from the wells of the SF—N plates. The inoculated plates were incubated at 35° C. for approximately 16 hours. The plates were then observed and the colors of the well contents recorded.

For the 0.85% NaCl and 0.2% carrageenan suspensions inoculated into the SF—N MICROPLATE testing plate, positive results were obtained for all three redox indicators (i.e., redox purple, tetrazolium violet, and resazurin) in wells containing the following carbon sources: dextrin, tween-40, tween-80, N-acetyl-D-galactosamine, N-acetyl-D-glucosamine, L-arabinose, D-fructose, L-fucose, D-galactose, α-D-glucose, α-D-lactose, maltose, D-mannitol, D-mannose, D-melibiose, β-methyl-D-glucoside, L-rhamnose, D-sorbitol, D-trehalose, methyl pyruvate, mono-methyl succinate, acetic acid, D-galactonic acid lactone, D-galacturonic acid, D-gluconic acid, D-glucuronic acid, α-ketobutyric acid, D,L-lactic acid, propionic acid, succinic acid, bromosuccinic acid, alaninamide, D-alanine, L-alanine, L-alanyl-glycine, L-asparagine, L-aspartic acid, glycyl-L-aspartic acid, glycyl-L-glutamic acid, D-serine, L-serine, inosine, uridine, thymidine, glycerol, D,L-α-glycerol phosphate, glucose-1-phosphate, and glucose-6-phosphate.

For the 0.85% NaCl and 0.2% carrageenan suspensions, negative results were obtained for all three redox indicators (i.e., redox purple, tetrazolium violet, and resazurin) in wells containing the following carbon sources: α-cyclodextrin, adonitol, D-arabitol, cellobiose, i-erythritol, xylitol, citric acid, D-glucosaminic acid, β-hydroxybutyric acid, γ-hydroxybutyric acid, p-hydroxyphenylacetic acid, itaconic acid, α-ketovaleric acid, malonic acid, quinic acid, sebacic acid, L-histidine, hydroxy L-proline, L-leucine, and D,L-carnitine. The negative control wells containing water, instead of a carbon source were also negative for all three redox indicators.

For glycogen, D-psicose, succinamic acid, and glucuronamide, negative results were obtained with both the 0.85% NaCl and carrageenan suspensions with redox purple. However, positive results were obtained for both suspensions with tetrazolium violet and resazurin.

For gentiobiose, m-inositol, cis-aconitic acid, L-phenylalanine, L-pyroglutamic acid, phenylethylamine, putrescine, 2-amino ethanol, and 2,3-butanediol negative results were obtained with both the 0.85% NaCl and carrageenan suspensions with redox purple and tetrazolium violet. However, positive/negative results were obtained with the 0.2% carrageenan suspension in resazurin, while the resazurin result with the 0.85% NaCl was negative.

For lactulose, D-raffinose, formic acid, α-hydroxybutyric acid, L-glutamic acid, and L-proline, negative results were observed with the 0.85% NaCl suspension tested with redox purple, although the remaining results were positive.

For sucrose and L-ornithine, negative results were obtained for both the 0.85% NaCl and 0.2% carrageenan suspensions tested with redox purple and tetrazolium violet. However, a negative result was observed for the 0.85% NaCl suspension tested with resazurin and a positive result was observed for the 0.2% carrageenan suspension.

For turanose, both the 0.85% NaCl and 0.2% carrageenan suspensions were negative when tested with redox purple, while the results for both tested with tetrazolium violet were equivocal (±), the result for the 0.85% NaCl suspension tested with resazurin was also equivocal (±), and the result for the 0.2% carrageenan tested with resazurin was positive.

For α-ketoglutaric acid, negative results were observed for both the 0.85% NaCl and 0.2% carrageenan suspensions tested with redox purple and tetrazolium violet, while positive results were observed for both suspensions tested with resazurin.

For D-saccharic acid, negative results were observed for both the 0.85% and 0.2% carrageenan suspensions tested with redox purple, while the result with tetrazolium violet was equivocal (±) for 0.85% NaCl and negative for carrageenan, and the result with resazurin was negative for the 0.85% NaCl and positive for 0.2% carrageenan suspensions.

For L-threonine, equivocal (±) results were observed for 0.2% carrageenan suspensions tested with redox purple and tetrazolium violet, while the result with resazurin was positive. For the 0.85% NaCl suspension, the result was negative for redox purple, and positive for tetrazolium violet and resazurin.

For γ-aminobutyric acid and urocanic acid, negative results were observed for both the 0.85% NaCl and 0.2% carrageenan suspensions tested with redox purple and tetrazolium violet, while equivocal (±) results were observed with 0.85% NaCl, and positive results were observed with the 0.2% carrageenan.

In the inoculated GN MICROPLATE testing plate (containing tetrazolium violet), the wells corresponding to the carbon sources utilized by E. coli 287 became either a light or dark purple, while the wells corresponding to the carbon sources not utilized by this organism remained colorless. In contrast, in the inoculated SF-N MICROPLATE testing plate (containing redox purple), the color pattern was virtually reversed. For negative wells with redox purple, a blue to purple (i.e., blue-purple, purple-tinged blue, or violet) color was observed. In the SF—N MICROPLATE testing plate, the wells corresponding to carbon sources utilized by this organism were light blue or were colorless, while the wells containing carbon sources not utilized by this organism remained dark blue. The color patterns were easily read and analyzed. Thus, the redox purple was shown to work in a manner that appears to be equivalent to tetrazolium violet for detecting carbon source utilization by bacteria. However, there were three colors observed with the plates which included resazurin (i.e., blue, pink and colorless), making the redox purple a more useful redox indicator, as there was less ambiguity in the reading of the results.

The observation that none of the wells with redox purple was orange was very surprising, as the literature describing this compound indicated that there was an intermediate stage in the reduction of the dye which was expected to be reduced through the color progression of blue to orange to colorless. This two-stage reduction is in contrast to the typical reaction observed with resazurin, which gives blue, pink, and colorless wells when analyzed in a like manner. The side-by-side data for the resazurin in this experiment, as well as other tests, confirms that it does form three colors. The degree to which the results of the various plates were in agreement are shown in the following Table.

TABLE 13

Comparison of Redox Purple and Resazurin with Tetrazolium Violet

| Solution | Dyes Compared | Number of Wells With Same Result (96 Wells/Plate) | % Agreement |
|---|---|---|---|
| Saline | Redox Purple/ Tetrazolium Violet | 85/96 | 88.5 |
| Gel | Redox Purple/ Tetrazolium Violet | 92/96 | 95.8 |
| Saline | Resazurin/ Tetrazolium Violet | 95/96 | 99.0 |
| Gel | Resazurin/ Tetrazolium Violet | 91/96 | 94.8 |

The oxidized form of redox purple spectrally matches the reduced form of tetrazolium violet (i.e., with a maximum absorbance at 590 nm). This may provide an advantage, as detection methods such as spectrophotometry settings may be used interchangeably with tetrazolium violet and redox purple.

Example 14

Redox Purple and Identification of Fungi

In this Example, *Aspergillus niger*, *Penicillium chrysogenum*, and *Trichoderma harzianum* were tested using the redox purple indicator.

First, the above named organisms were tested using the GN MICROPLATE testing plate. However, none of these organisms reduced the tetrazolium violet in the wells of the plate. Thus, redox purple was investigated for use as an alternative dye.

*T harzianum* DAOM 190830 was cultured for seven days at 26° C. on malt extract agar (Difco). A sterile, moistened cotton swab was used to harvest conidia from the culture and prepare a suspension in 16 ml of 0.25% GELRITE. The cell density was determined to be 75% transmittance. A 2 ml aliquot of a 2 mM solution of redox purple was added to the suspension, along with 2 ml of 1 M triethanolamine-$SO_4$, pH 7.3. The final concentration of redox purple was 200 μM, and the final concentration of triethanolamine-$SO_4$ was 100 mM. The final suspension was mixed well and used to inoculate the wells of a Biolog SF—N MICROPLATE testing plate. In this Example, 100 μl of the suspension was added to each well. The inoculated SF—N MICROPLATE testing plate was incubated at 30° C. for approximately 24 hours, and observed.

For each carbon source utilized by the organism, the content of the wells was colorless. For each carbon source not utilized by the organism, the content of the wells was blue. In this Example, for this culture, positive results were obtained in the wells containing dextrin, glycogen, tween-40, tween-80, N-acetyl-D-glucosamine, L-arabinose, D-arabitol, cellobiose, i-erythritol, D-fructose, L-fucose, D-galactose, gentiobiose, α-D-glucose, D-mannitol, D-mannose, D-melibiose, β-methyl-D-glucoside, D-sorbitol, D-trehalose, methyl pyruvate, mono-methyl succinate, citric acid, D-galacturonic acid, β-hydroxybutyric acid, α-ketoglutaric acid, quinic acid, sebacic acid, succinic acid, bromo succinic acid, succinamic acid, L-alanine, L-alanyl-glycine, L-asparagine, L-glutamic acid, gylcyl-L-glutamic acid, L-ornithine, L-phenylalanine, L-proline, L-pyroglutamic acid, L-serine, γ-amino butyric acid, inosine, and glycerol.

Example 15

Phenotype Analysis of *E. coli*

In this Example, ten strains of *E. coli* were tested and compared in Biolog ES MICROPLATE testing plates and in Biolog MICROCARD miniaturized testing cards containing the same chemistry as the ES MICROPLATE testing plates. The strains tested in this Example are listed in the following Table. As indicated by the designation "H?" in this Table, the H antigen of some of the O157 strains is unknown.

TABLE 14

*E. coli* STRAINS

| Biolog Culture Number | Strain Name |
|---|---|
| 14443 | MG1655 (FB426) |
| 14444 | MG1655 xylA |
| 14445 | MG1655 himA |
| 6320 | W3110 |
| 6321 | MG1655 |
| 6322 | EMG2 (K12, λF$^+$) |
| 11547 | O157:H7 |
| 13671 | O157:H? gur+ |
| 13673 | O157:H? |
| 13675 | O157:H? |

All of the strains were cultured overnight on sheep blood agar plates (TSA with 5% sheep blood), at 35° C. Suspensions of the organisms were prepared for testing using either PPS (0.01% PHYTAGEl, 0.03% pluronic F-58, and 0.45% NaCl) for MICROPLATE plate testing, or IF1 (0.2% phytagel, 0.03% pluronic F-68, and 0.25% NaCl) for MICROCARD miniaturized card testing. All of the strains were tested in both MICROCARD miniaturized testing cards and MICROPLATES testing plates. For MICROPLATE plate testing, inocula were prepared in PPS at a density of 63% T (as measured in the Biolog turbidimeter), in 20×150 mm tubes. For MICROCARD miniaturized testing cards, inocula were prepared in IF1 at a density of 35% T (as measured in the Biolog turbidimeter) in 12×75 tubes. The inocula were dispensed into MICROPLATE test plates (150 μl/well) or MICROCARD miniaturized testing cards, as appropriate, and incubated at 35° C., for 24 hours. While results were obtained using both the MICROPLATE testing plates and MICROCARD miniaturized testing cards, the results were more consistent with MICROPLATES. Some wells in the MICROCARD miniaturized testing cards trapped air bubbles and gave false negative results. The MICROPLATE testing plates results are indicated in Table 15, below, as well as described further in the text following the Table. In Table 15, "+" indicates that the organism tested was capable of utilizing the carbon source listed, while "−" indicates that the organism tested was not capable of utilizing the carbon source listed, and "w" indicates weak positive reactions.

TABLE 15

Results for Ten E. coli Strains

| Well No. | Carbon Source | \multicolumn{10}{c}{E. coli Strain} |
| | | 14443 | 14444 | 14445 | 6320 | 6321 | 6322 | 11547 | 13671 | 13673 | 13675 |
|---|---|---|---|---|---|---|---|---|---|---|---|
| A1 | Water (control) | − | − | − | − | − | − | − | − | − | − |
| A2 | L-arabinose | + | + | + | + | + | + | + | + | + | + |
| A3 | N-acetyl-D-glucosamine | + | + | + | + | + | + | + | + | + | + |
| A4 | D-saccharic acid | + | + | + | + | + | + | − | − | − | − |
| A5 | Succinic acid | + | + | + | + | + | + | + | + | + | + |
| A6 | D-galactose | + | + | + | + | + | + | + | + | + | + |
| A7 | L-aspartic acid | + | + | + | − | + | + | + | + | + | + |
| A8 | L-proline | w | − | w | + | + | + | + | + | + | + |
| A9 | D-alanine | + | + | + | + | + | + | + | + | + | + |
| A10 | D-trehalose | + | + | + | + | + | + | + | + | + | + |
| A11 | D-mannose | + | + | + | + | + | + | + | + | + | + |
| A12 | Dulcitol | − | − | − | − | + | − | + | + | − | + |
| B1 | D-serine | + | + | + | + | + | + | w | − | w | w |
| B2 | D-sorbitol | + | + | + | + | + | + | − | − | − | − |
| B3 | Glycerol | − | − | − | + | + | + | + | + | + | + |
| B4 | L-fucose | + | + | + | + | + | + | + | + | + | + |
| B5 | D-glucuronic acid | + | + | + | + | + | + | + | + | + | + |
| B6 | D-gluconic acid | + | + | + | + | + | + | + | + | + | + |
| B7 | D,L-α-glycerol phosphate | − | − | − | − | + | + | + | + | + | + |
| B8 | D-xylose | + | − | + | + | + | + | + | + | + | + |
| B9 | L-lactic acid | + | + | + | + | + | + | + | + | + | + |
| B10 | Formic acid | + | + | + | + | + | + | + | + | − | + |
| B11 | D-mannitol | + | + | + | + | + | + | + | + | + | + |
| B12 | L-glutamic acid | + | − | − | − | − | w | − | + | + | + |
| C1 | Glucose-6-phosphate | + | + | + | + | + | + | + | + | + | + |
| C2 | D-galactonic acid-γ-lactone | + | + | + | − | + | + | − | − | − | − |
| C3 | D,L-malic acid | + | + | + | + | + | + | + | + | + | + |
| C4 | D-ribose | + | + | + | + | + | + | + | + | + | + |
| C5 | Tween-20 | − | − | − | − | w | w | w | w | w | w |
| C6 | L-rhamnose | + | + | + | + | + | + | + | + | + | w |
| C7 | D-fructose | + | + | + | + | + | + | + | + | + | + |
| C8 | Acetic acid | + | + | + | + | + | + | + | + | + | + |
| C9 | α-D-glucose | + | + | + | w | + | + | + | + | + | + |
| C10 | Maltose | + | − | − | + | + | + | + | + | + | + |
| C11 | D-melibiose | + | + | + | + | + | + | + | + | + | + |
| C12 | Thymidine | + | + | + | + | + | + | + | + | + | + |
| D1 | L-asparagine | + | + | + | − | + | + | + | + | + | + |
| D2 | D-aspartic acid | − | − | − | − | − | − | − | − | − | − |
| D3 | D-glucosaminic acid | − | − | − | − | − | − | − | − | − | − |
| D4 | 1,2-propanediol | − | − | − | − | − | − | − | − | − | − |
| D5 | Tween-40 | − | − | − | w | w | w | w | w | w | w |
| D6 | α-ketoglutaric acid | + | + | + | + | + | + | − | + | + | + |
| D7 | α-ketobutyric acid | + | + | − | + | + | − | w | − | − | − |
| D8 | α-methyl galactoside | + | + | + | + | + | + | + | + | + | + |
| D9 | α-D-lactose | + | + | + | + | + | + | + | + | + | + |
| D10 | Lactulose | − | − | − | − | − | + | + | + | + | + |
| D11 | Sucrose | − | − | − | − | − | − | − | + | + | + |
| D12 | Uridine | + | + | + | + | + | + | + | + | + | + |
| E1 | L-glutamine | + | + | + | − | − | + | + | + | + | + |
| E2 | M-tartaric acid | − | − | − | − | − | − | w | + | − | − |
| E3 | Glucose-1-phosphate | + | + | + | + | + | + | + | + | + | + |
| E4 | Fructose-6-phosphate | + | + | + | + | + | + | + | + | + | + |
| E5 | Tween-80 | − | − | − | w | + | w | w | w | w | w |
| E6 | α-hydroxy-glutaric acid γ-lactone | − | − | − | − | w | − | w | − | − | w |
| E7 | α-hydroxy butyric acid | + | + | − | + | + | + | w | w | w | w |
| E8 | β-methyl glucoside | + | + | + | + | + | + | + | + | + | + |
| E9 | Adonitol | − | − | − | − | − | − | − | − | − | − |
| E10 | Maltotriose | + | − | − | + | + | + | + | + | + | + |
| E11 | 2'-deoxy-adenosine | + | + | + | + | + | + | + | + | + | + |
| E12 | Adenosine | + | + | + | + | + | + | + | + | + | + |
| F1 | Glycyl-L-aspartic acid | + | + | + | + | + | + | + | + | + | + |
| F2 | Citric acid | − | − | − | − | − | − | − | − | − | − |
| F3 | M-inositol | − | − | − | − | − | − | − | − | − | − |
| F4 | D-threonine | − | − | − | − | − | − | − | − | − | − |

TABLE 15-continued

Results for Ten E. coli Strains

| Well No. | Carbon Source | E. coli Strain | | | | | | | | | |
|---|---|---|---|---|---|---|---|---|---|---|---|
| | | 14443 | 14444 | 14445 | 6320 | 6321 | 6322 | 11547 | 13671 | 13673 | 13675 |
| F5 | Fumaric acid | + | + | + | + | + | + | + | + | + | + |
| F6 | Bromo succinic acid | + | + | + | + | + | + | + | + | + | + |
| F7 | Propionic acid | + | + | − | + | + | + | + | + | + | + |
| F8 | Mucic acid | + | + | + | + | + | + | + | + | + | + |
| F9 | Glycolic acid | + | + | − | + | + | + | − | − | − | − |
| F10 | Glyoxylic acid | w | w | w | + | + | + | + | − | − | − |
| F11 | Cellobiose | − | − | − | − | − | − | − | − | − | − |
| F12 | Inosine | + | + | + | + | + | + | + | + | + | + |
| G1 | Glycyl-L-glutamic acid | + | + | + | + | + | + | + | + | + | + |
| G2 | Tricarballylic acid | − | − | − | − | − | − | − | − | − | − |
| G3 | L-serine | + | + | + | + | + | + | + | + | + | + |
| G4 | L-threonine | + | − | − | − | − | + | − | w | w | w |
| G5 | L-alanine | + | + | + | + | + | + | + | + | + | + |
| G6 | L-alanyl-glycine | + | + | + | + | + | + | + | + | + | + |
| G7 | Acetoactetic acid | − | − | − | w | − | − | − | − | − | − |
| G8 | N-acetyl-β-D-mannosamine | − | − | w | w | − | + | + | w | w | + |
| G9 | Mono-methyl succinate | + | + | + | + | + | + | + | + | + | + |
| G10 | Methyl pyruvate | + | + | + | + | + | + | + | + | + | + |
| G11 | D-malic acid | + | + | + | + | + | + | + | + | + | w |
| G12 | L-malic acid | + | + | + | + | + | + | + | + | + | + |
| H1 | Glycyl-L-proline | + | + | + | + | + | + | + | + | + | + |
| H2 | P-hydroxy phenylacetic acid | − | − | − | − | − | − | − | − | − | − |
| H3 | M-hydroxyphenylacetic acid | − | − | − | − | − | − | − | − | − | − |
| H4 | Tyramine | − | − | − | − | − | − | − | − | − | − |
| H5 | D-psicose | + | + | + | + | + | + | + | + | + | + |
| H6 | L-lyxose | − | − | − | − | + | + | − | − | − | − |
| H7 | Glucuronamide | + | + | + | + | + | + | + | + | + | + |
| H8 | Pyruvic acid | + | + | + | + | + | + | + | + | + | + |
| H9 | L-galactonic acid γ-lactone | + | + | + | + | + | + | + | + | + | + |
| H10 | D-galacturonic acid | + | + | + | + | + | + | + | + | + | + |
| H11 | Phenylethyl amine | − | − | − | − | − | − | − | − | − | − |
| H12 | 2-amino ethanol | − | − | − | − | − | − | − | − | − | − |

Strains 14443 and 14444

Strain 14444 has been reported to be a xylA (i.e., xylose-negative) mutant of strain 14443. The results of this experiment indicated that while strain 14443 is xylose-positive (i.e., capable of utilizing xylose), strain 14444 is xylose-negative (i.e., incapable of utilizing xylose). However, strain 1444 was found to be negative also for maltose, maltotriose, L-proline, and L-threonine. While the results observed with L-proline and L-threonine may not be significant, as these traits have been observed to be inconsistent between strains, the results obtained with maltose and maltotriose are significant, as discussed below.

Strains 14443 and 14445

Strain 14445 has been reported to be an himA mutant of strain 14443. Prior to this experiment, it was unknown what phenotypic changes due to the himA allele, would be observed in 14445, as compared with strain 14443. Differences between 14443 and 14445 were observed in eight tests. Strain 14445 was negative for utilization of maltose, maltotriose, α-ketobutyric acid, α-hydroxybutyric acid, propionic acid, glycolic acid, L-glutamic acid, and L-threonine. Although the results observed for L-glutamic acid and L-threonine may not be significant, as these traits have been observed to be inconsistent between strains, the results observed with maltose and maltotriose indicate the presence of a defect in maltose metabolism, as also observed in strain 14444. This was confirmed by contacting the source of these strains, Dr. Jeremy Glasner (in Dr. Fred Blattner's laboratory, at the University of Wisconsin), who tested these strains and confirmed that these strains had accidentally acquired a maltose metabolism defect when he prepared a batch of competent cells. Without the results of the present experiment, the accidentally introduced defect would have gone unrecognized. With regard to the defects in utilization of the other four carbon sources, it appears that the himA allele may make cells deficient in utilization of α-hydroxy acids, a new and surprising observation, that has been heretofore unrecognized.

Strains 14443 and 6321

These strains are supposed to be the same strain, and both were obtained from Dr. Barbara Bachmann, at the E. coli Genetic Stock Center. Prior to testing in this experiment, strain 14443 was maintained by Dr. Blattner's laboratory, while strain 6321 was stored at Biolog. As indicated in Table 15, these two strains were shown to have differences, some of which may be insignificant, but some of which may have resulted from improper storage and maintenance, which caused the culture to change over time.

Strains 6322, 6321, and 6320

Strain 6322 is the originating strain of the genetically important E. coil K12 culture. Strains 6321 and 6320 were reported as being derived from 6322 via genetic manipulations that eliminated the lambda phage and F+ episome.

Strain 6321 was created using careful genetic manipulations, and as indicated in Table 15, its pattern of carbon utilization observed in this experiment was very similar to that of strain 6322. However, strain 6320 was created through harsh treatment (exposure to X-rays), and it differs from strain 6322 in many traits.

Strains 11547, 13671, 1367, and 13675

These strains are all of the O157 serological line, and are considered to be human pathogens. These strains are similar to each other, but are rather different from the K-12 strains. It is well known that most O157 strains are sorbitol negative, and this was observed for these four strains. However, it was also found that these strains have other special traits. For example, all four of these strains were also negative for D-saccharic acid, and D-galactonic acid-g-lactone. In addition, three of the four strains were positive for sucrose. The negative result observed for D-galactonic acid-g-lactone is particularly interesting. The genes involved in metabolism of D-galactonic acid-g-lactone (dgo) map at 82 minutes on the E. coli genome. Recent genome sequencing data have indicated that in at least one O157 strain, a large "pathogenicity island" has been inserted in the E. coli genome at 82 minutes. It is possible that the insertion of this pathogenicity island may have resulted in the inactivation of the dgo genes.

Example 16

Phenotypic Analysis of Yeast

In this Example, yeast are analyzed for phenotypic differences using the Biolog YT MICROPLATE testing plates. S. cerevisiae strains are grown on suitable media (e.g., as described in Example 9), and inoculated into the wells of the YT MICROPLATE testing plate as described in Example 9. The ability of the strains to utilize different carbon sources (e.g., D-galactose) is then observed and compared, in order to assess the phenotypic differences between the strains. As indicated in Example 9, water or GELRITE may be used as the inoculation suspension medium, as well as 0.85% NaCl or PPS (e.g., as described in Example 15), with 100 μl inoculated per well, rather than the 150 μl used with bacteria.

Example 17

Kinetic Analysis

In this Example, two E. coli strains constructed so as to be isogenic with the exception of a single allele are compared for their ability to utilize 95 different carbon sources in the Biolog ES MICROPLATE testing plate. The strains are cultured under identical conditions by growing them at room temperature on blood agar plates (TSA with 5% sheep blood). Suspensions are prepared in PPS, as described in Example 15, above. Then, 150 μl of the suspensions are used to inoculate all of the wells of two ES MICROPLATE testing plates (i.e., one MICROPLATE testing plate for each strain). The metabolic response (i.e., purple color formation) is followed kinetically at room temperature in a plate reader (e.g., the Biolog MICROSTATION plate reader) for a 24-hour period, and recorded, using SOFTmaxPRO software (Molecular Devices). Kinetic measurements are made using one of two methods. In the first method, each of the two MICROPLATE testing plates are placed inside a kinetic plate reader and read at 15 minute intervals over a 24-hour period. In the second method, each of the two MICROPLATE testing plates are cycled in and out of a plate reader using a ROBOmax in-feed stacking device (Molecular Devices). The MICROPLATE testing plates are read at 15 minute intervals over a 24-hour period. The kinetic readings are then converted into 24-hour kinetic response patterns. The two patterns obtained are compared, in order to identify differences in the organisms' responses to each of the 95 carbon sources tested.

Example 18

Testing for Growth Stimulation by Nitrogen, Phosphorus, and Sulfur Sources, and Other Nutrients In this Example, experiments to assess the ability of E. coli to utilize various nitrogen, sulfur, and phosphorus sources were conducted using the methods described above. For these experiments, E. coli MG1655, kindly provided by Dr. Fred Blattner (University of Wisconsin, Madison), was used. In addition to the E. coli strain, two Salmonella typhimurium auxotrophs (histidine$^-$ and pyrimidine$^-$; available from Salmonella Genetic Stock Center, University of Calgary, Calgary, Alberta) were tested.

Prior to inoculating MICROPLATE testing plates, MG1655 was pre-grown overnight on the limited nutrient medium, R2A (Acumedia). MG1655 cells were streaked onto the R2A agar, and grown overnight at 35° C. Individual colonies were picked from the agar surface, using a sterile cotton swab. The cells were suspended in GN/GP—IF inoculating fluid (Biolog), at a density corresponding to 50% transmittance in a turbidimeter (Biolog), using a 20 mM diameter tube. The suspension was then diluted 8-fold, and inoculated onto the MICROPLATE testing plates. Three panels of MICROPLATE testing plates were used in these experiments, designated "EN" (used for testing nitrogen sources), "EPS" (used for testing phosphorous and sulfur sources), and "EA" (used in the auxotrophic testing experiments). The plates were incubated at 35° C. under humid conditions for 48 hours, at which time sufficient purple color had developed in the positive control wells, while the negative control wells remained colorless. During these experiments suspensions that were diluted between 4-16-fold gave the most accurate readings. More turbid solutions resulted in false positive reactions, while less turbid solutions took too long to develop color.

It was determined during the course of these experiments that pre-growth of the cells on R2A was sufficient to deplete the nutrient reserves of the organisms, such that subsequent growth in the MICROPLATE testing plates was entirely dependent upon the nutritional supplements provided in each of the wells. Indeed, R2A was chosen after careful examination of a number of pre-growth media, including Luria-Bertani (LB), TSA, TSA with 5% sheep blood, BUG (Biolog), and BUG with blood. Organisms pre-cultured on R2A were the only cultures that exhibited no growth and therefore, no purple color in the negative control wells (i.e., wells that did not contain either a nitrogen source ["N-free" well], a phosphorus source ["P-free" well], or a sulfur source ["S-free" well]).

The complete minimal medium used in the MICROPLATE testing plates contained 100 mM NaCl, 30 mM triethanolamine-HCl (pH 7.1), 25 mM sodium pyruvate, 5.0 mM $NH_4Cl$, 2.0 mM $NaH_2PO_4$, 0.25 mM $Na_2SO_4$, 0.05 mM $MgCl_2$, 1.0 mM KCl, 1.0 μM ferric chloride, and 0.01% tetrazolium violet. The ability of MG1655 to grow on the defined medium served as a positive control in each experiment. For auxotrophic testing in the EA panel, this medium was supplemented with various nutrients and/or growth factors, with vitamins and Tweens provided at 0.25 μM, nucleotides/nucleosides at 100 μM, amino acids at 10 μM, N-α- acetyl-L-ornithine, L-ornithine, L-citrulline, putrescine, spermidine, and spermine at 50 µM; and 4-amino-imidazole-4(5)-carboxamide at 1 mM. For testing various nitrogen sources (i.e., in the EN panel), the NH$_4$Cl in the medium was replaced with 3.0 mM of the nitrogen source being examined. For phosphorus and sulfur source testing on the EPS panel, the NaH$_2$PO$_4$ or Na$_2$SO$_4$ in the medium were replaced with 1.0 mM or 100 µM respectively, of the various phosphorus and sulfur sources tested. In all cases, the pH of the stock solutions containing the various test chemicals was tested, and if necessary, adjusted to approximately pH 7 with either NaOH or HCl, prior to dispensing the chemicals in the appropriate test panel(s). All of the chemicals tested were obtained from Sigma.

Nitrogen-free, sulfur-free, and phosphorous-free media were used in the negative control wells of the EN and EPS panels, and consisted of the defined minimal medium described above, with the omission of NH$_4$Cl, NaH$_2$PO$_4$, or Na$_2$SO$_4$. Lack of growth/purple color in the negative control wells indicated the absence of significant quantities of nitrogen, phosphorous and sulfur-containing contaminants that might have been present due to transfer of these elements when the organisms were inoculated in the wells of the MICROPLATE testing plates from the R2A medium.

The nitrogen sources tested included ammonium chloride, sodium nitrite, potassium nitrate, urea, glutathione (reduced form), alloxan, L-citrulline, putrescine, L-ornithine, agmatine, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-tyrosine, L-threonine, L-valine, D-alanine, D-asparagine, D-aspartic acid, D-glutamic acid, D-lysine, D-serine, D-valine, N-acetyl-glycine, L-pyroglutamic acid, L-homoserine, met-ala, n-amylamine, n-butylamine, ethylamine, ethanolamine, ethylene diamine, histamine, (R)-(+)-α-phenylethylamine, β-phenylethylamine, tyramine, acetamide, formamide, glucuronamide, lactamide, D(+)-glucosamine, D(+)-galactosamine, D-mannosamine, N-acetyl-D-glucosamine, N-acetyl-D-galactosamine, N-acetyl-D-mannosamine, adenine, adenosine, cytosine, thymine, thymidine, uracil, uridine, xanthine, xanthosine, inosine, DL-α-amino-n-butyic acid, γ-amino-n-butyric acid, ε-amino-n-caproic acid, DL-α-amino-caprylic acid, hippuric acid, parabanic acid, uric acid, urocanic acid, δ-amino-n-valeric acid, 2-amino-valeric acid, gly-glu, ala-gly, ala-his, ala-thr, gly-met, gly-gln, ala-gln, gly-ala, and gly-asn.

The phosphorus sources tested included phosphate, pyrophosphate, trimetaphosphate, tripolyphosphate, hypophosphite, thiophosphate, adenosine 2'-monophosphate, adenosine 3'-monophosphate, adenosine 5'-monophosphate, adenosine 2',3'-cyclic monophosphate, adenosine 3',5'-cyclic monophosphate, dithiophosphate, DL-α-glycero-phosphate, β-glycero-phosphate, phosphatidyl glycerol, phosphoenol pyruvate, phosphocreatine, 2'deoxy glucose 6-phosphate, guanosine 2'-monophosphate, guanosine 3'-monophosphate, guanosine 5'-monophosphate, guanosine 2',3'-cyclic monophosphate, guanosine 3',5'-cyclic monophosphate, glucose 1-phosphate, glucose 6-phosphate, fructose 1-phosphate, fructose 6-phosphate, mannose 1-phosphate, mannose 6-phosphate, arabanose 5-phosphate, cytidine 2'-monophosphate, cytidine 3'-monophosphate, cytidine 5'-monophosphate, cytidine 2',3'-cyclic monophosphate, cytidine 3',5'-cyclic monophosphate, glucosamine 1-phosphate, glucosamine 6-phosphate, phospho-L-arginine, O-phospho-D-serine, O-phospho-L-serine, O-phospho-D-tyrosine, O-phospho-L-tyrosine, uridine 2'-monophosphate, uridine 3'-monophosphate, uridine 5'-monophosphate, uridine 2',3'-cyclic monophosphate, uridine 3',5'-cyclic monophosphate, O-phospho-L-threonine, inositol hexaphosphate, nitrophenyl phosphate, 2-aminoethyl phosphonate, 6-phosphogluconic acid, 2-phosphoglyceric acid, phosphoglycolic acid, phosphonoacetic acid, thymidine 3'-monophosphate, thymidine 5'-monophosphate, methylene diphosphonic acid, and thymidine 3',5'-cyclic monophosphate.

The sulfur sources tested included sulfate, thiosulfate, tetrathionate, thiophosphate, dithiophosphate, L-cysteine, cys-gly, L-cysteic acid, cysteamine, L-cysteine-sulphinic acid, cystathionine, lanthionine, DL-ethionine, glutathione (reduced form), L-methionine, glycyl-DL-methionine, S-methyl-L-cysteine, L-methionine sulfoxide, L-methionine sulfone, taurine, N-acetyl-DL-methionine, N-acetyl cysteine, isethionate, thiourea, thiodiglycol, thioglycolic acid, thiodiglycolic acid, 1-dodecane-sulfonic acid, taurocholic acid, tetramethylene sulfone, hypotaurine, O-acetyl-serine, 3',3' thiodipropionic acid, L-djenkolic acid, and 2-mercaptoethylamine.

The auxotrophic supplements tested included L-alanine, L-arginine, L-asparagine, L-aspartic acid, adenine, adenosine, 2'-deoxyadenosine, adenosine 3',5'-cyclic monophosphate, adenosine 3'-monophosphate, adenosine 5'-monophosphate, L-cysteine, L-glutamic acid, L-glutamine, L-glycine, L-histidine, L-isoleucine, guanine, guanosine, 2'-deoxyguanosine, guanosine 3',5'-cyclic monophosphate, guanosine 3'-monophosphate, guanosine 5'-monophosphate, L-leucine, L-lysine, L-methionine, L-phenylalanine, L-proline, L-serine, cytosine, cytidine, 2'-deoxycytidine, cytidine 3',5'-cyclic monophosphate, cytidine 3'-monophosphate, cytidine 5'-monophosphate, L-tryptophan, L-tyrosine, L-threonine, L-valine, D-alanine, D-aspartic acid, thymine, thymidine, thymidine 3',5'-cyclic monophosphate, thymidine 3'-monophosphate, thymidine 5'-monophosphate, D-glutamic acid, (5)4-amino-imidazole-4(5)-carboxamide, DL-α,ε-diaminopimelic acid, D-biotin, DL-α-lipoic acid, caprylic acid, uracil, uridine, 2'-deoxyuridine, uridine 3',5'-cyclic monophosphate, uridine 3'-monophosphate, uridine 5'-monophosphate, p-amino-benzoic acid, shikimic acid, molybdic acid, folic acid, α-keto-isovaleric acid, D-pantothenic acid, hypoxanthine, inosine, 2'-deoxyinosine, inosine 3',5'-cyclic monophosphate, inosine 3'-monophosphate, inosine 5'-monophosphate, thiamine, riboflavin, pyridoxal, pyridoxine, pyridoxamine, quinolinic acid, glutathione (reduced form), L-homoserine lactone, α-ketobutyric acid, β-nicotinamide adenine dinucleotide, nicotinic acid, nicotinamide, N-α-acetyl-L-ornithine, L-ornithine, L-citrulline, putrescine, spermidine, spermine, Tween 20, Tween 40, Tween 60, Tween 80, and δ-amino-levulinic acid.

Following approximately 48 hours of incubation, the inoculated test panels were observed. For the nitrogen, phosphorus and sulfur tests, the contents of the wells in which *E. coli* was able to grow (i.e., the well contained a nitrogen, phosphorus, or sulfur source suitable for the organism) turned purple. In the auxotrophic test panel (EA), phenotypes that were stimulated by histidine or various pyrimidine compounds produced a purple color in the wells where *Salmonella* growth was stimulated.

For MG1655 tested in the EN panel, the following compounds served as suitable nitrogen sources, as indicated by a "positive" result: positive control (medium with NH$_4$Cl), L-arginine, L-asparagine, L-aspartic acid, L-glutamic acid, L-glutamine, glycine, L-proline, D-alanine, L-proline, D-alanine, D(+)-glucosamine, N-acetyl-D-glucosamine, δ-amino-n-valeric acid, gly-glu, ala-gly, ala-thr, gly-met, gly-gln, ala-gln, gly-ala, and gly-asn. The following compounds resulted in a weak positive test result: D(+)-galactosamine, D-mannosamine, and γ-amino-n-butyric acid. The following compounds were not suitable nitrogen sources (i.e., there was no MG1655 growth in wells containing these compounds): negative control (medium without any nitrogen source), sodium nitrite, potassium nitrate, urea, glutathione (reduced form), alloxan, L-citrulline, putrescine, L-ornithine, agmatine, L-alanine, L-cysteine, L-histidine, L-isoleucine, L-leucine, L-lysine, L-methionine, L-phenylalanine, L-serine, L-tyrosine, L-threonine, L-valine, D-asparagine, D-aspartic acid, D-glutamic acid, D-lysine, D-serine, D-valine, N-acetyl-glycine, L-pyroglutamic acid, L-homoserine, met-ala, n-amylamine, n-butylamine, ethylamine, ethanolamine, ethylenediamine, histamine, (R)-(+)-α-phenylethylamine, β-phenylethylamine, tyramine, acetamide, formamide, glucuronamide, lactamide, N-acetyl-D-galactosamine, N-acetyl-D-mannosamine, adenine, adenosine, cytosine, thymine, thymidine, uracil, uridine, xanthine, xanthosine, inosine, DL-α-amino-n-butyric acid, γ-amino-n-butyric acid, ε-amino-n-caproic acid, DL-α-amino-caprylic acid, hippuric acid, parabanic acid, uric acid, urocanic acid, 2-amino-valeric acid, and ala-his.

For the phosphorus and sulfur test panel (EPS), the following compounds served as suitable phosphorus or sulfur sources, as indicated by a "positive" result: positive phosphate control (medium with phosphate), positive sulfur control (medium with sulfate), trimetaphosphate, thiophosphate, hypophosphite, adenosine-2'-monophosphate, adenosine 3-monophosphate, dithiophosphate, DL-α-glycerophosphate, β-glycerophosphate, phosphoenol pyruvate, phosphocreatine, 2'-deoxyglucose 6-phosphate, guanosine 2'-monophosphate, guanosine 3'-monophosphate, guanosine 5'-monophosphate, guanosine 2':3'-cyclic monophosphate, glucose 1-phosphate, glucose 6-phosphate, fructose 1-phosphate, fructose 6-phosphate, mannose 1-phosphate, mannose 6-phosphate, arabinose 5-phosphate, cytidine 3'-monophosphate, cytidine 5'-monophosphate, cytidine 2':3'-cyclic monophosphate, glucosamine 1-phosphate, glucosamine 6-phosphate, phospho-L-arginine, O-phospho-D-serine, O-phospho-L-serine, O-phospho-D-tyrosine, O-phospho-L-tyrosine, uridine 2'-monophosphate, uridine 3'-monophosphate, uridine 5'-monophosphate, uridine 2':3'-cyclic monophosphate, O-phospho-L-threonine, 6-phosphogluconic acid, 2-phosphoglyceric acid, phosphoglycolic acid, thyrnidine 3'-monophosphate, thymidine 5'-monophosphate, thiosulfate, tetrathionate, thiophosphate, dithiophosphate, L-cysteine, cys-gly, L-cysteic acid, L-cysteine sulphinic acid, cystathionine, lanthionine, glutathione, L-methionine, glycyl-DL-methionine, L-methionine sulfoxide, taurine, N-acetyl-DL-methionine, isethionate, taurocholic acid, hypotaurine, O-acetyle-serine with sodium sulfate, L-djenkolic acid. The following compounds resulted in a weak positive test result: 2-aminoethyl phosphonate, S-methyl-L-cysteine. The following compounds were not suitable phosphorous or sulfur sources (i.e., there was no MG1655 growth in wells containing these compounds: negative control (medium without any phosphorus or sulfur source), pyrophosphate, tripolyphosphate, adenosine 5'-monophosphate, adenosine 2':3'-cyclic monophosphate, adenosine 3':5'-cyclic monophosphate, phosphatidyl glycerol, guanosine 3':5'-cyclic monophosphate, cytidine 2'-monophosphate, cytidine 3':5'-cyclic monophosphate, uridine 3':5'-cyclic monophosphate, inositol hexaphosphate, nitrophenyl phosphate, phosphonoacetic acid, methylene diphosphonic acid, thymidine 3':5'-cyclic monophosphate, DL-ethionine, L-methionine sulfone, N-acetyl cysteine, thiourea, thiodiglycol, thioglycolic acid, thiodiglycolic acid, 1-dodecane-sulfonic acid, and tetramethylene sulfone.

Finally, as MG1655 is not auxotrophic for any nutrients or growth factors, this strain was capable of growing in all wells of the EA panel. Instead, two *S. typhimurium* auxotrophs were used in the EA experiments. With one strain, hisF645, only the well containing L-histidine turned purple, while with the other strain, pyrCΔ73, wells containing a pyrimidine (i.e., uracil, cytosine, uridine, cytidine, 2-deoxyuridine, 2-deoxycytidine, uridine 3'-monophosphate, uridine 5'-monophosphate, cytidine 2'-monophosphate, cytidine 3'-monophosphate, and cytidine 5'-monophosphate) turned purple and wells containing a purine (i.e., adenosine 2'-monophosphate, adenosine 3'-monophosphate, adenosine 5'-monophosphate, guanosine 2'-monophosphate, guanosine 5'-monophosphate, guanine, inosine, 2'-deoxyadenosine, and 2'deoxyguanosine), turned weakly purple. These results demonstrated the appropriate stimulation of organism growth.

Example 19

Additional Testing of Bacteria

In this Example, the susceptibility of *E. coli* (MG1655) was tested in the presence of vancomycin (10 µg/ml) or sulfamethoxazole (235 µg/ml) in microarrays containing various additional compounds. The microarrays were present in three Biolog sensitivity test panels, referred to as ES1, ES2 and ES3 MICROPLATE testing plates. The organisms were added to a sterile aqueous suspension containing 0.40% NaCl, 0.03% pluronic F68, 0.01% phytagel, and 0.01% tetrazolium violet, to a cell density of 85% transmittance (as measured using a Biolog turbidimeter). The BAC to be tested was added to the suspension just prior to inoculating the organisms (100 µl/well) into the wells of the microarrays. The wells of these ES MICROPLATE testing plates contained a basal broth medium consisting of tryptone (2 g/L), yeast extract (1 g/L), and NaCl (1 g/L).

In addition to one positive control well, the wells of the ES1 plates contained the following antimicrobials (one compound at a particular concentration per well): acriflavine (4.0 µg/ml, 8.0 µg/ml, and 16 µg/ml), ampicillin (2.0 µg/ml, 4.0 µg/ml, 8.0 µg/ml, and 16 µg/ml), nafcillin (75 µg/ml, 150 µg/ml, 300 µg/ml, and 600 µg/ml,), lincomycin (50 µg/ml, 100 µg/ml, 200 µg/ml, and 400 µg/ml), chloramphenicol (0.1 µg/ml, 0.2 µg/ml, 0.4 µg/ml, and 0.8 µg/ml), chlortetracycline (0.125 µg/ml, 0.25 µg/ml, 0.50 µg/ml, and 1.0 µg/ml), tetracycline (0.033 µg/ml, 0.066 µg/ml, 0.133 µg/ml, and 0.266 µg/ml), gentamycin (0.25 µg/ml, 0.50 µg/ml, 1.0 µg/ml, and 2.0 µg/ml), kanamycin (0.25 µg/ml, 0.5 µg/ml, 1.0 µg/ml, and 2.0 µg/ml), neomycin (0.75 µg/ml, 1.5 µg/ml, 3.0 µg/ml, and 6.0 µg/ml), vancomycin (10 µg/ml, 20 µg/ml, 40 µg/ml, and 80 µg/ml), bacitracin (208 µg/ml, 416 µg/ml, 833 µg/ml, and 1666 µg/ml), clindamycin (3.3 µg/ml, 6.6 µg/ml, 13.2 µg/ml, and 26.4 µg/ml), cloxacillin (100 µg/ml, 200 µg/ml, 400 µg/ml, and 800 µg/ml), erythromycin (2.5 µg/ml, 5.0 µg/ml, 10 µg/ml, and 20 µg/ml), penicillin G (5 µg/ml, 10 µg/ml, 20 µg/ml, and 40 µg/ml), novobiocin (33 µg/ml, 66 µg/ml, 133 µg/ml, and 266 µg/ml), spiramycin (5.0 µg/ml, 10 µg/ml, 20 µg/ml, and 40 µg/ml,), trimethoprim (0.17 µg/ml, 0.33 µg/ml, 0.67 µg/ml, and 1.3 µg/ml), streptomycin (0.38 µg/mi, 0.75 µg/ml, 1.5 µg/ml, and 3.0 µg/ml), cephaloridine (0.75 µg/ml, 1.5 µg/ml, 3.0 µg/ml, and 6.0 µg/ml), cefuroxime (0.5 µg/ml, 1.0 µg/mi, 2.0 µg/ml, and 4.0 µg/ml), roxithromycin (10 µg/ml, 20 µg/ml, 40 µg/ml, and 80 µg/ml), and piperacillin (0.5 µg/ml, 1.0 µg/ml, 2.0 µg/ml, and 4.0 µg/ml).

The wells of the ES2 plates contained the following antimicrobials (one compound at a particular concentration per well): azomycin (0.2 µg/ml, 0.4 µg/ml, 0.8 µg/ml, and 1.6 µg/ml), rifampicin (0.25 µg/ml, 0.5 µg/ml, 1.0 µg/ml, and 2.0 µg/ml), tylosin tartrate (25 µg/ml, 50 µg/ml, 100 µg/ml, and 200 µg/ml), cefazolin (0.5 µg/ml, 1.0 µg/ml, 2.0 µg/ml, and 4.0 µg/ml), cephalothin (2.5 µg/ml, 5.0 µg/ml, 10 µg/ml, and 20 µg/ml), cefaclor (0.66 µg/ml, 1.33 µg/ml, 2.66 µg/ml, and 5.33 µg/ml), rifamycin SV (1.5 µg/ml, 3.0 µg/ml, 6.0 µg/ml, and 12 µg/ml), cefsulodin 4.0 µg/ml, 8.0 µg/ml, 16 µg/ml, and 32 µg/ml), cefotaxime (0.05 µg/ml, 0.1 µg/ml, 0.2 µg/ml, and 0.4 µg/ml), cefoxitin (0.75 µg/ml, 1.5 µg/ml, 3.0 µg/ml, and 6.0 µg/ml), puromycin (12 µg/ml, 25 µg/ml, 50 µg/ml, and 100 µg/ml), spectinomycin (3.5 µg/ml, 7.0 µg/ml, 14 µg/ml, and 28 µg/ml), fusidic acid (50 µg/ml, 100 µg/ml, 200 µg/ml, and 400 µg/ml), phosphomycin (0.2 µg/ml, 0.4 µg/ml, 0.8 µg/ml, and 1.6 pg/ml), phleomycin (0.25 µg/ml, 0.5 µg/ml, 1.0 µg/ml, and 2.0 µg/ml), amikacin (0.25 µg/ml, 0.5 µg/ml, 1.0 µg/ml, and 2.0 µg/ml), isoniazid (300 µg/ml, 600 µg/ml, 1200 µg/ml, 2400 µg/ml), ethionamide (25 µg/ml, 50 µg/ml, 100 µg/ml, and 200 µg/ml), SDS (50 µg/ml, 100 µg/ml, 200 µg/ml, 400 µg/ml), dodecyltrimethyl ammonium bromide (10 µg/ml, 20 µg/ml, 40 µg/ml, and 80 µg/ml), BIGCHAP (2000 µg/ml, 4000 µg/ml, 8000 µg/ml, and 16,000 µg/ml), niaproof (0.08%, 0.16%, 0.32%, and 0.64%), CHAPS (1500 µg/ml, 3000 µg/ml, 6000 µg/ml, 12,000 µg/ml), and N-lauryl sarcosine (1000 µg/ml, 2000 µg/ml, 4000 µg/ml and 8000 µg/ml).

The wells of the ES3 plates contained the following antimicrobials (one compound at a particular concentration per well): nalidixic acid (0.5 µg/ml, 1.0 µg/ml, 2.0 µg/ml, 4.0 µg/ml), taurocholic acid (600 µg/ml, 1200 µg/ml, 2400 µg/ml, and 4800 µg/ml), colistin (0.25 µg/ml, 0.5 µg/ml, 1.0 µg/ml, and 2.0 µg/ml), procaine (2500 µg/ml, 5000 µg/ml, 10,000 µg/ml, and 20,000 µg/ml), diamide (16.6 µg/ml, 33.3 µg/ml, 66.6 µg/ml, and 133 µg/ml), hydroxylamine (12 µg/ml, 25 µg/ml, 50 µg/ml, and 100 µg/ml), guanidine (500 µg/ml, 1000 µg/ml, 2000 µg/ml, and 4000 µg/ml), cupric chloride (20 µg/ml, 40 µg/ml, 80 µg/ml, and 160 µg/ml), zinc chloride (10 µg/ml, 20 µg/ml, 40 µg/ml, and 80 µg/ml), cadmium chloride (5.0 µg/ml, 10 µg/ml, 20 µg/ml, and 40 µg/ml), nickel chloride (20 µg/ml, 40 µg/ml, 80 µg/ml, and 160 µg/ml), chromium chloride (100 µg/ml, 200 µg/ml, 400 µg/ml, and 800 µg/ml), sodium selenite (100 µg/ml, 200 µg/ml, 300 µg/ml, and 400 µg/ml), potassium tellurite (0.2 µg/ml, 0.4 µg/ml, 0.8 µg/ml, and 1.6 µg/ml), manganese sulfate (100 µg/ml, 200 µg/ml, 400 µg/ml, and 800 µg/ml), cobalt chloride (12 µg/ml, 25 µg/ml, 50 µg/ml, and 100 µg/ml), silver chloride (2.0 µg/ml, 4.0 µg/ml, 8.0 µg/ml, and 16 µg/ml), potassium chromate (10 µg/ml, 20 µg/ml, 40 µg/ml, and 80 µg/ml), potassium bromide (225 µg/ml, 450 µg/ml, 900 µg/ml, and 1800 µg/ml), sodium cyanate (155 µg/ml, 310 µg/ml, 600 µg/ml, and 1200 µg/ml), sodium azide (500 µg/ml, 1000 µg/ml, 2000 µg/ml, and 4000 µg/ml), picolinic acid (50 µg/ml, 100 µg/ml, 200 µg/ml, and 400 µg/ml), potassium superoxide (100 µg/ml, 200 µg/ml, 400 µg/ml, and 800 µg/ml) and menadione (3.3 µg/ml, 6.6 µg/ml, 13.3 µg/ml, and 26.6 µg/ml)

The results of the first experiment indicated that in the presence of 10 µg/ml vancomycin, the *E. coli* strain tested exhibited transient increased sensitivity only to vancomycin at 10 µg/ml, 20 µg/ml, 40 µg/ml, and 80 µg/ml. In addition, the strain exhibited increased sensitivity to novobiocin at 33 µg/ml and 66 µg/ml, trimethoprim at 0.17 ng/ml, 0.33 ng/ml, 0.67 ng/ml, and 1.3 ng/ml, cefazolin at 2.0 µg/ml and 4.0 µg/ml, cephalothin at 10 µg/ml and 20 µg/ml, cefoxitin at 0.75 µg/ml and 1.5 µg/ml, fusidic acid at 200 µg/ml and 400 µg/ml, and nalidixic acid at 1.0 µg/ml, 2.0 µg/ml, and 4.0 µg/ml. Normal sensitivity levels were observed for the other tests in the ES1, ES2 and ES3 microarray panels.

The results also indicated that in the presence of 235 µg/ml sulfamethoxazole, the *E. coli* strain exhibited increased resistance to chlortetracycline at 0.25 µg/ml, 0.50 µg/ml, and 1.0 µg/ml, tetracycline at 0.033 µg/ml, 0.066 µg/ml, 0.133 µg/ml, and 0.266 µg/ml, novobiocin at 66 µg/ml and 133 µg/ml, but exhibited increased sensitivity to trimethoprim at 0.17 ng/ml, 0.33 ng/ml, 0.67 ng/ml, and 1.3 ng/ml, cephaloridine at 0.75 µg/ml, 1.5 µg/ml, 3.0 µg/ml, and 6.0 µg/ml, azomycin at 0.2 µg/ml, 0.4 µg/ml, 0.8 µg/ml, and 1.6 µg/ml, cefazolin at 0.5 µg/ml, 1.0 µg/ml, 2.0 µg/ml, and 4.0 µg/ml, cephalothin at 5.0 µg/ml, 10 µg/ml, and 20 µg/ml, cefaclor at 1.33 µg/ml, 2.66 µg/ml, and 5.33 µg/ml, cefsulodin at 8 µg/ml and 16 µg/ml, nickel chloride at 20 µg/ml and 40 µg/ml, chromium chloride at 200 µg/ml and 400 µg/ml, and cobalt chloride 12 µg/ml and 25 µg/ml. Normal sensitivity levels were observed for the other tests in the ES1, ES2 and ES3 microarray panels. Thus, this Example clearly illustrates the use of the present invention to test for synergy and/or antagonism using combinations of BACs.

Example 20

Antimicrobial Testing

In this Example, experiments are described in which the feasibility of using PMs for analyzing the metabolic effects of antimicrobial compounds and their mechanisms of action were investigated. Specifically, the experiments were designed to determine whether compounds that act via interaction with specific bacterial proteins ("target-specific") can be distinguished from those acting via non-specific mechanisms, solely on the basis of differences in signature metabolic profiles. In addition, the experiments were designed to determine whether different interactors of the same pathway produce a similar signature profile, as well as whether interactors of different pathways produce distinctly different profiles.

Twenty chemicals were selected for inclusion in these experiments. Fifteen of these, listed below in Table 16 as "single target antimicrobials" are thought to have relatively specific modes of action, whereas five antimicrobials, listed as "multiple target antimicrobials" are thought to have non-specific modes of action. Among the single target compounds were three sets of antimicrobials with similar modes of action on the cell wall (ampicillin, cephalothin, phosphomycin, and bacitracin), ribosomes (chloramphenicol, streptomycin, and tetracycline), or DNA gyrases (nalidixic acid, oxolinic acid, and coumermycin).

An initial set of experiments was performed to select the concentrations of each chemical, as it was desirable to use a partially inhibitory concentration. A completely inhibitory or sub-inhibitory concentration would not provide any information. Partial inhibitory levels were determined using the criterion of decreased formation of purple color due to inhibition of tetrazolium violet reduction (i.e., respiration). Each compound was tested at two concentrations giving partial inhibition of respiration. The lower concentration, referred to as "1×," was the lowest concentration giving detectable inhibition of respiration. The higher concentration, referred to as "2×," was twice the 1× concentration. For most chemicals, another doubling to 4× gave a completely inhibitory level that would not be useful. Thus, only 1× and 2× concentrations were used. It was determined that the selection of chemical concentration is an important parameter to control. However, the selection criteria used herein was found to be quite adequate. Only canavanine appeared to need a slightly higher concentration to give comparable results. If the concentration is chosen properly, only one concentration should be needed for the assay.

TABLE 16

Compounds Used and Their Modes of Action

| Compound | Target | Assumed Mode of Action |
|---|---|---|
| Ampicillin | Single | Cell wall |
| Cephalothin | Single | Cell wall |
| Phosphomycin | Single | Cell wall |
| Bacitracin | Single | Cell wall |
| Polymyxin B | Single | Outer membrane |
| Cerulenin | Single | Membrane (fatty acid synthesis) |
| Chloramphenicol | Single | Ribosome |
| Streptomycin | Single | Ribosome |
| Tetracycline | Single | Ribosome, lipophilic chelator |
| Bleomycin | Single | DNA polymerase |
| Rifampicin | Single | RNA polymerase |
| Nalidixic Acid | Single | DNA gyrase |
| Oxolinic Acid | Single | DNA gyrase |
| Coumermycin | Single | DNA gyrase |
| Sulfathiazole | Single | Anti-folate |
| Sodium Dodecyl Sulfate (SDS) | Multiple | Membrane and protein denaturant |
| 5-Fluoro-Uracil (5-FU) | Multiple | Uracil analog |
| Canavanine | Multiple | Amino acid analog |
| N-ethyl Maleimide (NEM) | Multiple | Thiol reactive agent |
| Ethylmethane Sulfonate (EMS) | Multiple | Mutagen (alkylating agent) |

In these experiments, *E. coli* MG1655 was tested against 20 antimicrobials at two concentrations using 7 PMs each, for a total of 280 PMs. PMs without any antimicrobial (a set of 7) were run each day as a control (this total does not include data from the control strains). Since in these experiments each PM contains 95 phenotypes, the total number of phenotypes analyzed here was 26,600. Each PM was monitored kinetically every 15 minutes using a specialized instrument described in U.S. patent application Ser. No. 09/277,353 (herein incorporated by reference) for an incubation duration of 48 hours. Thus, the total number of data points for the experiments was 5,107,200. Bioinformatics software (Biolog) as used to analyze these data.

The results of the data collected for a run is a kinetic phenotype of the cell exposed to an antimicrobial overlaid and compared against the phenotype of the cell without exposure to the antimicrobial. When the two kinetic tracings of tetrazolium reduction (i.e., cell respiration) overlap, there is no difference in the response to that phenotype (indicated as "O"). When the control tracing exceeds the antimicrobial tracing, the organism is scored as "more sensitive" or "S." When the antimicrobial tracing exceeds the control tracing, the organism is scored as "more resistant," or "R." Based on visual examination of the PMs after incubation, the threshold values for judging S and R results were determined. The software then automatically calculated the areas under the differential tracings and applied threshold values to score all 26,600 phenotypes as S, O, or R.

From the S—O—R data, a distance matrix was generated. The S—O—R response (a string of 665 values) for one antimicrobial was compared to the response for another antimicrobial, and the differences summed up. A difference of O to S or of O to R was assigned a value of 1, and a difference of S to R was assigned a value of 2. The string of 665 differences was then summed up. Pairs of antimicrobials with similar responses had lower difference values and pairs of antimicrobials with very different responses had higher difference values. The comparison of all pairs provides a distance matrix that can be used as input for algorithms that generate various cluster diagrams to help simplify and summarize the data.

Figure 9:
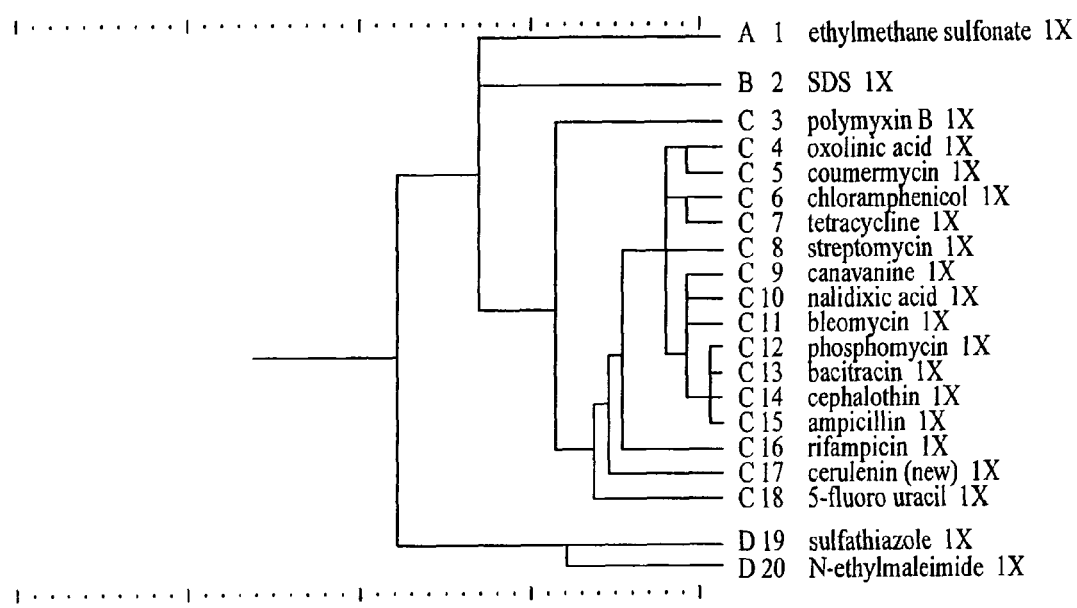
FIG. 9 provides a dendrogram showing the response of *E. coli* to various antimicrobials.

The results indicated a wide variation in the response of the organism to different classes of antimicrobials. For example, FIG. 9 shows a dendrogram of the data obtained at the 1× level of each antimicrobial. The four cell wall inhibitors (ampicillin, cephalothin, phosphomycin, and bacitracin) cluster, as do the three ribosome inhibitors (chloramphenicol, streptomycin, and tetracycline). Also, two out of the three of the DNA gyrase inhibitors (oxolinic acid and coumermycin) clustered. All of the single target antimicrobials except sulfathiazole and polymyxin B are in the tightly clustered center of the dendrogram, while all of the multiple target antimicrobials except canavanine are in the distant periphery of the dendrogram.

First, these results indicate that the present invention can be used to differentiate single target from multiple target antimicrobials. The multiple target antimicrobials make cells broadly and non-specifically hypersensitive, whereas the single target antimicrobials have a more specific "fingerprint." Second, this fingerprint pattern appears to successfully permit grouping of antimicrobials based upon their mode of action and differentiates them from other antimicrobials with different modes of action.

In one case, the results were not as simple as expected. In this case, nalidixic acid did not cluster with the other two DNA gyrase inhibiting chemicals. This may indicate something about the mechanism of action of this drug. In addition, polymyxin B, cerulenin and sulfathiazole gave results that more closely resembled the multiple target antimicrobials. Polymyxin B and cerulenin both affect membrane synthesis and this may disrupt many cellular properties, as well as enhance the non-specific permeation of other antimicrobials.

Example 21

Testing of Yeast

In this Example, the response of a yeast cell to various compounds was tested. The yeast used in these experiments was *Saccharomyces cerevisiae* (BY4741, obtained from Dr. Mark Johnston, Washington University, St. Louis, Mo.). The genotype of this strain was indicated as being Mat a (i.e., mating type "a"), ura-, his-, leu-, and met-.

In these experiments, the ability of this strain to grow in a culture medium without methionine was investigated. Methionine interferes with the ability to test this organism for its utilization of other potential sulfur sources (i.e., if methionine is added to a culture medium the organism preferentially uses it as a sulfur source).

The yeast was grown for 48 hours at 30° C. on R2A agar medium (Acumedia). Cells were removed from the agar surface with a sterile cotton swab and suspended at a cell density of 65% transmittance (as read using a Biolog turbidimeter) in an inoculating fluid containing 50 mM glucose, 0.15 mM uracil, 0.15 mM L-histidine, 0.15 mM L-leucine, 0.15 mM $MgCl_2$, 1.0 mM $CaCl_2$, 2.0 mM NaCl, 1.0 mM KCl, 3.0 mM $NH_4Cl$, 1.0 mM $NaH_2PO_4$, 0.1 mM $Na_2SO_4$, 0.01% iodonitro-tetrazolium violet, 0.01% phytagel (gellan gum), 0.03% pluronic F-68; the pH was adjusted to 6.0.

The cell suspension (100 μl/well) was then used to inoculate a Biolog EA MICROPLATE, which tests the ability of a cell to be stimulated by a set of 95 different nutrients. The nutrients included within the microarray were: LB medium (10 g/L tryptone, 5 g/L yeast extract, and 5 g/L NaCl), L-alanine (25 μM), L-arginine (25 μM), L-asparagine (25 μM), L-aspartic acid (25 µM), L-cysteine (25 µM), L-glutamic acid (25 µM), adenosine 3',5'-cyclic monophosphate (100 µM), adenine (100 µM), adenosine (100 µM), 2'-deoxyadenosine (100 µM), L-glutamine (25 µM), glycine (25 µM), L-histidine (25 µM), L-isoleucine (25 µM), L-leucine (25 µM), L-lysine (25 µM), L-methionine (25 µM), L-phenylalanine (25 µM), guanosine 3',5'-cyclic monophosphate (100 µM), guanine (100 µM), guanosine (100 µM), 2'-deoxyguanosine (100 µM), L-proline (25 µM), L-serine (25 µM), L-threonine (25 µM), L-tryptophan (25 µM), L-tyrosine (25 µM), L-valine (25 µM), L-isoleucine and L-valine (25 µM each), trans-4-hydroxy L-proline (25 µM), (5) 4-aminoimidazole-4(5)-carboxamide (1 mM), hypoxanthine (100 µM), inosine (100 µM), 2'-deoxyinosine (100 µM), L-ornithine (100 µM), L-citrulline (100 µM), chorismic acid (100 µM), (−) shikimic acid (100 µM), L-homoserine lactone (100 µM), D-alanine (25 µM), D-aspartic acid (25 µM), D-glutamic acid (25 µM), DL-α, ε-diaminopimetic acid (25 µM), cytosine (100 µM), cytidine (100 µM), 2-deoxycytidine (100 µpM), putrescine (25 µM), spermidine (25 µM), spermine (25 µM), pyridoxine (0.25 µM), pyridoxal (0.25 µM), pyridoxamine (0.25 µM), β-alanine (0.25 µM), D-pantothenic acid (0.25 µM), orotic acid (1 mM), uracil (100 µM), uridine (100 µM), 2'-deoxyuridine (100 µM), quinolinic acid (0.25 µM), nicotinic acid (0.25 µM), nicotinamide (0.25 µM), β-nicotinamide adenosine dinucleotide (0.25 µM), δ-amino-levulinic acid (0.25 µM), hematin (0.25 µM), deferoxamine mesylate (0.25 µM), glucose (1 mM), N-acetyl-D-glucosamine (100 µM), thymine (100 µM), glutathione (reduced form; 100 µM), thymidine (100 µM), oxaloacetic acid (1 mM), d-biotin (0.25 µM), cyanobalamine (0.25 µM), p-aminobenzoic acid (0.25 µM), folic acid (0.25 µM), inosine (100 µM) and thiamine (25 µM), thiamine (0.25 µM), thiamine pyrophosphate (0.25 µM), riboflavin (0.25 µM), pyrrolo-quinoline quinone (0.25 µM), menadione (0.25 µM), myo-inositol (0.25 µM), butyric acid (100 µM), DL-α-hydroxybutyric acid (100 µM), α-ketobutyric acid (100 µM), caprylic acid (100 µM), DL-α-lipoic acid (oxidized form; 0.25 µM), DL-mevalonic acid (0.25 µM), DL-carnitine (0.25 µM), choline (0.25 µM), Tween-20 (0.01%), Tween-40 (0.01%), Tween-60 (0.01%), and Tween-80 (0.01%). One well (A-1) contains no nutrients and is used as a reference (i.e., control) well.

After inoculation, the microarray was incubated at 30° C. for 2 days and visually observed. Any well that contained nutrient that stimulated growth of the cells had a higher level of pink color due to increased cell respiration and reduction of the iodo-nitro-tetrazolium violet dye.

Three wells showed increased pink color. These wells were the wells containing L-methionine, glutathione and pyridoxine. It was expected that methionine would be stimulatory, but it was unexpected that glutathione and pyridoxine would be stimulatory and could be used to substitute for methionine. In this case, because the ability of the organism to utilize various sulfur sources was being tested, glutathione could not be used as it also contains sulfur. However, pyridoxine does not contain sulfur, and could be used as a totally satisfactory replacement for methionine as a nutrient for S. cerevisiae strain BY474 1. Thus, instead of growing and testing BY4741 on minimal media containing uracil, L-histidine, L-leucine, and L-methionine, it is possible to grow and test this strain on minimal media containing uracil, L-histidine, L-leucine, and pyridoxine.

Example 22

General Testing Methods for Carbon Source Utilization Testing of Adherent Cells

In this Example, general protocols for testing animal cells are described. The protocols are based upon the methods originally developed by Mossman (Mossman, J. Immunol. Meth., 65:55-63, 1983) and improved upon by others such as Alley et al. (Alley et al., Cancer Res., 48:589-601, 1988), but with important differences that facilitate adaptation of the methods for use in such testing formats as PHENOTYPE MICROARRAY testing panels (Biolog). Those skilled in the art recognize that the testing parameters used in these methods need to be optimized for each particular testing situation (See also, Example 24). These parameters include: the number of cells seeded in each well of the testing panel(s); the concentration of glucose, pyruvate, glutamine, amino acids, FBS, phenol red, and riboflavin that is optimal for use in the inoculating fluid; the concentration of bicarbonate in the inoculating fluid and whether any additional buffering agent (e.g., HEPES) is needed; the length of incubation following inoculation of the testing panels; the amount of chromogenic reagent (e.g., MTT) added (typically, the concentration range is 15 to 500 µg/ml, with 100 to 200 µg/ml often proving most optimal); the amount (e.g., 0 to 20 µM) and type of electron carrier (e.g., menadione bisulfite) added; the length of incubation after the chromogenic reagent is added to the testing panels; and whether the chromogenic reagent requires resolubilization (e.g., the DMSO solubilization procedure of Alley et al., supra). In some embodiments, biologically active compound(s) of interest are added to the cell suspension just prior to adding the cells to the testing panels. In still further embodiments, biologically active compound(s) of interest are added to the testing panels prior to adding the cells to the testing panels.

Cells from any source (e.g., IMR-90 cells, or any other animal or plant cells of interest) are cultured using standard cell growth containers, methods and culture media (e.g., DMEM) until near-confluence is reached. When the cells are ready for testing, the culture medium is removed from the culture, the cells are detached from the substrate as known in the art (e.g., trypsin-EDTA treatment), washed once or twice, as needed (e.g., in HBSS) to remove any remaining culture medium and phenol red. Then, the cells are suspended in an inoculation medium (IF-h). IF-h is similar to standard culture media (e.g., DMEM), but it does not contain significantly metabolizable amounts of potential carbon sources for the cell (e.g., glucose, pyruvate, glutamine, FBS, etc.). In preferred embodiments, potentially interfering dyes (e.g., phenol red) and electron carriers (e.g., riboflavin) are also removed. The cell density in the suspension is determined using methods known in the art (e.g., using a Coulter Counter or manually counting cells using a hemacytometer) and adjusted to a cell density of approximately 10,000 to 20,000 cells/ml in some embodiments, while in other embodiments the cell density is adjusted to 25,000 to 400,000 cells/ml). Then, approximately 100 µl of this suspension is pipetted into each well of a testing panel (e.g., PHENOTYPE MICROARRAY testing panels, such as PM1a [Biolog]), to provide about 1,000 to 2,000 cells/well (more preferably 2,500 to 40,000 cells/well) for wells that contain approximately the same volume as a standard microtiter plate available from Biolog. These testing panels contain various testing substrates (e.g., carbon sources) of interest.

The inoculated test panels are incubated using appropriate conditions of temperature, humidity, and $CO_2$ concentration, until the cells have attached to the well surfaces and grown to confluence in the "positive" control well (e.g., the well in the test panel that contains glucose). In other embodiments, the cells are maintained for variable lengths of time, typically between 1 and 3 days. Then, a chromogenic reagent (e.g., MTT, with or without an electron carrier such as menadione bisulfite) is added to the wells. The testing panels are further incubated under appropriate conditions, and examined at suitable intervals (e.g., 30 minutes to 24 hours) for the development of color within the wells. In preferred embodiments, the total incubation time is usually six hours or less.

For wells containing optimal concentrations of cells that can oxidize the carbon source present in the wells, there is an increase in color, as compared to the negative control well, due to the reduction of the dye. Thus, the method provides means to visualize and assess the active carbon metabolism pathways of the cell being tested.

One inoculating fluid or suspension medium suitable for use contains the following ingredients in a total volume of 250 ml: water (147.5 ml), 10× basal medium (25 ml), 100× redox dye (2.5 ml MTT [1 mg/ml]), 10× glutamine (25 ml), 1× $NaHCO_3$ (25 ml), fetal bovine serum (25 ml). In some embodiments, antimicrobials (e.g., penicillin and streptomycin, etc.) are used in this inoculating fluid, as appropriate. The basal medium used in this formula contains DMEM without glucose, pyruvate, glutamine, bicarbonate, phenol red, or riboflavin. The glutamine and $NaHCO_3$ concentrations are those used in DMEM. The pH is adjusted down to about 7.4, by bubbling $CO_2$ into the medium.

Another suitable suspension medium is an RPMI 1640 type medium lacking glucose and phenol red, but containing 0.3 mM glutamine, and 5% FBS. Typical alterations of this forumala include varying concentrations of FBS (0 to 20%, with or without dialysis), and amino acids (none to final amounts typically present in standard RPMI 1640 medium). The 10× redox dye (5.5 µl of MTT at 4 mM) and 10× electron carrier (5.5 µl at 0.4 mM) are added together to the wells of the testing device to initate color development.

Example 23

General Testing Methods for Carbon Source Utilization Testing of Suspension Cell Cultures In this Example, general protocols for testing cells grown in suspension and on microcarrier beads are described. The protocols are similar to those described in Example 22, although adaptations are made for use with cells grown in suspension (e.g., cells such as HeLa cells that are anchorage-independent and capable of growing in suspension cultures), as well as cells (e.g., IMR-90 cells) that are attached to microcarrier beads. The cells are transferred into a stirred liquid growth medium. As with Example 22, those skilled in the art recognize that the testing parameters used in these methods need to be optimized for each particular testing situation (See also, Example 25). These parameters include: the number of cells seeded in each well of the testing panel(s); the concentration of glucose, pyruvate, glutamine, FBS, phenol red, and riboflavin that is optimal for use in the inoculating fluid; the concentration of bicarbonate in the inoculating fluid and whether any additional buffering agent (e.g., HEPES) is needed; the length of incubation following inoculation of the testing panels; the amount of chromogenic reagent (e.g., MTT) added (typically, the concentration range is 15 to 500 µg/ml, with 100 to 200 µg/ml often proving most optimal); the amount (e.g., 0 to 20 µM) and type of electron carrier (e.g., menadione bisulfite) added; the length of incubation after the chromogenic reagent is added to the testing panels; and whether the chromogenic reagent requires resolubilization (e.g., the DMSO solubilization procedure of Alley et al. (Alley et al., supra). In some embodiments, the amount and type of gelling agent (e.g., 0 to 0.1% gellan gum) are also optimized. In alternative embodiments, animal, plant and/or microbial cells are used in similar protocols for testing of the effects of biologically active compounds on cells. In some embodiments, the biologically active compound(s) of interest are added to the cell suspension just prior to adding the cells to the testing panels. In still further embodiments, biologically active compound(s) of interest are added to the testing panels prior to adding the cells to the testing panels.

Cells from any source (e.g., IMR-90 cells, or any other animal or plant cells of interest) are cultured using standard cell growth containers, methods and culture media (e.g., DMEM) until a desirable cell density is established (e.g., near confluence). When the cells are ready for testing, the cells are harvested (e.g., by centrifugation), washed once or twice, as needed (e.g., in HBSS) to remove any remaining culture medium and phenol red. Then, the cells are suspended in an inoculation medium (IF-h). IF-h is similar to standard culture media (e.g., DMEM), but it does not contain significantly metabolizable amounts of potential carbon sources for the cell (e.g., glucose, pyruvate, glutamine, FBS, etc.). In preferred embodiments, potentially interfering dyes (e.g., phenol red) and electron carriers (e.g., riboflavin) are also removed. The cell density in the suspension is determined using methods known in the art (e.g., using a Coulter Counter or manually counting cells using a hemacytometer) and adjusted to a cell density of approximately 10,000 to 60,000 cells/ml (preferably 25,000 to 400,000 cells/well). In some embodiments, a chromogenic reagent (e.g., MTT, with or without an electron carrier such as menadione bisulfite) is included in the IF-h. In other embodiments, a gelling agent is also included in the IF-h. In gelled embodiments, a gel-initiating agent is typically present in the wells of the testing panel(s). Then, approximately 100 µl of this suspension is pipetted into each well of a testing panel (e.g., PHENOTYPE MICROARRAY testing panels, such as PM1a [Biolog]), to provide about 1,000 to 6,000 cells/well (preferably 2,500 to 40,000 cells/well) for wells that contain approximately the same volume as a standard microtiter plate available from Biolog. These testing panels contain various testing substrates (e.g., carbon sources) of interest.

The inoculated test panels are incubated using appropriate conditions of temperature, humidity, and $CO_2$ concentration, and the wells are examined at suitable intervals (e.g., 30 minutes) for the development of color within the wells. In preferred embodiments, the total incubation time is usually 24 hours or less. These methods provide advantages such as requiring fewer steps and less manipulation of the cells. In addition, the cells are not subjected to the stress of detachment and reattachment to a substrate.

For wells containing optimal concentrations of cells that can oxidize the carbon source present in the wells, there is an increase in color, as compared to the negative control well, due to the reduction of the dye. Thus, the method provides means to visualize and assess the active carbon metabolism pathways of the cell being tested.

One inoculating fluid or suspension medium suitable for use contains the following ingredients in a total volume of 250 ml: water (147.5 ml), 10× basal medium (25 ml), 100× redox dye (2.5 ml MTT [1 mg/ml]), 10× glutamine (25 ml), 10× $NaHCO_3$ (25 ml), fetal bovine serum (25 ml). In some embodiments, antimicrobials (e.g., penicillin and streptomycin, etc.) are used in this inoculating fluid, as appropriate. The basal medium used in this formula contains DMEM without glucose, pyruvate, glutamine, bicarbonate, phenol red, or riboflavin. If gellan gum is added to the IF-h, it is added at a final concentration of approximately 0.01% to 0.05%. The glutamine and $NaHCO_3$ concentrations are those used in DMEM. The pH is adjusted down to about 7.4, by bubbling $CO_2$ into the medium. Another suitable suspension medium is the RPMI 1640 type suspension medium described in Example 22.

Example 24

Optimization of Testing Methods

In this Example, considerations in the optimization of the testing system for animal cells are described. Those of skill in the art recognize that protocols often require modification and optimization for use in particular settings. Although the basic methods and reagents remain the same, variations are sometimes necessary. For example, for some cells, optimization of the cell density is important in obtaining reliable results. Thus, cell handling and inoculation protocols, as well as the depth of the suspension in each well are important considerations in the use of the present invention with some cells and BACs.

For some cells and BACs, the particular redox dye used is an important consideration. Thus, the dye concentration and the type of dye used is assessed and optimized. For example, in some tests, INT (Sigma) is a good redox dye, while in other tests, a dye such as MTT (Sigma), MTS (Promega), XXT (Sigma), PDTPT (Dojindo), WST-1 (Dojindo), WST-4 (Dojindo), WST-5 (Dojindo), WST-8 (Dojindo), redox purple (Biolog), or Alamar blue (Trek) work better.

In still other test systems, intermediate electron carriers are evaluated and optimized. For example, the use of menadione, menadione bisulfite, meldola's blue, PES, PMS, and methoxy-PMS is analyzed.

The evaluation and optimization of gels and cationic gel-inducers in gelling systems is another factor. Thus, the magnesium, calcium, and/or strontium concentrations, etc., are assessed, as is the concentration of gelling agent (e.g., 0 to 0.05% gellan gum). In some embodiments, surfactant(s) are also included in the inoculating fluid. Thus, in these embodiments, the type and concentration (e.g., 0.02% to 0.2%) are additional factor that requires attention in some testing systems. For example, pluronic F-68 is determined to be suitable for some tests, while Tween-20, Tween-40, or Tween-80 may be found to work better for other tests. In some testing systems, no surfactants are utilized in order to provide an optimal testing system.

In further evaluation, optimization of additional inoculating fluid components is conducted. For example, the concentration and source of FBS is also optimized for the testing system and cells, as is the type of cell culture medium used. The concentration of FBS (0 to 10%), yeast extract (0 to 0.2%), hormones (e.g., fibronectin, transferrin, insulin, steroids, polypeptide growth factors, etc.) is optimized. In addition, evaluation of the testing system using inoculating fluid containing antimicrobials (e.g., penicillin, streptomycin, etc.) is compared to the testing system using inoculating fluid without antimicrobials. The inclusion and concentration of other components, such as nitrogen sources (e.g., glutamine, alanyl-glutamine, and glycyl-glutamine), sulfur sources (e.g., cysteine, methionine, etc.), mineral and/or inorganic nutrients (e.g., ferric citrate, and KCl), purines, pyrimidines, nucleotides, nucleosides, etc., are also assessed and optimized.

In some testing systems, anti-oxidant(s) (e.g., pyruvate, thioglycolate, polyvinyl alcohol, polyvinyl pyrollidone) are desirable. Thus, the testing system is optimized for the type and concentration of antioxidant(s). Evaluation and optimization of carbon dioxide/bicarbonate and the pH are also conducted. For example, the buffer (e.g., HEPES, MOPS, MES, triethanolamine, imidazole, etc.), and $CO_2$ source (e.g., 0 to 0.3% bicarbonate, oxalacetate, etc.) are analyzed. The incubation conditions are likewise optimized for the cell and testing system. For example, in some cases, 10% $CO_2$ is preferred, while in others, 5%, 6%, or a different $CO_2$ percentage works better. The use of pre-conditioned medium is also preferred in some testing systems.

Plate sealing methods and compositions are also optimized. For example, different sealing materials of differing thicknesses find use with different testing systems. In some cases, polyester sealant is preferred, while in others, polyethylene, polyurethane, or other materials are preferred.

In addition, the testing system is optimized for the cell type utilized. For example, some systems work best with adherent cell cultures, while other systems work better with suspension cell cultures. The same considerations apply for cells obtained from different organs/tissues.

Example 25

Preliminary Testing of Media

In this Example, preliminary tests on media without cells are described.
Preliminary Tests In preliminary tests, media containing FBS were tested, in order to determine whether tetrazolium reduction would occur without the presence of cells. It is well known to those in the art that there is a significant problem in using tetrazolium in testing methods with human cells, as FBS gives a background level of tetrazolium reduction that must be subtracted from the result values and calculations.

Thus, FBS was added at 1%, 2%, 4%, 6%, 8%, and 10% levels into the modified IF-h medium prepared as described in Examples 22 and 23, except that the tetrazolium dye used was 50 µg/ml INT. The results were surprising in that no noticeable tetrazolium reduction was observed in the medium without cells, even after 24 hours of incubation in a $CO_2$ incubator at 37° C. Although an understanding of the mechanisms is not necessary in order to use the present invention, it is believed that the substitution of INT for MTT (i.e., a commonly used redox indicator), the absence of any intermediate electron carrier, and/or the omission the riboflavin led to this beneficial result.

Example 26

Testing of IMR-90 Cells in PM1a Testing Plates

IMR-90 cells were cultured in DMEM in 150 mm diameter petri dishes to near confluence under suitable conditions (e.g., 5% $CO_2$, at 37° C.). The cells were harvested from 19 petri dishes, using the standard trypsin-EDTA procedure to detach the cells (i.e., 5 minute treatment with trypsin-EDTA), pooled and centrifuged at 1000×g for 5 minutes at 2-8° C., and resuspended in HBSS without phenol red. The cells were again centrifuged and resuspended in 24 ml inoculating fluid (IF-h). The cell density as determined by measurement using a Coulter Counter was about 3,000,000 cells/ml. Two-fold serial dilutions were prepared using prewarmed inoculating fluid, by mixing 12 ml of cell suspension with 12 ml IF-h, to produce six suspensions having 3,000,000 cells/ml (undiluted), 1,500,000 cells/ml, 750,000 cells/ml, 375,000 cells/ml, 187,500 cells/ml, and 93,750 cells/ml. A "no cell" control was also prepared, using 12 ml inoculating fluid. Each of the cell suspensions was then immediately inoculated into a PM1 a PHENOTYPE MICROARRAY testing panel (Biolog), with about 100 µl of suspension added per well.

After approximately 4.5 hours of incubation at 37° C. in a $CO_2$ incubator, the PHENOTYPE MICROARRAY testing panels were visually examined. The well containing psicose was distinctly more pink than any other well, indicating that the cells were preferentially oxidizing this carbon source. The amount of background pink color was somewhat varied, depending upon the cell concentration. At the highest cell densities, there was a light pink color in all of the wells. The clearest distinction was observed for wells containing the 750,000 cells/ml and 375,000 cells/ml dilutions.

The cells were also microscopically examined. In some wells with certain carbon sources (e.g., glucose, mannose, psicose, and sodium pyruvate), the cells looked healthy and were beginning to attach and spread along the bottom of the well. In other wells with other carbon sources (e.g., sodium malate, and methyl pyruvate), the cells were rounded up and appeared to be stressed. Therefore, different carbon sources clearly had a differential effect on cellular morphology.

After 24 hours of incubation, the PHENOTYPE MICROARRAY testing panels were again visually examined. The wells containing glucose, mannose, and lactose showed a distinctly darker clump of red cells in the center of the wells, again suggesting differential metabolism. Other wells had a light pink background color.

The cells were also microscopically examined after 24 hours of incubation. At this point, the cells looked unhealthy in all of the wells, as they were rounded and in clumps. It appeared that there were far too many cells in each well for the cells to maintain a state of continued health and viability. Thus, it is contemplated that the methods will work better by inoculating the testing panels with healthy cells at a density of about 10,000 to 30,000 cells/ml (i.e., about 1,000 to 3,000 cells/well).

Example 27

Testing HL-60 Cells in PM1 and PM2 Plates

In this Example, methods for testing unattached cells for their ability to use multiple carbon sources are described. The human acute promyelocytic leukemia cell line known as HL-60 (Collins et al., Nature, 270:347-349 [1977]) was chosen for this experiment. However, this application is not intended to be limited to the use of HL-60 cells, leukemia cells or even human cells.

HL-60 cells were grown in Falcon tissue culture flasks with vented tops. The culture medium used was RPMI 1640 medium (Invitrogen 11875) with 2 g/L glucose, 2 mM L-glutamine, 2 g/L sodium bicarbonate, 5 mg/L phenol red, 50 U/mL penicillin, 50 µg/mL streptomycin, and 10% (v/v) heat inactivated fetal bovine serum (HI FBS, Invitrogen 16140). The cells were seeded at $2\times10^5$/mL and used 3 days after culture initiation. During all incubations, the cells were kept in an atmosphere of 5% $CO_2$, 90-100% humidity, and 37° C. A viable cell count was obtained by trypan blue exclusion and an appropriate volume of the cell suspension (to have 33% more viable cells than was sufficient for the experiment) was placed in a polypropylene centrifuge tube. Cells were pelleted by centrifugation at 350×g for 10 minutes at room temperature. Cells were resuspended in Dulbecco's Phosphate Buffered Saline (D-PBS, Invitrogen 14040) and centrifuged a second time. The washed cells were then resuspended to two-thirds the final volume in Dulbecco's Modified Eagle's Medium (DME, Sigma D5030) containing supplements (See, Table 17) such that the resulting medium was equivalent to RPMI 1640, and including 10% HI FBS, penicillin-streptomycin and sodium bicarbonate, but without D-glucose, L-glutamine, sodium pyruvate, and phenol red. This medium, designated as DME-R, was selected for these experiments as it is an energy-depleted medium that is able to provide adequate nutritional support for the growth of many-mammalian cells when a carbon/energy source is supplemented. An aliquot of the cell suspension was counted by trypan blue exclusion and the cell density was adjusted to $1\times10^6$/mL.

TABLE 17

Additives to DME to Yield DME-R Medium

| Supplement | Volume Added to 100 mL DME (mL) |
|---|---|
| 2X DME (D5030) | 50 |
| penicillin/streptomycin (100X) | 1 |
| L-asparagine (100X) | 1 |
| L-aspartic acid (100X) | 1 |
| hydroxy-L-proline (100X) | 1 |
| L-proline (100X) | 1 |
| L-glutamic acid (100X) | 1 |
| reduced glutathione (1000X) | 0.1 |
| PABA (1000X) | 0.1 |
| vitamin B12 (1000X) | 0.1 |
| biotin (2000X) | 0.05 |
| water | to 100 mL |

Fifty µL of DME-R were added to each well of the appropriate number PM1 and PM2 PHENOTYPE MICROARRAY testing panels (half area, 96-well MICROPLATES, commercially available from Biolog). The cells were plated at a volume of 50 µL/well, giving a final cell density of $5\times10^4$/well. For each plate containing chemicals and cells, a second, control plate containing only chemicals and medium (total volume 100 µL/well) was prepared. The cells were assayed for growth by addition of a calorimetric reagent. Five µL of the colorimetric reagent was added to each well after 1 hour incubation at 5% $CO_2$, 90-100% humidity, and 37° C. The colorimetric reagent termed MTS/MPMS, contained 2 mg/mL 3-(4,5-dimethylthiazol-2-yl)-5-(3-carboxymethoxyphenyl)-2-(4-sulfophenyl)-2H-tetrazolium, inner salt (MTS), and 0.2 mM 1-methoxy-phenazine methosulfate (MPMS), giving a final concentration in each well of 0.1 mg/mL MTS (0.2 mM), and 0.01 mM 1-methoxy-PMS. The color formed in each well after a 24 hour incubation period, was measured on a plate reader at 490 nm with a reference wavelength of 650 nm, to minimize background. Optical density (OD) values from the control plate were subtracted from the OD values obtained with cells prior to normalizing the data to % negative control (cells without added chemicals). The results obtained for the PM 1 MICROPLATE are provided as Table 18 to illustrate the range of data observed in this embodiment of the present invention, while specific results obtained using this method are discussed in more detail below.

Cells remained viable with a 24 hour culture period in the presence of the colorimetric reagent. Several chemicals that produced exorbitantly high backgrounds (e.g., some pentoses, including but not limited to ribose, xylose, arabinose, and lyxose) were excluded from the analysis. Chemicals in the PM 1 microplate which produced a positive response greater than 130% of the negative (no energy source) control included: D-serine, glucose-6-phosphate, L-asparagine, L-glutamine, D-gluconic acid, D-galactonic acid γ lactone, glucose-1-phosphate, α-hydroxy-glutaric acid γ lactone, L-alanyl-glycine, β-methyl-D-glucoside, pyruvic acid, lactic acid, mono-methyl-succinate, glycyl-L-glutamate, D-galacturonic acid, thymidine, and inosine.

TABLE 18

Response of HL-60 Cells to the Carbon Sources of PM1

| Row. | \multicolumn{12}{c}{Column} |
|---|---|---|---|---|---|---|---|---|---|---|---|---|

| Row. | 1 | 2 | 3 | 4 | 5 | 6 | 7 | 8 | 9 | 10 | 11 | 12 |
|---|---|---|---|---|---|---|---|---|---|---|---|---|
| A | 100 | u | 51 | u | 102 | 59 | 64 | 90 | 97 | 95 | 91 | 81 |
| B | 195 | 128 | 123 | 122 | 118 | 136 | 126 | 6 | 190 | 79 | 102 | 120 |
| C | 151 | 184 | 126 | 57 | u | u | 114 | 34 | 130 | 92 | 120 | 148 |
| D | 178 | 51 | 40 | 56 | u | 63 | u | 84 | 44 | 55 | 73 | 60 |
| E | 235 | 120 | 153 | 89 | u | 142 | 120 | 142 | 128 | 137 | 77 | 126 |
| F | 96 | 64 | 66 | 91 | 45 | 32 | u | 73 | 30 | u | 18 | 155 |
| G | 145 | 96 | 102 | 109 | 124 | 141 | u | 86 | 157 | 49 | 45 | 43 |
| H | 94 | 32 | 40 | u | u | 11 | u | 444 | 224 | 176 | 35 | 33 |

*Results shown as a percentage of that observed for the negative control wells.
u indicates wells in which a net negative O.D. was measured.

Chemicals in the PM 2 MICROPLATE which produced a positive response greater than 130% of the negative (no energy source) control included: glycogen, inulin, chondroitin sulfate C, L-arginine, L-valine, L-histidine, γ-amino butyric acid, β-hydroxy-butyric acid, hydroxy-L-proline, L-isoleucine, L-homoserine, succinamic acid, lactitol, D-lactic acid methyl ester, L-tartaric acid, L-alaninamide, acetamide, 3-hydroxy-2 butanone, 2,3-butanediol, melibionic acid, L-pyroglutamic acid, D-ribono-1,4-lactone, and α-methyl-D-galactoside. As expected, L-glutamine (13.7 mM, PM/well E1) produced a strong positive response, while citric acid (10.4 mM, PM/well F2) produced an inhibitory response (Marsili et al., Riv. Biol. 93:175-181 [2000]). These results validate the assay design, as these results are comparable to that obtained by addition of the chemicals in the fluid phase. Of special interest was the unexpected detection of increased metabolic activity of HL-60 in the presence of lactone containing chemicals.

Example 28

Testing Responses of HL-60 Cells to a Selected Set of Compounds from PM1 and PM2 Plates at a Range of Concentrations In this Example, methods for testing unattached cells for their ability to use various concentrations of selected carbon sources are described. The carbon sources used in this Example were identified by the methods disclosed in Example 27. Similarly, HL-60 cells were cultured as described in Example 27.

After washing, HL-60 cells were resuspended in DME-R. An aliquot of the cell suspension was counted by trypan blue exclusion and the cell density was adjusted to $6.67 \times 10^5$/mL. Fifty μL of DME-R were added to each well of the appropriate number of half area, 96-well plates, followed by 23 μL of the appropriate dilution of each test energy source. Stocks of 133 mM of each test chemical were prepared in tissue culture grade water, sterile filtered, and dilutions were prepared in a master plate so that, upon dilution in a total volume of 150 μL, the final concentrations would be 0.033 to 20 mM. Negative control wells received 23 μL of tissue culture grade water. The cells were plated at a volume of 75 μL/well, giving a final cell density of $5 \times 10^4$/well. For each plate containing energy sources and cells, a second, control plate containing only energy sources was prepared. Plates were incubated at 5% $CO_2$, 90-100% humidity, and 37° C. for 24 hours prior to addition of the MTS/MPMS colorometric reagent (7.5 μL/well). The color formed in each well after an additional 24 hour incubation period, was measured on a plate reader at 490 nm with a reference wavelength of 650 nm. OD values from the control plate were subtracted from the OD values obtained with cells prior to normalizing the data to % negative control (cells without added energy source).

Of the chemicals selected for retesting, all but hydroxy-L-proline induced a response of at least 30% greater than the negative control wells, as shown in Table 19. Those energy sources inducing a response of at least 40% greater than the negative control were scored as inducing a positive response, and included: L-asparagine, D-galactonic acid-γ-lactone, L-galactonic acid-γ-lactone, D galacturonic acid, L-histidine, and mono-methyl succinate. Mono-methyl succinate was the best stimulator, although it was less effective at lower concentrations than L-glutamine, the energy source that has been used for HL-60 cells (Dass et al., In Vitro, 20:869-875 [1984]). At 15 and 20 mM, responses to the chemicals declined. Unexpectedly, the concentrations at which various carbon sources could be utilized varied. For instance, some amino acids (e.g., glutamine, arginine, and asparagine) were strongly utilized, even at very low concentrations (e.g., 0.03 mM), whereas others (e.g., histidine and valine) were not. All positive responses were observed when the energy sources were used in the 1 to 3.3 mM range, while some chemicals also induced responses at concentrations in the range of 0.033 to 10 mM. Thus, there are interesting and perhaps important differences in the ability of various cell lines to transport and utilize these chemicals. The invention herein described provides an excellent technology for detecting and measuring these differences.

TABLE 19

HL-60 Cell Responses to Selected Compounds from PM1 and PM2

| | Energy Source | | | | | | | | | | |
|---|---|---|---|---|---|---|---|---|---|---|---|
| Conc. (mM). | L-glutamine | L-arginine | L-asparagine | D-gal acid g-lactone | L-gal acid g-lactone | D-galacturonic acid | L-histidine | hydroxy L-proline | mono methyl succinate | thymidine | L-valine |
| 20 | 92.0 | 109.3 | 117.8 | 93.9 | 100.4 | 25.0 | 95.0 | 99.2 | 93.3 | 68.5 | 112.4 |
| 15 | 127.1 | 107.6 | 128.5 | 122.2 | 125.0 | 101.2 | 122.8 | 111.8 | 139.0 | 91.5 | 122.0 |
| 10 | 151.4 | 127.7 | 136.7 | 127.1 | 122.8 | 121.9 | 119.8 | 121.5 | 173.3 | 105.7 | 124.7 |
| 3.3 | 160.8 | 131.7 | 135.0 | 142.2 | 141.5 | 140.3 | 145.9 | 129.6 | 166.7 | 129.1 | 133.2 |
| 1.00 | 168.1 | 137.5 | 148.9 | 141.4 | 145.0 | 138.2 | 135.2 | 128.4 | 141.8 | 133.9 | 135.2 |
| 0.33 | 162.5 | 130.6 | 137.7 | 129.3 | 132.4 | 126.4 | 127.8 | 121.5 | 132.9 | 127.6 | 133.5 |
| 0.10 | 160.9 | 138.2 | 149.2 | 128.7 | 132.3 | 124.9 | 121.4 | 122.8 | 130.4 | 125.2 | 136.6 |
| 0.03 | 147.2 | 133.7 | 134.4 | 128.3 | 129.3 | 123.7 | 122.8 | 125.0 | 118.4 | 121.1 | 117.2 |

*Results shown as a percentage of that observed for the negative control wells.

Example 29

Testing Responses of HL-60 in PM1a, PM6, PM7 and PM8 Plates

In this Example, methods for testing unattached cells for their ability to use various carbon sources including di and tri-peptides are described. HL-60 cells were cultured as described in Example 27.

After washing, HL-60 cells were resuspended in DME-R. An aliquot of the cell suspension was counted by trypan blue exclusion and the cell density was adjusted to $1 \times 10^6$/mL. Fifty µL of DME-R were added to each well of the appropriate number of half area, 96-well plates. The cells were plated at a volume of 50 µL/well, giving a final cell density of $5 \times 10^4$/well. PM1a, MP6, PM7, and PM8 MICROPLATE testing plates were inoculated (these MICROPLATE testing plates are available from Biolog under license). For each plate containing chemicals and cells, a second, control plate containing only chemicals was prepared. All wells contained a total volume of 100 µL. Plates were incubated at 5% $CO_2$, 90-100% humidity, and 37° C. for 1 hour prior to addition of the MTS/MPMS colorometric reagent (5 µL/well). The color formed in each well after an additional 24 hour incubation period, was measured on a plate reader at 490 nm with a reference wavelength of 650 nm. OD values from the control plate were subtracted from the OD values obtained with cells prior to normalizing the data to % negative control (cells without added energy source).

Chemicals giving a positive response in PM1A (greater than 130% of the negative control) included: L-glutamine, L-alanyl-glycine, L-galactonic acid γ-lactone, and mono-methyl succinate. Peptides giving a positive response in PM6 included: cys-gly, gly-val, gly-gly, his-asp, ile-gln, and gly-his. Peptides giving a positive response in PM7 included: pro-ala, ser-phe, ser-leu, ser-met, thr-met, thr-pro, tyr-phe, and tyr-ala. Lastly, peptides giving a positive response in PM8 included: D-ala-D-ala, gln-glu, gly-gly-ile, gly-gly-leu, gly-D-ser, gly-D-val, ala-gln, his-his, phe-asp, pro-trp, thr-ser, tyr-val, val-gln, and val-tyr-val. Several dipeptides and tripeptides contained amino acids that had shown a positive effect as individual amino acids, namely: D-serine, L-glutamine, L-valine, L-histidine, L-isoleucine, and L-asparagine. Unexpectedly, this assay detected positive responses to peptides containing L-phenylalanine, L-proline, L-threonine, or D-alanine. This is unexpected given that as individual amino acids, a significant response by HL-60 cells was not observed.

Example 30

Testing Responses of HepG2 Cells Cultured on Flat Bottom Plastic Wells in PM1 and PM2 Plates In this Example, methods for testing adherent cells for their ability to use multiple carbon sources are described. The human hepatocellular carcinoma cell line known as HepG2 (Knowles et al., Science, 209:497-499 [1980]) was chosen for this experiment. However, this application is not intended to be limited to the use of HepG2 cells, hepatocytes, carcinoma cells or even human cells.

HepG2 cells were grown in Falcon tissue culture flasks with vented tops. The culture medium used was Minimal Essential medium (MEM, Invitrogen 11095) with 1 g/L glucose, 2 mM L-glutamine, 2.2 g/L sodium bicarbonate, 10 mg/L phenol red, and supplemented with 0.1 mM Nonessential Amino Acids, 1 mM sodium pyruvate, 50 U/mL penicillin, 50 µg/mL streptomycin, and 10% (v/v) heat inactivated fetal bovine serum (HI FBS, Invitrogen 16140). The cells were seeded at $2 \times 10^4$/cm$^2$ and used 3 days after initiation of culture. During all incubations, the cells were kept in an atmosphere of 5% $CO_2$, 90-100% humidity, and 37° C. Cells were harvested by trypsinization for 3 minutes in 0.25% trypsin-1 mM EDTA and resuspended in an equal volume of culture medium. A viable cell count was obtained by trypan blue exclusion and an appropriate volume of the cell suspension (to have 33% more viable cells than was sufficient for the experiment) was placed in a polypropylene centrifuge tube. Cells were pelleted by centrifugation at 350×g for 10 minutes at room temperature, resuspended in Dulbecco's Phosphate Buffered Saline (D-PBS, Invitrogen 14040) and centrifuged a second time. Cells were then resuspended to two-thirds the final volume needed in Dulbecco's Modified Eagle's Medium (DME, Sigma D5030) containing 10% HI FBS and penicillin-streptomycin but without glucose, L-glutamine, sodium pyruvate, and phenol red. An aliquot was counted by trypan blue exclusion and the cell density was adjusted to $1.28 \times 10^5$/mL. Cells were plated in 100 µL/well in wells of standard, 96-well plates ($4 \times 10^4$ cells/cm$^2$) and allowed to adhere overnight prior to addition of test chemicals.

For assay, the culture medium was aspirated, the wells were washed once with D-PBS and 170 µL of DME were added to each well, followed by 30 µL of the appropriate dilution of each test energy source. Stocks of 133 mM of each test chemical were prepared in tissue culture grade water, sterile filtered, and dilutions were prepared in a master plate so that, upon dilution into a regular 96-well MICROPLATE a total well volume of 200 µL, the final concentrations would be 0.033 to 20 mM. Negative control wells received 30 µL of tissue culture grade water. For each plate containing energy sources and cells, a second, control plate containing only energy sources was prepared. Plates were incubated at 5% $CO_2$, 90-100% humidity, and 37° C. for 48 to 72 hours prior to addition of the MTS/PMS colorometric reagent (10 µL/well). The color formed in each well 4-24 hours after addition of the calorimetric reagent, was measured with a plate reader at 490 nm with a reference wavelength of 650 nm. OD values from the control plate were subtracted from the OD values obtained with cells prior to normalizing the data to % negative control (cells without added energy source).

OD values after a 4 hour color development period were low, but increased to 0.8 to 1.2 after a 20 hour incubation period. L-glutamine produced a dose dependent response in the 72 hour culture up to 3.3 mM (See, Table 20) which was not observed at the earlier time points. In fact, most of the chemicals tested were stimulatory to HepG2 cells, with increasing time in culture increasing both the magnitude and sensitivity of the response. Comparison of these responses to those obtained with HL-60 cells cultured in the presence of the same chemicals, demonstrated that the two cell lines respond somewhat differently to the array (e.g., the response to 0.03 mM L-glutamine and the response to 20 mM L-galactonic acid γ lactone), although mono-methyl succinate was observed to induce the greatest response from both cell types. Here again, a differential response to various carbon sources was observed to be concentration dependent.

Surprisingly, with the HepG2 cells, some chemicals gave the strongest response at 15 mM. This concentration was above the optimal concentration for HL-60 cells. These data again show the usefulness of testing a range of chemical concentrations.

a 50 mL tube, and the volume adjusted to 5 mL. Cells were allowed to attach for 1 hour in an atmosphere of 5% $CO_2$, 90-100% humidity, and 37° C., with resuspension every 15 minutes. The microcarriers were transferred to a 100×15 mm Petri dish in a total volume of 20 mL. Cultures were maintained as stationary cultures until used for assay.

The thixotropic suspending agent, methylcellulose (1500 cps, Sigma M0555), was included in the medium to keep the microcarriers suspended so that they could be accurately pipetted. The methylcellulose was prepared by autoclaving in 20 mL tissue culture water for 30 minutes, then mixing by shaking for 1 hour. The initial concentration of methylcellulose was 3%. The methylcellulose was then diluted 1:1 in 2× DME with or without glucose, then supplemented with 10% HI FBS; this yields a methylcellulose concentration of 1.36%. Beads were transferred to a 50 mL tube, allowed to settle and resuspended in DPBS. The washed beads were then resuspended in DME with 10% HI FBS and penicillin-streptomycin but without glucose, L-glutamine, sodium pyruvate, or phenol red. An equal volume of 1.36% methylcellulose was added and mixed by pipetting.

For the assay, 70 µL of DME with 10% HI FBS and penicillin-streptomycin but without glucose, L-glutamine, sodium pyruvate, or phenol red were added to each well, followed by 30 µL of the appropriate dilution of each test energy source. Stocks of 133 mM of each test chemical were prepared in tissue culture grade water, sterile filtered, and dilutions were prepared in a master plate so that, upon dilution into a regular 96-well MICROPLATE a total well volume

TABLE 20

HepG2 Cells Responses After 72 hours in Culture and a 4 hour Color Development Period

| Conc. (mM). | Energy Source | | | | | | | | | | |
|---|---|---|---|---|---|---|---|---|---|---|---|
| | L-glutamine | L-arginine | L-asparagine | D-gal acid g-lactone | L-gal acid g-lactone | D-galacturonic acid | L-histidine | hydroxy L-proline | mono methyl succinate | thymidine | L-valine |
| 20 | 110.6 | 60.3 | 52.2 | 207.6 | 231.2 | 161.6 | 72.1 | 62.8 | 237.5 | 134.3 | 87.6 |
| 15 | 145.5 | 90.8 | 112.5 | 239.3 | 215.1 | 228.1 | 195.2 | 101.3 | 357.4 | 101.3 | 108.2 |
| 10 | 224.4 | 119.3 | 124.3 | 178.4 | 181.5 | 179.0 | 210.1 | 123.1 | 224.4 | 114.4 | 131.8 |
| 3.3 | 260.5 | 153.5 | 161.0 | 157.3 | 172.8 | 164.7 | 180.3 | 126.8 | 199.5 | 134.9 | 176.5 |
| 1.00 | 218.2 | 142.3 | 172.8 | 162.9 | 164.1 | 177.2 | 147.9 | 140.5 | 179.6 | 149.8 | 124.9 |
| 0.33 | 205.1 | 165.3 | 203.3 | 164.7 | 196.4 | 170.9 | 173.4 | 162.2 | 179.0 | 180.3 | 170.3 |
| 0.10 | 114.4 | 143.6 | 190.2 | 142.3 | 127.4 | 139.9 | 142.3 | 139.9 | 161.0 | 157.9 | 148.6 |
| 0.03 | 103.2 | 127.4 | 121.8 | 111.3 | 121.2 | 123.7 | 124.9 | 97.0 | 143.6 | 115.0 | 119.3 |

*Results shown as a percentage of that observed for the negative control wells.

Example 31

Testing Responses of HepG2 Cells Cultured on Microcarriers to Various Energy Sources In this Example, methods for testing adherent cells cultured in suspension, for their ability to use multiple carbon sources are described. HepG2 cells were cultured as described in Example 30.

HepG2 cells were harvested by trypsinization for 3 minutes in 0.25% trypsin-1 mM EDTA and resuspended in an equal volume of culture medium. A viable cell count was obtained by trypan blue exclusion and the appropriate volume of the cell suspension to have $2.7 \times 10^6$ cells/0.1 gm CYTODEX 3 (Sigma C3275) microcarrier beads was determined. Microcarrier beads had been previously prepared by 1) rehydration in calcium-magnesium free (CMF) DPBS for 3 hours, 2) autoclaving for 15 minutes, and 3) washing twice in MEM without serum. The cell suspension was added to the beads in of 200 µL, the final concentrations would be 0.033 to 20 mM. Negative control wells received 30 µL of tissue culture grade water. One hundred µL of beads were pipetted into each well. For each plate containing energy sources and cells, a second, control plate containing only energy sources was prepared. Plates were incubated at 5% $CO_2$, 90-100% humidity, and 37° C. for 68 hours prior to addition of the MTS/MPMS colorometric reagent (10 µL/well). The color formed in each well 4-8 hours after addition of the colorimetric reagent, was measured with a plate reader at 490 nm with a reference wavelength of 650 nm. OD values from the control plate were subtracted from the OD values obtained with cells prior to normalizing the data to % negative control (cells without added energy source).

As shown in Table 21, HepG2 cells seeded onto CYTODEX 3 microcarriers 24 hours before exposure to different energy sources, show a narrow range of responsiveness to select carbon sources (e.g., L-glutamine and mono-methyl succinate). Responses greater than 140% of the negative control were scored as positive responses.

TABLE 21

Responses of HepG2 Cells Cultured on Microcarriers
After 68 hours in Culture and a 4 hour Color Development Period

| | Energy Source | | | | | | | | | |
|---|---|---|---|---|---|---|---|---|---|---|
| Conc. (mM). | citric acid | fructose | galactose | glucose | glutamine | myoinositol | sucrose | uridine | thymidine | methyl succinate | D-gal acid g-lactone |
| 20 | 20.3 | 50.3 | 65.6 | 50.3 | 100.9 | 61.4 | 59.5 | 31.9 | 34.5 | 112.4 | 74.1 |
| 15 | 31.5 | 72.1 | 81.0 | 84.0 | 150.1 | 78.3 | 66.8 | 74.1 | 65.2 | 181.5 | 98.6 |
| 10 | 46.8 | 94.4 | 94.4 | 110.5 | 182.7 | 89.0 | 83.3 | 94.8 | 71.4 | 162.7 | 95.2 |
| 3.3 | 131.3 | 106.7 | 116.7 | 132.4 | 211.8 | 108.2 | 94.0 | 106.3 | 89.0 | 124.3 | 101.7 |
| 1.00 | 115.9 | 114.7 | 109.0 | 122.0 | 210.7 | 99.8 | 95.2 | 108.6 | 99.4 | 107.5 | 89.4 |
| 0.33 | 111.7 | 123.2 | 121.3 | 125.9 | 194.6 | 112.8 | 98.6 | 99.0 | 97.9 | 98.6 | 89.0 |
| 0.10 | 111.3 | 107.8 | 110.9 | 112.4 | 151.2 | 109.8 | 109.4 | 109.0 | 101.3 | 83.3 | 100.2 |
| 0.03 | 102.9 | 97.1 | 97.1 | 96.3 | 110.1 | 86.3 | 90.2 | 102.1 | 87.9 | 90.6 | 99.4 |

*Results shown as a percentage of that observed for the negative control wells.

Example 32

Energy Source Utilization by DMSO Differentiated HL-60 Cells

In this Example, methods for testing in vitro-differentiated cells for their ability to use multiple energy sources are described. Prior to differentiation, HL-60 cells were cultured as described in Example 27. DMSO-induced differentiation (Odani et al., Res. Commun. Mol. Pathol. Pharmacol. 108: 381-391 [2000]; and Yamaguchi et al., Biol. Pharm. Bull. 20:943-947 [1997]) was accomplished by incubation of the cells in the presence of 1.25% DMSO for 3 days.

After washing, HL-60 cells were resuspended in DME-R. An aliquot of the cell suspension was counted by trypan blue exclusion and the cell density was adjusted to $6.67 \times 10^5$/mL. Fifty μL of DME-R were added to each well of the appropriate number of half area, 96-well plates, followed by 25 μL of the appropriate dilution of each test energy source. Stocks of 133 mM of each test chemical were prepared in tissue culture grade water, sterile filtered, and dilutions were prepared in a master plate so that, upon dilution into a half-area 96-well microtiter plate to a total well volume of 150 μL, the final concentrations would be 0.033 to 20 mM. Negative control wells received 25 μL of tissue culture grade water. The cells were plated at a volume of 75 μL/well, giving a final cell density of $5 \times 10^4$/well. For each plate containing energy sources and cells, a second, control plate containing only energy sources was prepared with the same total volume of liquid (148 μL/well). Plates were incubated at 5% $CO_2$, 90-100% humidity, and 37° C. for 24 hours prior to addition of the MTS/MPMS calorimetric reagent (7.5 μL/well). The color formed in each well 24 hours after addition of the colorimetric reagent, was measured with a plate reader at 490 nm with a reference wavelength of 650 nm. OD values from the control plate were subtracted from the OD values obtained with cells prior to normalizing the data to % negative control (cells without added energy source).

TABLE 22

Energy Use by Undifferentiated HL-60 Cells

| | Energy Source | | | | | | | | | | |
|---|---|---|---|---|---|---|---|---|---|---|---|
| Conc. (mM). | L-glutamine | L-arginine | L-asparagine | D-gal acid g-lactone | L-gal acid g-lactone | D-galacturonic acid | L-histidine | hydroxy L-proline | mono methyl succinate | thymidine | L-valine |
| 20 | 171.7 | 125.9 | 156.7 | 125.0 | 126.2 | 112.8 | 103.6 | 101.8 | 198.7 | 52.3 | 103.9 |
| 15 | 198.2 | 140.4 | 152.6 | 147.5 | 163.4 | 162.3 | 149.1 | 124.2 | 260.6 | 81.3 | 97.7 |
| 10 | 220.2 | 131.5 | 141.0 | 136.7 | 153.0 | 134.3 | 143.7 | 117.8 | 222.8 | 80.3 | 89.0 |
| 3.3 | 248.6 | 114.9 | 135.6 | 152.6 | 160.8 | 143.6 | 161.9 | 114.7 | 182.2 | 110.8 | 86.4 |
| 1.00 | 237.4 | 108.6 | 124.2 | 133.2 | 137.0 | 141.4 | 118.1 | 104.7 | 141.3 | 90.9 | 78.6 |
| 0.33 | 227.0 | 114.0 | 117.5 | 125.3 | 132.9 | 116.0 | 104.7 | 99.6 | 112.5 | 101.2 | 83.8 |
| 0.10 | 214.1 | 117.5 | 118.3 | 127.4 | 125.9 | 116.3 | 116.9 | 112.9 | 99.9 | 106.4 | 93.2 |
| 0.03 | 166.8 | 124.5 | 127.7 | 122.7 | 117.0 | 116.0 | 119.3 | 109.9 | 104.2 | 84.1 | 89.6 |

*Results shown as a percentage of that observed for the negative control wells.

TABLE 23

Energy Use by DMSO-Differentiated HL-60 Cells

| | Energy Source | | | | | | | | | | |
|---|---|---|---|---|---|---|---|---|---|---|---|
| Conc. (mM). | L-glutamine | L-arginine | L-asparagine | D-gal acid g-lactone | L-gal acid g-lactone | D-galacturonic acid | L-histidine | hydroxy L-proline | mono methyl succinate | thymidine | L-valine |
| 20 | 109.0 | 93.4 | 134.5 | 99.2 | 98.1 | 101.0 | 114.5 | 92.0 | 118.1 | 103.4 | 88.6 |
| 15 | 121.1 | 119.3 | 152.2 | 130.4 | 131.1 | 125.5 | 140.4 | 109.0 | 155.5 | 159.9 | 81.4 |

TABLE 23-continued

Energy Use by DMSO-Differentiated HL-60 Cells

| | | | | | | Energy Source | | | | | |
|---|---|---|---|---|---|---|---|---|---|---|---|
| Conc. (mM). | L-glutamine | L-arginine | L-asparagine | D-gal acid g-lactone | L-gal acid g-lactone | D-galacturonic acid | L-histidine | hydroxy L-proline | mono methyl succinate | thymidine | L-valine |
| 10 | 157.0 | 132.4 | 166.9 | 166.9 | 171.1 | 172.6 | 171.1 | 126.9 | 193.5 | 160.2 | 89.3 |
| 3.3 | 171.8 | 122.9 | 153.1 | 185.9 | 178.2 | 167.8 | 171.5 | 129.0 | 183.8 | 173.4 | 81.2 |
| 1.00 | 156.5 | 125.9 | 143.1 | 157.1 | 155.4 | 157.0 | 156.7 | 121.9 | 142.2 | 164.7 | 86.7 |
| 0.33 | 153.6 | 121.6 | 122.2 | 133.3 | 137.5 | 138.0 | 127.5 | 120.5 | 124.5 | 143.3 | 85.2 |
| 0.10 | 149.4 | 103.4 | 111.9 | 122.9 | 129.2 | 123.4 | 123.4 | 110.5 | 93.4 | 111.5 | 89.4 |
| 0.03 | 110.0 | 105.8 | 106.2 | 111.9 | 113.9 | 117.7 | 119.0 | 102.8 | 103.7 | 96.0 | 81.1 |

*Results shown as a percentage of that observed for the negative control wells.

Surprisingly, there were clearly detectable differences in the metabolism of DMSO-differentiated cells as compared to their undifferentiated counterparts. Undifferentiated HL-60 cells, but not DMSO-differentiated HL-60 cells, were responsive to high concentrations of L-glutamine (e.g., greater than 10 mM). In contrast, differentiated HL-60 cells were able to utilize thymidine at concentrations of 0.1-15 mM while undifferentiated HL-60 cells were not. As shown in Tables 22 and 23, profiles for the two populations of cells were similar in most other respects.

Example 33

Affects of Citric Acid on Energy Utilization by HL-60 Cells

In this Example, methods for testing biologically active chemical (BAC)-induced modulation of cell activity are described. The BAC selected for this Example is the small acidic peptidomimetic, citric acid, which is known to have antiproliferative effects (Marsili et al., Riv. Biol. 93:175-181 [2000]). However, this application is not intended to be limited to the use of citric acid, peptidomimetics, or even growth inhibitors, and in fact is contemplated to have utility for any BAC. HL-60 cells were cultured as described in Example 27.

After washing, HL-60 cells were resuspended in DME-R. An aliquot of the cell suspension was counted by trypan blue exclusion and the cell density was adjusted to $6.67 \times 10^5$/mL. Fifty μL of DME-R with or without 30 mM citric acid (final concentration, 10 mM) were added to each well of the appropriate number of half area, 96-well plates, followed by 25 μL of the appropriate dilution of each test energy source. Stocks of 133 mM of each test chemical were prepared in tissue culture grade water, sterile filtered, and dilutions were prepared in a master plate so that, upon dilution in a total volume of 150 μL, the final concentrations would be 0.033 to 20 mM. Negative control wells received 25 μL of tissue culture grade water. The cells were plated at a volume of 75 μL/well, giving a final cell density of $5 \times 10^4$/well. For each plate containing energy sources and cells, a second, control plate containing only energy sources was prepared. Plates were incubated at 5% $CO_2$, 90-100% humidity, and 37° C. for 24 hours prior to addition of the MTS/MPMS calorimetric reagent (7.5 μL/well). The color formed in each well 24 hours after addition of the colorimetric reagent, was measured with a plate reader at 490 nm with a reference wavelength of 650 nm. OD values from the control plate were subtracted from the OD values obtained with cells prior to normalizing the data to % negative control.

TABLE 24

Effect of 10 mM Citric Acid on HL-60 Energy Utilization

| | | | | | | Energy Source | | | | | |
|---|---|---|---|---|---|---|---|---|---|---|---|
| Conc. (mM). | L-glutamine | L-arginine | L-asparagine | D-gal acid g-lactone | L-gal acid g-lactone | D-galacturonic acid | L-histidine | hydroxy L-proline | mono methyl succinate | thymidine | L-valine |
| 20 | 86.7 | 58.3 | 98.3 | 115.7 | 111.5 | 110.8 | 83.5 | 68.8 | 173.9 | 64.8 | 64.5 |
| 15 | 107.3 | 52.9 | 97.7 | 126.5 | 122.4 | 136.3 | 122.8 | 87.4 | 192.3 | 20.9 | 42.3 |
| 10 | 125.3 | 45.0 | 100.1 | 151.5 | 138.4 | 177.0 | 158.4 | 85.0 | 210.0 | 31.0 | 32.2 |
| 3.3 | 135.0 | 25.9 | 48.6 | 162.8 | 188.9 | 141.6 | 88.2 | 49.0 | 163.6 | 27.9 | 20.8 |
| 1.00 | 108.0 | 17.7 | 24.6 | 63.3 | 38.6 | 61.8 | 33.7 | 37.5 | 51.7 | 22.1 | 12.7 |
| 0.33 | 57.1 | 8.7 | 13.4 | 35.7 | 19.7 | 43.5 | 19.1 | 25.0 | 16.9 | 12.4 | 12.4 |
| 0.10 | 57.8 | 12.1 | 15.3 | 20.9 | 18.2 | 12.8 | 19.4 | 17.7 | 13.0 | 18.9 | 13.4 |
| 0.03 | 15.0 | 7.6 | 10.1 | 9.5 | 16.2 | 1.4 | 12.2 | 7.6 | 4.9 | 5.2 | 9.3 |

*Results shown as a percentage of that observed for the negative control wells.

Data shown in Table 24 are expressed as percent negative control without energy sources and without citric acid. In the presence of citric acid, none of the energy sources at concentrations less than 1 mM were able to provide support for HL-60 growth above 50% of that observed in the negative control well (without citric acid and energy sources). At or above 1 mM, the sensitivity of cells was dependent upon the carbon source. L-glutamine, 1 mM-15 mM, was able to restore cell activity to a level equal or greater than the negative control (without L-glutamine and without citric acid). Mono-methyl succinate (3.3-20 mM) was able to restore cell activity to the level (up to 210% of the control without citric acid) observed in the absence of citric acid, (with mono-methyl succinate). There was also acitivity with D-galacturonic acid, L-histidine, and the lactones, but in a narrower concentration range. These results indicate that only certain chemicals are capable of overcoming the antiproliferative effects of citric acid; specifically D-galactonic acid γ lactone, L-galactonic acid γ lactone, D-galacturonic acid, and mono-methyl-succinate. Unexpectedly, this experiment indicates that cells cultured with various energy sources have a differential sensitivity to citric acid.

L-glutamine seemed to limit the effect to maintenance of the cells at the level seen with no chloramphenicol and no added energy source. Mono-methyl succinate also had a limited protective effect. Chloramphenicol clearly has a different effect on the cells than citrate shown in Example 33.

TABLE 25

Effect of 1 mM chloramphenicol on HL-60 Energy Utilization

| | Energy Source | | | | | | | | | | |
|---|---|---|---|---|---|---|---|---|---|---|---|
| Conc. (mM). | L-glutamine | L-arginine | L-asparagine | D-gal acid g-lactone | L-gal acid g-lactone | D-galacturonic acid | L-histidine | hydroxy L-proline | mono methyl succinate | thymidine | L-valine |
| 20 | 82.1 | 17.5 | 30.2 | 10.5 | 2.4 | −12.8 | 8.4 | 0.6 | 16.2 | 7.3 | 7.5 |
| 15 | 89.0 | 17.1 | 20.9 | 21.1 | 18.0 | 5.0 | 13.1 | 15.7 | 47.8 | 6.0 | 2.6 |
| 10 | 90.0 | 13.0 | 22.9 | 26.5 | 14.5 | 8.4 | 19.1 | 1.7 | 78.1 | 5.8 | 5.5 |
| 3.3 | 85.0 | 9.9 | 12.1 | 12.7 | 3.7 | 7.9 | 13.9 | 4.4 | 43.3 | 8.8 | 4.3 |
| 1.00 | 69.0 | 0.2 | 3.1 | 24.0 | −13.9 | −4.6 | 7.2 | −1.2 | 1.8 | 3.1 | 3.2 |
| 0.33 | 60.6 | 5.8 | 7.6 | 10.1 | 4.3 | −4.6 | 7.3 | 2.6 | 2.6 | 6.4 | 4.0 |
| 0.10 | 39.8 | 6.1 | 17.4 | 14.5 | −8.4 | −2.7 | 4.3 | −5.0 | −2.1 | 5.8 | 4.3 |
| 0.03 | 33.7 | 12.4 | 6.3 | 10.1 | −2.0 | 0.2 | 6.9 | 1.2 | 10.4 | 8.4 | 6.6 |

*Results shown as a percentage of that observed for the negative control wells.

Example 34

Effects of Chloramphenicol on Energy Utilization by HL-60 Cells

In this Example, methods for testing antimicrobial-induced modulation in growth of a cell are described. The antimicrobial selected for this Example is chloramphenicol. However, this application is not intended to be limited to the use of chloramphenicol, translation inhibitors or even antibiotics. HL-60 cells were cultured as described in Example 27.

After washing, HL-60 cells were resuspended in DME-R. An aliquot of the cell suspension was counted by trypan blue exclusion and the cell density was adjusted to $6.67 \times 10^5$/L. Fifty μL of DME-R containing 3 mM chloramphenicol were added to each well of the appropriate number of half area, 96-well plates, followed by 25 μL of the appropriate dilution of each test energy source. Stocks of 133 mM of each test chemical were prepared in tissue culture grade water, sterile filtered, and dilutions were prepared in a master plate so that, upon dilution in a total volume of 150 μL, the final concentrations would be 0.033 to 20 mM. Negative control wells received 25 μL of tissue culture grade water. The cells were plated at a volume of 75 μL/well, giving a final cell density of $5 \times 10^4$/well. For each plate containing energy sources and cells, a second, control plate containing only energy sources was prepared. Plates were incubated at 5% $CO_2$, 90-100% humidity, and 37° C. for 24 hours prior to addition of the MTS/MPMS colorimetric reagent (7.5 μL/well). The color formed in each well 24 hours after addition of the colorimetric reagent, was measured with a plate reader at 490 nm with a reference wavelength of 650 nm. OD values from the control plate were subtracted from the OD values obtained with cells prior to normalizing the data to % negative control.

Data shown in Table 25 are expressed as percent negative control without chloramphenicol. Treatment of HL-60 cells with 1 mM chloramphenicol ($IC_{50}$ concentration for cells in complete medium) resulted in severe reduction in signal in almost all conditions compared to untreated cells. However, Example 35

Testing TK-1 Cells in PM1 and PM2 Plates

In this Example, methods for testing a murine T lymphoma cells (Butcher et al., Eur. J. Immunol., 10:556-561 [1980]), for their ability to use multiple carbon sources are described. The methods used to culture the TK-1 lymphoma cell line were similar to those used to culture HL-60 cells, as described in Example 27.

TK-1 cells were grown in Falcon tissue culture flasks with vented tops. Culture medium was RPMI 1640 medium (Invitrogen 11875) with 4.5 g/L glucose, 2 mM L-glutamine, 1 mM sodium pyruvate, 0.1 mM nonessential amino acids (NEAA), 0.05 mM 2-mercaptoethanol (2ME), 2 g/L sodium bicarbonate, 5 mg/L phenol red, 50 U/mL penicillin, 50 μg/mL streptomycin, and 10% (v/v) heat inactivated fetal bovine serum (HI FBS, Invitrogen 16140). The cells were seeded at $3 \times 10^5$/mL, subcultured at 3 days after initiation of culture to $10^6$ cells/mL and used 24 hours later. During all incubations, the cells were kept in an atmosphere of 5% $CO_2$, 90-100% humidity, and 37° C.

A viable cell count was obtained by trypan blue exclusion and an appropriate volume of the cell suspension was placed in a polypropylene centrifuge tube. The cells were washed in DPBS and then resuspended to two-thirds the final volume needed in Dulbecco□s Modified Eagle□s Medium (DME, Sigma D5030) with the supplements listed in Table 17, as well as 2-ME, sodium pyruvate and NEAA, and including 10% HI FBS, but without glucose, L-glutamine, sodium pyruvate, and phenol red. This medium is termed DME-RTK. An aliquot was counted by trypan blue exclusion and the cell density was adjusted to $1 \times 10^6$/mL. Fifty μL of DME-RTK were added to each well of the appropriate number of half area, 96-well plates (PM1 and PM2 MICROPLATE testing plates). The cells were divided into two lots and one lot received a 1/100 dilution of 100 mM sodium pyruvate (final concentration, 0.5 mM). Cells from both lots were plated at a final cell density of $5 \times 10^4$/well (50 μL/well). For each plate containing chemicals and cells, a second, control plate containing only chemicals was prepared. Plates were incubated at 5% $CO_2$, 90-100% humidity, and 37° C. for 1 hour prior to addition of the MTS/MPMS colorimetric reagent (5 μL/well).

The color formed in each well 24 hours after addition of the colorimetric reagent, was measured with a plate reader at 490 nm with a reference wavelength of 650 nm. OD values from the control plate were subtracted from the OD values obtained with cells prior to normalizing the data to % negative control.

As shown in Table 26, TK-1 cells (mouse T-lymphoblastoid) demonstrated a different profile in PM1 and PM2 than had been seen with HL-60 (human myeloid) cells (See, Example 27). In fact, several chemicals elicited a response from one cell line but not the other, while other chemicals elicited a response from both cell lines. For PM1, there were 7 responses unique to HL-60 cells and 5 responses unique to TK-1 cells. In PM2, there were 12 responses unique to HL-60 cells and 3 responses unique to TK-1 cells. HL-60 and TK-1 responses in which a high background was observed have been excluded from this analysis, as was the response to L-arginine, since this amino acid was present in the NEAA supplement.

When sodium pyruvate, a usual component of culture medium for TK-1 cells, was added at 0.5 mM, the profile for TK-1 cells was further modified. The response in PM1 in the presence of 0.5 mM sodium pyruvate was restricted to L-glutamine, D-threonine, and succinic acid. The pattern in PM2 was more complex. In the presence of sodium pyruvate, TK-1 cells lost responses to 4 chemicals (L-ornithine, L-homoserine, glycogen, and γ-hydroxy butyric acid) and gained responses to 8 chemicals (L-phenylalanine, L-pyroglutamic acid, 4-hydroxy-benzoic acid, arbutin, sebacic acid, γ-amino butyric acid, β-methyl xyloside, and pectin). Interestingly, HL-60 cells were unable to respond to L-pyroglutamic acid and γ-amino butyric acid in the presence of added pyruvate.

TABLE 26

Comparison of the Responses of HL-60 and TK1 Cells

| Plate | +Response by HL-60 Only | +Response by TK1 Only |
|---|---|---|
| PM1 | glucose-1-phosphate | L-serine |
| | D-gluconic acid | D-threonine |
| | L-alanyl-glycine | L-threonine |
| | b-methyl glucoside | maltose |
| | pyruvic acid | D-glucuronic acid |
| | D-galacturonic acid | |
| | inosine | |
| PM2 | acetamide | L-ornithine |
| | citramalic acid | maltitol |
| | lactitol | turanose |
| | melibionic acid | |
| | L-alaninamide | |
| | L-pyroglutamic acid | |
| | L-valine | |
| | L-histidine | |
| | γ-amino-butyric acid | |
| | L-tartaric acid | |
| | 2,3 butanediol | |
| | 3-hydroxy-2-butanone | |

Example 36

Testing Tomato Cells in PM1 and PM2 Plates

In this Example, methods for testing plant cells (Blyth et al., Phytochem Anal., 12:340-346 [2001]) for their ability to use multiple carbon sources are described. Variations of these methods are within the scope of the invention and are contemplated to be suitable for efficiently testing the response of any number of agriculturally important plant cells (e.g., wheat, rice, tobacco, soy beans, etc.) to nutrients and to various chemicals, including but not limited to fertilizers, insecticides, and fungicides. However, this application is not intended to be limited to the use of tomato cells.

Briefly, callus cultures derived from leaf or stem cuttings of young tomato plants grown in MS medium containing 8 g/L bacto-agar as described (Blyth et al., Phytochem Anal., 12:340-346 [2001]). MS medium refers to Murashige and Skoog medium pH 5.8, supplemented with vitamins, 2 g/L casein, 0.25 mg/L kinetin, and 2 mg/L 2,4-dichlorophenoxy acetic acid. A cell suspension is obtained by subsequently growing the callus in MS medium in the absence of bacto-agar on a shaker in the dark at 22° C. The cells are then washed and resuspended in 0.05 M phosphate buffer (pH 7.45) and added to wells of PM1 and PM2 PHENOTYPE MICROARRAY testing panels (commercially available from Biolog). For each plate containing chemicals and cells, a second, control plate containing only chemicals and phosphate buffer is prepared. After a suitable incubation period, the cells are assayed for metabolic activity by addition of Alamar Blue or triphenyl tetrazolium chloride.

Example 37

Testing Cells in Plates Containing Carbon Sources and a Time Released Colorimetric Agent In this Example, stream-lined methods for testing the response of cells to various carbon sources, without a separate colorimetric agent addition step are described. These methods are contemplated to reduce the amount of technician time spent performing the assay, while protecting the cells from immediate exposure to potentially toxic colorimetric agents until they've had a chance to recover from the shock of subculturing.

Briefly, modified testing panels are produced by distributing and drying down a first colorimetric indicator layer (e.g., tetrazolium violet, alamar blue, redox purple, etc.), a second time release compound layer (e.g., agar, agarose, gellan gum, arabic gum, xanthan gum, carageenan, alginate salts, bentonite, ficoll, pluronic polyols, CARBOPOL, polyvinylpyrrolidone, polyvinyl alcohol, polyethylene glycol, methyl cellulose, hydroxymethyl cellulose, hydroxyethyl cellulose, carboxymethyl cellulose, carboxymethyl chitosan, chitosan, poly-2-hydroxyethyl-methacrylate, polylactic acid, polyglycolic acid, collagen, gelatin, glycinin, sodium silicate, silicone oil, silicone rubber, etc.) and a third substrate layer (e.g., carbon sources, nitrogen sources, phosphorous sources, sulfur sources, BACs, etc.). Alternatively, the colorimetric indicator may be mixed with the time release compounds prior to distribution into wells of the testing panels as a single layer. To run a test, a cell suspension is prepared and simply added to the wells of the testing panel. The cells are exposed immediately to the substrate in the top layer. Then after some period of dissolution, the colorimetric chemicals are released and thereby automatically added to the cells. For example, after an ~4-48 hour incubation period, the response of the cells to the substrates is quantified with a spectrophotometer. The new testing panels and methods described in this Example are contemplated to be more efficient and as effective for testing cells, as the methods described above having a separate, delayed colorimetric indicator addition step.

Example 38

Obtaining a Metabolic Profile of A549 Cells in the Presence of Serum

Figure 10:
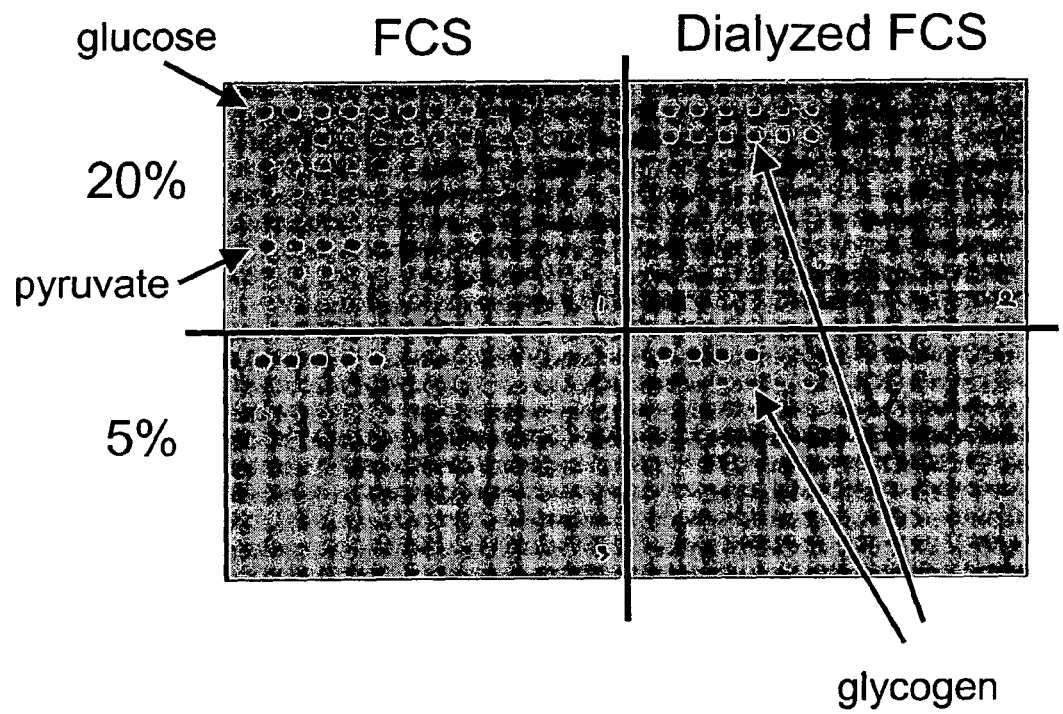
FIG. 10 provides an image of one testing device of the present invention demonstrating differential glycogen-, glucose- and pyruvate-stimulated A549 cell mediated dye reduction due to varying the concentrations of FCS (5% or 20%) and dialysis of the FCS.

Briefly, A549 cells were suspended at 400,000 cells/mL in RPMI-salts+RPMI-vitamins+1×Pen/Strep (Penicillin/Streptomycin) without amino acids but containing either 5% or 20% dialyzed or non-dialyzed FCS. Cells were dispensed in 50 uL to wells containing a plurality of testing substrates (glycogen, glucose and pyruvate among others) at final concentrations of 20, 15, 10.5, 2.5 and 1.2 mM of each testing substrate. The cells were incubated for 2 days at 37° C. under 5% $CO_2$-95% air (pre-incubation phase), before a redox dye mix was added. The cells were incubated for an additional 5 hr at 37° C. under 5% $CO_2$-95% air (incubation phase), before color development was measured. Representative results are shown in FIG. 10.

Example 39

Figure 11A:
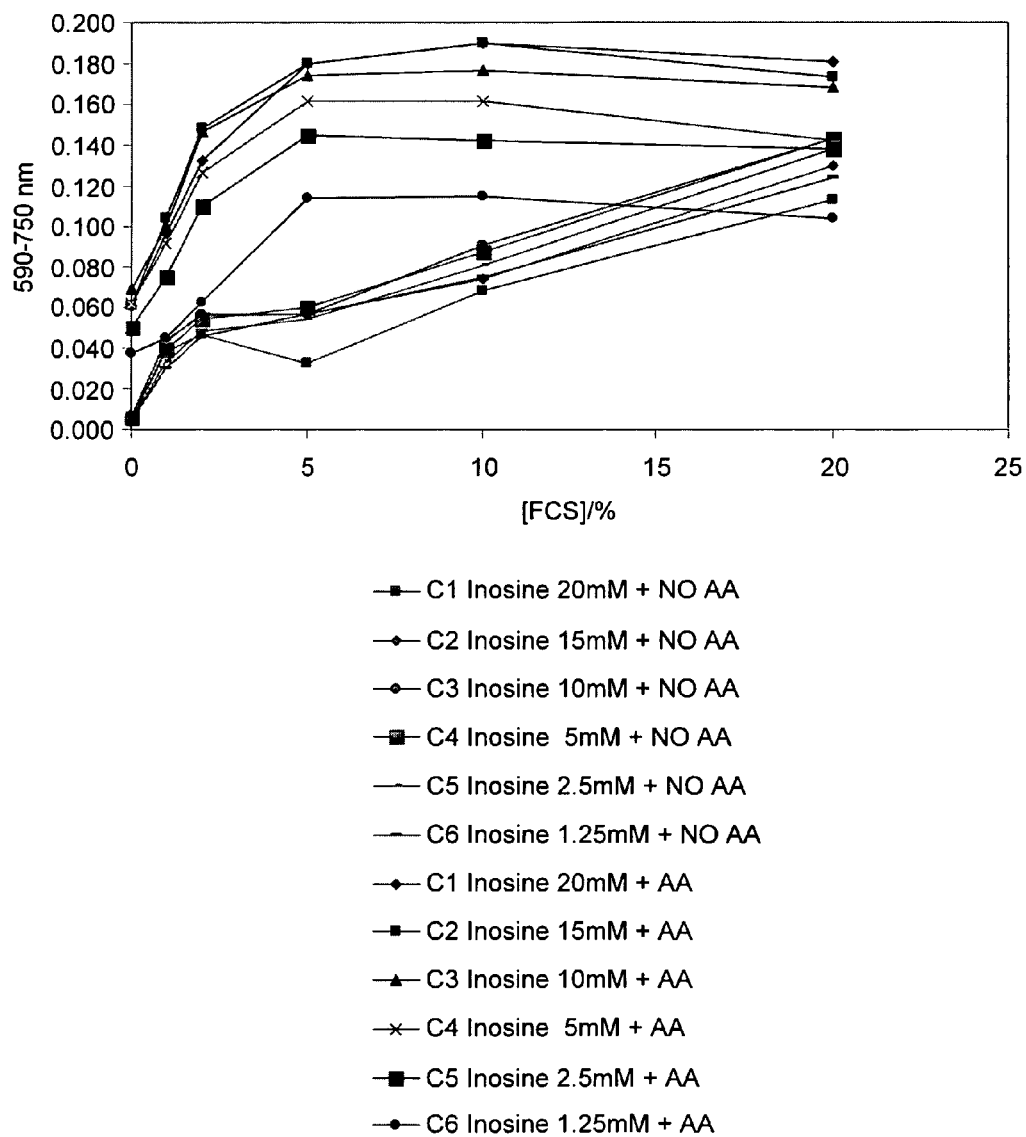
FIG. 11A provides a graph showing differential inosine-stimulated dye reduction by A549 cells at varying concentrations of FCS, in the presence and absence of free amino acids.
Figure 11B:
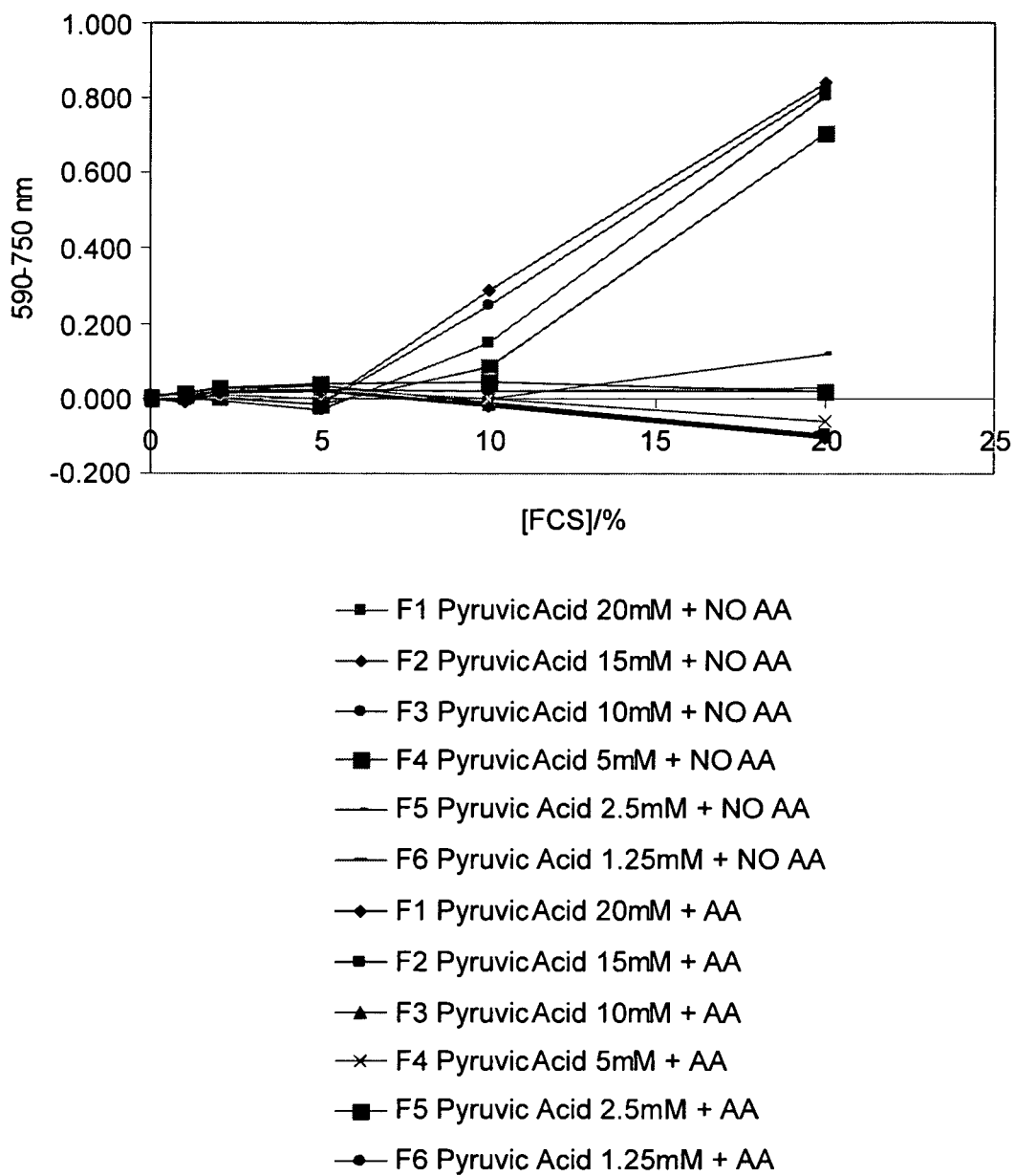
FIG. 11B provides a graph showing differential pyruvate-stimulated dye reduction by A549 cells at varying concentrations of FCS, in the presence and absence of free amino acids. These assays demonstrated that inosine is used more rapidly in the presence of amino acids and that pyruvate is used more rapidly in the absence of amino acids.

Testing Substrate Utilization by A549 Cells in the Presence of Increasing Serum Concentrations and in the Presence and Absence of Free Amino Acids Briefly, A549 cells were suspended in RPMI-salts+RPMI-vitamins+1× Pen/Strep with or without RPMI-amino acids at 400,000 cells/mL and dispensed in 50 uL to wells containing a testing substrates (e.g., inosine, pyruvic acid, glucose, L-glutamine, L-arginine, etc.) and FCS to achieve the indicated final concentrations. The cells were incubated for 2 days at 37° C. under 5% $CO_2$-95% air (pre-incubation phase), before a redox dye mix was added. The cells were incubated for an additional 5 hr at 37° C. under 5% $CO_2$-95% air (incubation phase), before color development was measured. Representative results are shown in FIGS. 11A and 11B.

Example 40

Figure 12:
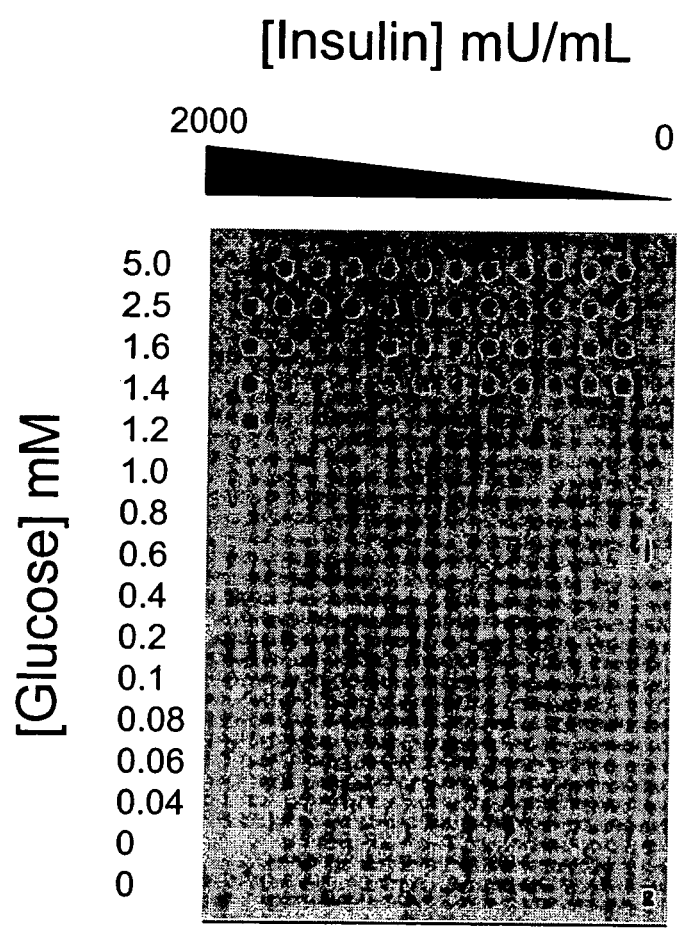
FIG. 12 provides an image of one testing device of the present invention, demonstrating insulin dependent depletion of a glucose substrate by A549 cells (in a cross titration format), as evidenced by its effect on cell-mediated dye reduction.

Testing Glucose Substrate Utilization by A549 Cells in Response to Insulin in a Cross-Titration Format Briefly, A549 cells were suspended in RPMI-salts+RPMI-vitamins+1× Pen/Strep without amino acids at 400,000 cells/mL and dispensed in 50 uL to wells containing glucose to achieve the indicated final glucose concentrations. Insulin was then added to achieve the indicated final insulin concentrations. The cells were adapted to glucose by maintaining the cells for 2 days at 37° C. under 5% $CO_2$-95% air (pre-incubation phase), before a redox dye mix was added. Color development was measured after maintaining the cells for an additional 5 hr at 37° C. under 5% $CO_2$-95% air (incubation phase). Representative results are shown in FIG. 12.

Example 41

Obtaining a Metabolic Profile of Mammalian Cells

Briefly, mammalian cells (e.g., A549—lung, C3A—liver, Colo205—colon, CEM-blood, PC-3—prostate, HepG2—liver, HL-60—leukemia, TK-1—lymphoma, etc.) are suspended at about 400,000 cells/mL in RPMI medium lacking glucose and phenol red, but containing 0.3 mM glutamine, 5% FBS and 1× Pen/Strep. Cells are dispensed in a 50 μL volume to wells of a testing device (e.g., 96-well half area microplate) containing a plurality of testing substrates (glycogen, glucose and pyruvate, among others at final concentrations of about 20 mM, although concentrations of from 1 to 20 mM are suitable). The cells are incubated for 2 days (e.g., 40 to 48 hours) at 37° C. under 5% $CO_2$-95% air (pre-incubation phase). A suitable redox dye mix, such as Dye Mix MC-X (Biolog#74320) is then added. In exemplary embodiments, a working solution of Dye Mix MC-X is made by adding one volume Dye Mix MC-X to three volumes of an appropriate diluent (e.g., PBS), which is dispensed in a 10 μL volume to wells of the testing device. The cells are incubated for an additional 5 hr at 37° C. under 5% $CO_2$-95% air (incubation phase), before color development is measured. Although employed in some embodiments, high $CO_2$ is not required by the methods of the present invention.

Other suitable dye mixes for use with the present invention include but are not limited to dyes mixes such as Redox Dye Mix MA (Biolog #74351) and Redox Dye Mix MB (Biolog #74352), which contain a tetrazolium-based reagent that can be reduced to a soluble purple formazan product by living cells when used according to the manufacturer's instructions. This differs from MTT, which precipitates inside cells requiring a solubilization step with an organic compound before it can be measured. The Biolog dye mixes experience low abiotic reduction levels yielding high signal to noise background ratios for improved assay sensitivity. In fact, the Biolog dye mixes when used with the methods of the present invention can permit the enumeration of cells at concentrations ranging from 300 cells/well to 160,000 cells/well. Although both Biolog dye mixes can be used with a wide range of cell types, superior results are frequently achieved with a specific cell/dye mix combination, which is empirically determined. For instance during development of the present invention, good results were obtained when testing HepG2, C3A, PC-3, Colo205 and A259 with Redox Dye Mix MA (after a 1-6 hr color development step), and when testing CEM, HL-60, and IMR-90 cells with Redox Dye Mix MB (after a 1-24 hr color development step). Tetrazolium reduction can be quantified kinetically or at a fixed time point by measuring absorbance at 590 nm. However, in preferred embodiments, tetrazolium reduction is quantified in a dual wavelength mode (590 nm with a reference wavelength at 750 nm).

From the above examples, it is clear that the present invention represents an unexpected and much improved system for the broad-based, rapid biochemical testing and/or phenotypic testing of microorganisms, cell lines, and/or other cell types, in many uses and formats (or configurations), as well as for drug development and research. In addition, both automated and manual systems with fixed time point or kinetic readings may be used in conjunction with the present invention. For example, the results may be observed visually (i.e., by eye) by the person conducting the test, without assistance from a machine. Alternatively, the results may be obtained with the use of equipment (e.g., a microtiter plate reader) that measures transmittance, absorbance, or reflectance through, in, or from each well of a multitest device such as a microtiter testing plate (e.g., MICROPLATE testing plates) or a miniaturized testing card (e.g., MICROCARD miniaturized testing cards). Kinetic readings may be obtained by taking readings at frequent time intervals or reading the test results continuously over time. One example of a device particularly suited for incubating and conducting the methods of the present invention includes the device described in U.S. Pat. No. 6,271,022, hereby incorporated by reference.

All references, including publications, patent applications, and patents, cited herein are hereby incorporated by reference to the same extent as if each reference were individually and specifically indicated to be incorporated by reference and were set forth in its entirety herein (to the maximum extent permitted by law). All headings and sub-headings are used herein for convenience only and should not be construed as limiting the invention in any way. Any combination of the above-described elements in all possible variations thereof is encompassed by the invention unless otherwise indicated herein or otherwise clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents. A description herein of an aspect or embodiment of the invention using terms such as "comprising", "having," "including," or "containing" a particular element is intended to provide support for an aspect or embodiment of the invention that "consists of", "consists essentially of", or "substantially comprises" that particular element, unless otherwise stated or clearly contradicted by context. This invention includes all modifications and equivalents of the subject matter recited in the claims appended hereto as permitted by applicable law.

The invention claimed is:

1. A method for phenotyping animal cells, comprising the steps of:
   a) providing:
      i) a suspension medium comprising at least one animal cell;
      ii) a testing device comprising a positive control well, a negative control well and a plurality of testing wells wherein each of said plurality of testing wells and said positive control well contain at least one testing substrate; and
      iv) a redox indicator;
   b) introducing a first portion of said suspension medium into said positive control well and said negative control well and incubating said positive control well and said negative control well;
   c) introducing a first portion of said redox indicator into said positive control well and said negative control well, wherein an adaptation period length is determined by greater measurable color developed in said positive control well as compared to measurable color developed in said negative control well;
   d) introducing a second portion of said suspension medium into said plurality of testing wells;
   e) pre-incubating said second portion of said suspension medium in said plurality of testing wells for said adaptation period length;
   f) introducing a second portion of said redox indicator into said plurality of testing wells;
   g) incubating said second portion of said suspension medium such that said redox indicator is reduced in at least one testing substrate well to produce a color development;
   h) measuring said color development in said plurality of testing wells to create a metabolic profile; and
   i) analyzing said metabolic profile to determine phenotypes of said at least one animal cell.

2. The method of claim 1, wherein said adaptation period length is determined by a greatest difference in measurable color between said positive control well and said negative control well.

3. The method of claim 1, wherein said plurality of testing substrates comprises at least 24 testing substrates.

4. The method of claim 1, wherein said plurality of testing substrates comprises three or more of alpha-Cyclodextrin, Sodium Hexanoate, Dextrin, Tween 20, Glycogen, Tween 40, Maltitol, Tween 80, Maltotriose, Gelatin, D-(+)-Maltose, Sodium 4-Hydroxybenzoate, D-Trehalose, 4-Hydroxyphenylacetic acid, D-(+) Cellobiose, (±)-Octopamine, beta-Gentiobiose, 2-Phenylethylamine, L-Glucose, Tryptamine, D-(+)-Glucose, Tyramine, Cys-Gly, Phe-Ala, Gly-Cys, Phe-Asp, Gly-Ala, Phe-Glu, Gly-Arg, Phe-Gly, Gly-Asn, Phe-Ile, Gly-Asp, Phe-Met, Gly-Gly, Phe-Phe, Gly-His, Phe-Pro, Gly-Ile, Phe-Ser, Gly-Leu, Phe-Trp, Gly-Lys·HCl, Phe-Tyr, D-Glucose-6-phosphate, L-Alaninamide, alpha-D-Glucose 1-phosphate, L-Alanine, 3-O-Methyl-D-glucopyranose, D-Alanine, Methyl alpha-D-glucoside, L-Arginine, Methyl beta-D-glucoside, L-Asparagine, D-(−)-Salicin, L-Aspartic acid, D-Sorbitol, D-Aspartic Acid, N-Acetyl-D-glucosaminitol, L-Glutamic acid hydrate, N-Acetyl-D-glucosamine, D-Glutamic Acid, D-(+)-Glucosamine, L-Glutamine, D-Glucosaminic acid, Glycine, D-Gluconic acid, L-Histidine, Gly-Met, Phe-Val, Gly-Phe, Pro-Ala, Gly-Pro, Pro-Arg, Gly-Ser, Pro-Asn, Gly-Thr, Pro-Asp, Gly-Trp, Pro-Glu, Gly-Tyr, Pro-Gln, Gly-Val, Pro-Gly, His-Ala, Pro-Hyp, His-Asp, Pro-Ile , His-Glu, Pro-Leu, His-Gly, Pro-Lys, D-Glucuronic acid , L-Homoserine, Chondroitin 6-sulfate, trans-4-Hydroxy-L-Proline, Mannan, L-Isoleucine, D-Mannose, L-Leucine, Methyl alpha-D-Mannopyranoside, L-Lysine, D-Mannitol, L-Methionine, N-Acetyl-D-mannosamine, L-Ornithine, D-(+)-Melezitose monohydrate, L-Phenylalanine, Sucrose, L-Proline, Palatinose, L-Serine, D-(+)-Turanose, D-Serine, D-Tagatose, L-Threonine, His-His, Pro-Phe, His-Leu, Pro-Pro, HCl, His-Lys.HBr, Pro-Ser, His-Met, Pro-Trp, His-Pro, Pro-Tyr, His-Ser, Pro-Val, His-Trp, Ser-Ala, His-Tyr, Ser-Asn, His-Val, Ser-Asp, Ile-Ala, Ser-Glu, Ile-Arg, Ser-Gln, Ile-Asn, Ser-Gly, L-(−)-Sorbose, D-Threonine, L-Rhamnose, L-Tryptophan, L-Fucose, L-Tyrosine, D-Fucose, L-Valine, Fructose, Ala-Ala, D-Fructose-6-phosphate, Ala-Arg, Stachyose, Ala-Asn, D-Raffinose, Ala-Asp, D-Lactitol, Ala-Glu, Lactulose, Ala-Gln, Lactose, Ala-Gly, Melibionic Acid, Ala-His, Ile-Gln, Ser-His, Ile-Gly, Ser-Leu, Ile-His, Ser-Met, Ile-Ile, Ser-Phe, Ile Leu Ser-Pro, Ile-Met, Ser-Ser, Ile-Phe, Ser-Tyr, Ile-Pro, Ser-Val, Ile-Ser, Thr-Ala, Ile-Trp, Thr-Arg, Ile-Tyr, Thr-Asp, Ile-Val, Thr-Glu, D-Melibiose, Ala-Ile, D-Galactose, Ala-Leu, Methyl alpha-D-galactopyranoside, Ala-Lys·HCl, Methyl-beta-D-galactopyranoside, Ala-Met, N-Acetyl-neuraminic acid, Ala-Phe, Pectin, Ala-Pro, Sedoheptulose anhydride monohydrate, Ala-Ser, Thymidine, Ala-Thr, Uridine, Ala-Trp, Adenosine, Ala-Tyr, Inosine, Ala-Val, D-Ribose, Arg-Ala, Leu-Ala, Thr-Gln, Leu-Arg, Thr-Gly, Leu-Asn, Thr-Leu, Leu-Asp, Thr-Met, Leu-Glu, Thr-Phe, Leu-Gly, Thr-Pro, HCl, Leu-His, Thr-Ser, Leu-Ile, Trp-Ala, Leu-Len, Trp-Arg·, Leu-Met, Trp-Asp, Leu-Phe, Trp-Glu, Leu-Pro,-HCl, Trp-Gly, Ribitol, Arg-Arg, L-Arabinose, Arg-Asp, D-Arabinose, Arg-Gln, D-Xylose, Arg-Glu, Methyl beta-D-Xylopyranoside, Arg-Ile, Xylitol, Arg-Leu, myo-Inositol, Arg-Lys, meso-Erythritol, Arg-Met, Propylene glycol, Arg-Phe, Ethanolamine, Arg-Ser, Glycerol, Arg-Trp, rac-Glycerol 3-phosphate, Arg-Tyr, Leu-Ser, Trp-Leu, Leu-Trp, Trp-Lys, Leu-Tyr, Trp-Phe, Leu-Val, Trp-Ser, Lys-Ala, Trp-Trp, Lys-Arg, Trp-Tyr, Lys-Asp, Trp-Val, Lys-Glu, Tyr-Ala, Lys-Gly.HCl, Tyr-Gln, Lys-Ile, Tyr-Glu, Lys-Leu, Tyr-Gly, Lys-Lys·2 HCl, Tyr-His, Citric acid, Arg-Val, Tricarballylic Acid, Asn-Glu, Sodium Lactate, Asn-Val, Methyl D-lactate, Asp-Ala, Methyl pyruvate, Asp-Asp, Pyruvate, Asp-Gin, 2-Oxoglutarate, Asp-Gln, Succinamic acid, Asp-Gly, Succinate, Asp-Leu, mono-Methyl hydrogen succinate, Asp-Lys, L-(−)-Malic acid, Asp-Phe, D-(+)-Malic acid, Asp-Trp, Lys-Met, Tyr-Ile, Lys-Phe.HCl, Tyr-Leu, Lys-Pro, Tyr-Lys, Lys-Ser, Tyr-Phe, Lys-Thr, Tyr-Trp, Lys-Trp, Tyr-Tyr, Lys-Tyr, Tyr-Val, Lys-Val, Val-Ala, Met-Arg, Val-Arg, Met-Asp, Val-Asn, Met-Gln, Val-Asp, Met-Glu, Val-Glu, meso-Tartaric acid, Asp-Val, Acetoacetate, Glu-Ala, gamma-Amino-N-butyric acid, Glu-Asp, Sodium 2-Oxobutyrate, Glu-Glu, Sodium 2-Hydroxybutyrate , Glu-Gly, DL-beta-Hydroxybutyric acid, Glu-Ser, 4-Hydroxybutyric acid, Glu-Trp, Sodium Butyrate, Glu-Tyr, 2,3-Butanediol, Glu-Val, 3-Hydroxy 2-Butanone, Gln-Glu, Propionic acid, Gln-Gln, Sodium Acetate, Gln-Gly, Met-Gly, Val-Gln, Met-His, Val-Gly, Met-Ile, Val-His, Met-Len, Val-Ile, Met-Lys, Val-Leu.HCl, Met-Met, Val-Lys, Met-Phe, Val-Met, Met-Pro, HCl, Val-Phe, Met-Thr, Val-Pro, Met-Trp, Val-Ser, Met-Tyr, Val-Tyr, Met-Val, and Val-Val.

5. The method of claim 1, wherein said suspension medium comprises 10,000 to 800,000 cells/ml.

6. The method of claim 1, wherein said suspension medium comprises vitamins, salts, and free amino acids and is in the absence of D-glucose, sodium pyruvate, and phenol red, wherein each of said free amino acids is at a concentration of less than 1.2 mM.

7. The method of claim 1, wherein a serum supplement is provided to said suspension medium.

8. The method of claim 7, wherein said serum is dialyzed.

9. The method of claim 1, wherein said pre-incubating of said suspension medium in step e) is for a period of 12 to 60 hours.

10. The method of claim 1, wherein said incubating of said suspension medium in step g) is for a period of 0.5 to 36 hours.

11. A method for observing effects of a candidate compound on substrate utilization by animal cells, comprising the steps of:
a) providing:
i) a suspension medium comprising at least one animal cell;
ii) one or more testing devices comprising a positive control well and a negative control well;
iii) said one or more testing devices further comprising a plurality of testing wells and wherein each of said plurality of testing wells comprises a plurality of the same testing substrates wherein each of said plurality of testing wells and said positive control well contain at least one testing substrate; and
iv) a redox indicator;
b) introducing a first portion of said suspension medium into said positive control well and said negative control well and incubating said positive control well and said negative control well;
c) introducing a first portion of said redox indicator into said positive control well and said negative control well wherein an adaptation period length is determined by a greater measurable color developed in said positive control well as compared to measureable color developed in said negative control well;
d) introducing a second portion of said suspension medium into said plurality of testing wells;
e) introducing a candidate compound at a range of concentrations into said plurality of testing wells;
f) pre-incubating said second portion of said suspension medium in said plurality of testing wells for said adaptation period length;
g) introducing a second portion of said redox indicator into said plurality of testing wells;
h) incubating said second portion of said suspension medium with said second portion of said redox indicator wherein a color development occurs in at least one of said plurality of testing wells;
i) measuring said color development to obtain a metabolic profile of said second portion of said suspension medium, wherein said color development is selected from the group consisting of increased color development and decreased color development; and
j) analyzing said metabolic profile to determine phenotypes of said animal cells wherein an utilization effect of said candidate compound is identified based on said testing substrates.

12. The method of claim 11, wherein said adaptation period length is determined by a greatest difference in measurable color between said positive control well and said negative control well.

13. The method of claim 11, wherein said effect of said candidate compound increases substrate utilization by said second portion of said suspension medium.

14. The method of claim 11, wherein said effect of said candidate compound decreases substrate utilization by said second portion of said suspension medium.

15. The method of claim 11, wherein said plurality of testing substraes comprises at least 24 testing substrates.

16. The method of claim 11, wherein said plurality of testing substrates comprises three or more of alpha-Cyclodextrin, Sodium Hexanoate, Dextrin, Tween 20, Glycogen, Tween 40, Maltitol, Tween 80, Maltotriose, Gelatin, D-(+)-Maltose, Sodium 4-Hydroxybenzoate, Trehalose, 4-Hydroxyphenylacetic acid, D-(+) Cellobiose, (±)-Octopamine, beta-Gentiobiose, 2-Phenylethylamine, L-Glucose, Tryptamine, D-(+)-Glucose, Tyramine, Cys-Gly, Phe-Ala, Gly-Cys, Phe-Asp, Gly-Ala, Phe-Glu, Gly-Arg, Phe-Gly, Gly-Asn, Phe-Ile, Gly-Asp, Phe-Met, Gly-Gly, Phe-Phe, Gly-His, Phe-Pro, Gly-Ile, Phe-Ser, Gly-Leu, Phe-Trp, Gly-Lys·HCl, Phe-Tyr, D-Glucose-6-phosphate, L-Alaninamide, alpha-D-Glucose 1-phosphate, L-Alanine, 3-O-Methyl-D-glucopyranose, D-Alanine, Methyl alpha-D-glucoside, L-Arginine, Methyl beta-D-glucoside, L-Asparagine, D-(−)-Salicin, L-Aspartic acid, D-Sorbitol, D-Aspartic Acid, N-Acetyl-D-glucosaminitol, L-Glutamic acid hydrate, N-Acetyl-D-glucosamine, D-Glutamic Acid, D-(+)-Glucosamine, L-Glutamine, D-Glucosaminic acid, Glycine, D-Gluconic acid, L-Histidine, Gly-Met, Phe-Val, Gly-Phe, Pro-Ala, Gly-Pro, Pro-Arg, Gly-Ser, Pro-Asn, Gly-Thr, Pro-Asp, Gly-Trp, Pro-Glu, Gly-Tyr, Pro-Gln, Gly-Val, Pro-Gly, His-Ala, Pro-Hyp, His-Asp, Pro-Ile , His-Glu, Pro-Leu, His-Gly, Pro-Lys, D-Glucuronic acid , L-Homoserine, Chondroitin 6-sulfate, trans-4-Hydroxy-L-Proline, Mannan, L-Isoleucine, D-Mannose, L-Leucine, Methyl alpha-D-Mannopyranoside, L-Lysine, D-Mannitol, L-Methionine, N-Acetyl-D-mannosamine, L-Ornithine, D-(+)-Melezitose monohydrate, L-Phenylalanine, Sucrose, L-Proline, Palatinose, L-Serine, D-(+)-Turanose, D-Serine, D-Tagatose, L-Threonine, His-His, Pro-Phe, His-Leu, Pro- Pro, HCl, His-Lys·HBr, Pro-Ser, His-Met, Pro-Trp, His-Pro, Pro-Tyr, His-Ser, Pro-Val, His-Trp, Ser-Ala, His-Tyr, Ser-Asn, His-Val, Ser-Asp, Ile-Ala, Ser-Glu, Ile-Arg, Ser-Gln, Ile-Asn, Ser-Gly, L-(−)-Sorbose, D-Threonine, L-Rhamnose, L-Tryptophan, L-Fucose, L-Tyrosine, D-Fucose, L-Valine, Fructose, Ala-Ala, D-Fructose 6-phosphate, Ala-Arg, Stachyose, Ala-Asn, D-(+)-Raffinose, Ala-Asp, D-Lactitol, Ala-Glu, Lactulose, Ala-Gln, Lactose, Ala-Gly, Melibionic Acid, Ala-His, Ile-Gln, Ser-His, Ile-Gly, Ser-Leu, Ile-His, Ser-Met, Ile-Ile, Ser-Phe, Ile-Leu, Ser-Pro, Ile-Met, Ser-Ser, Ile-Phe, Ser-Tyr, Ile-Pro, Ser-Val, Ile-Ser, Thr-Ala, Ile-Trp, Thr-Arg, Ile-Tyr, Thr-Asp, Ile-Val, Thr-Glu, D-Melibiose, Ala-Ile, D-Galactose, Ala-Leu, Methyl alpha-D-galactopyranoside, Ala-Lys.HCl, Methyl-beta-D-galactopyranoside, Ala-Met, N-Acetyl-neuraminic acid, Ala-Phe, Pectin, Ala-Pro, Sedoheptulose anhydride monohydrate, Ala-Ser, Thymidine, Ala-Thr, Uridine, Ala-Trp, Adenosine, Ala-Tyr, Inosine, Ala-Val, D-Ribose, Arg-Ala, Leu-Ala, Thr-Gln, Leu-Arg, Thr-Gly, Leu-Asn, Thr-Leu, Leu-Asp, Thr-Met, Leu-Glu, Thr-Phe, Leu-Gly, Thr-Pro, HCl, Len-His, Thr-Ser, Leu-Ile, Trp-Ala, Leu-Leu, Trp-Arg·, Leu-Met, Trp-Asp, Leu-Phe, Trp-Glu, Leu-Pro·HCl, Trp-Gly, Ribitol, Arg-Arg, L-Arabinose, Arg-Asp, D-Arabinose, Arg-Gln, D-Xylose, Arg-Glu, Methyl beta-D-Xylopyranoside, Arg-Ile, Xylitol, Arg-Leu, myo-Inositol, Arg-Lys, meso-Erythritol, Arg-Met, Propylene glycol, Arg-Phe, Ethanolamine, Arg-Ser, Glycerol, Arg-Trp, rac-Glycerol 3-phosphate, Arg-Tyr, Leu-Ser, Trp-Leu, Leu-Trp, Trp-Lys, Leu-Tyr, Trp-Phe, Leu-Val, Trp-Ser, Lys-Ala, Trp-Trp, Lys-Arg, Trp-Tyr, Lys-Asp, Trp-Val, Lys-Glu, Tyr-Ala, Lys-Gly.HCl, Tyr-Gln, Lys-Ile, Tyr-Glu, Lys-Leu, Tyr-Gly, Lys-Lys.2HCl, Tyr-His, Citric acid, Arg-Val, Tricarballylic Acid, Asn-Glu, Sodium Lactate, Asn-Val, Methyl D-lactate, Asp-Ala, Methyl pyruvate, Asp-Asp, Pyruvate, Asp-Glu, 2-Oxoglutarate, Asp-Gln, Succinamic acid, Asp-Gly, Succinate, Asp-Leu, mono-Methyl hydrogen succinate, Asp-Lys, L-(−)-Malic acid, Asp-Phe, D-(+)-Malic acid, Asp-Trp, Lys-Met, Tyr-Ile, Lys-Phe·HCl, Tyr-Leu, Lys-Pro, Tyr-Lys, Lys-Ser, Tyr-Phe, Lys-Thr, Tyr-Trp, Lys-Trp, Tyr-Tyr, Lys-Tyr, Tyr-Val, Lys-Val, Val-Ala, Met-Arg, Val-Arg, Met-Asp, Val-Asn, Met-Gln, Val-Asp, Met-Glu, Val-Glu, meso-Tartaric acid, Asp-Val, Acetoacetate, Glu-Ala, gamma-Amino-N-butyric acid, Glu-Asp, Sodium 2-Oxobutyrate, Glu-Glu, Sodium 2-hydroxybutyrate, Glu-Gly, DL-beta-Hydroxybutyric acid, Glu-Ser, 4-Hydroxybutyric acid, Glu-Trp, Sodium Butyrate, Glu-Tyr, 2,3-Butanediol, Glu-Val, 3-Hydroxy 2-Butanone, Gln-Glu, Propionic acid, Gln-Gln, Sodium Acetate, Gln-Gly, Met-Gly, Val-Gln, Met-His, Val-Gly, Met-Ile, Val-His, Met-Leu, Val-Ile, Met-Lys, Val-Leu·HCl, Met-Met, Val-Lys, Met-Phe, Val-Met, Met-Pro, HCl, Val-Phe, Met-Thr, Val-Pro, Met-Trp, Val-Ser, Met-Tyr, Val-Tyr, Met-Val, and Val-Val.

17. The method of claim 11, wherein said suspension medium comprises 10,000 to 800,000 cells/ml.

18. The method of claim 11, wherein said suspension medium comprises vitamins, salts, and free amino acids, and is in the absence of D-glucose, sodium pyruvate, and phenol red, wherein each of said free amino acids is at a concentration of less than 1.2 mM.

19. The method of claim 11, wherein a scrum supplement is provided to said suspension medium.

20. The method of claim 19, wherein said serum is dialyzed.

21. The method of claim 11, wherein said pre-incubating of said suspension medium in step f) is for a period of 12 to 60 hours.

22. The method of claim 11, wherein said incubating of said suspension medium in step h) is for a period of 0.5 to 36 hours.

23. A method for phenotyping a multiplexed metabolic profile of animal cells, comprising the steps of:
  a) providing a testing device comprising a plurality of testing wells and a plurality of testing substrates, wherein each of said testing wells contains at least one unique testing substrate;
  b) suspending multiple samples comprising animal cells in multiple suspension media to produce multiple suspensions, wherein said multiple suspension media are selected from the group consisting of three or more of a low serum medium, an intermediate serum medium, a high serum medium, a whole serum medium, a dialyzed serum medium, an amino acid-rich medium, and an amino acid poor-medium, wherein said multiple suspension media are aqueous solutions comprising extraneous substrates;
  c) introducing said multiple suspensions of animal cells into said testing wells of said testing device;
  d) pre-incubating said animal cells in said testing device wherein said extraneous substrates are depleted;
  e) introducing a redox indicator into said plurality of testing wells that have been depleted of said extraneous substrates in step d) of said testing device;
  f) incubating said animal cells in said testing device wherein a color development occurs in at least one of said each of said plurality of testing wells primarily due to utilization of said at least one unique testing substrate;
  g) measuring said color development to obtain a multiplexed metabolic profile of said animal cells, comprising multiple metabolic profiles; and
  h) analyzing said multiple metabolic profiles to determine phenotypes of said animal cells.

24. The method of claim 15, wherein said plurality of testing substrates comprises at least 24 testing substrates.

25. The method of claim 15, wherein said plurality of testing substrates comprises three or more of alpha-Cyclodextrin, Sodium Hexanoate, Dextrin, Tween 20, Glycogen, Tween 40, Maltitol, Tween 80, Maltotriose, Gelatin, D-(+)-Maltose, Sodium 4-Hydroxybenzoate, Trehalose, 4-Hydroxyphenylacetic acid, D-(+) Cellobiose, (±)-Octopamine, beta-Gentiobiose, 2-Phenylethylamine, L-Glucose, Tryptamine, D-(+)-Glucose, Tyramine, Cys-Gly, Phe-Ala, Gly-Cys, Phe-Asp, Gly-Ala, Phe-Glu, Gly-Arg, Phe-Gly, Gly-Asn, Phe-Ile, Gly-Asp, Phe-Met, Gly-Gly, Phe-Phe, Gly-His, Phe-Pro, Gly-Ile, Phe-Ser, Gly-Leu, Phe-Trp, Gly-Lys·HCl, Phe-Tyr, D-Glucose-6-phosphate, L-Alaninamide, alpha-D-Glucose 1-phosphate, L-Alanine, 3-O-Methyl-D-glucopyranose, D-Alanine, Methyl alpha-D-glucoside, L-Arginine, Methyl beta-D-glucoside, L-Asparagine, D-(−)-Salicin, L-Aspartic acid, D-Sorbitol, D-Aspartic Acid, N-Acetyl-D-glucosaminitol, L-Glutamic acid hydrate, N-Acetyl-D-glucosamine, D-Glutamic Acid, D-(+)-Glucosamine, L-Glutamine, D-Glucosaminic acid, Glycine, D-Gluconic acid, L-Histidine, Gly-Met, Phe-Val, Gly-Phe, Pro-Ala, Gly-Pro, Pro-Arg, Gly-Ser, Pro-Asn, Gly-Thr, Pro-Asp, Gly-Trp, Pro-Glu, Gly-Tyr, Pro-Gln, Gly-Val, Pro-Gly, His-Ala, Pro-Hyp, His-Asp, Pro-Ile , Pro-Leu, His-Gly, Pro-Lys, D-Glucuronic acid , L-Homoserine, Chondroitin 6-sulfate, trans-4-Hydroxy-L-Proline, Mannan, L-Isoleucine, D-Mannose, L-Leucine, Methyl alpha-D-Mannopyranoside, L-Lysine, D-Mannitol, L-Methionine, N-Acetyl-D-mannosamine, L-Ornithine, D-(+)-Melezitose monohydrate, L-Phenylalanine, Sucrose, L-Proline, Palatinose, L-Serine, D-(+)-Turanose, D-Serine, D-Tagatose, L-Threonine, His-His, Pro-Phe, His-Leu, Pro- Pro, HCl, His-Lys·HBr, Pro-Ser, His-Met, Pro-Trp, His-Pro, Pro-Tyr, His-Ser, Pro-Val, His-Trp, Ser-Ala, His-Tyr, Ser-Asn, His-Val, Ser-Asp, Ile-Ala, Ser-Glu, Ile-Arg, Ser-Gln, Ile-Asn, Ser-Gly, L-(−)-Sorbose, D-Threonine, L-Rhamnose, L-Tryptophan, L-Fucose, L-Tyrosine, D-Fucose, L-Valine, Fructose, Ala-Ala, D-Fructose 6-phosphate, Ala-Arg, Stachyose, Ala-Asn, D-(+)-Raffinose, Ala-Asp, D-Lactitol, Ala-Glu, Lactulose, Ala-Gln, Lactose, Ala-Gly, Melibionic Acid, Ala-His, Ile-Gln, Ser-His, Ile-Gly, Ser-Leu, Ile-His, Ser-Met, Ile-Ile, Ser-Phe, Ile-Leu, Ser-Pro, Ile-Met, Ser-Ser, Ile-Phe, Ser-Tyr, Ile-Pro, Ser-Val, Ile-Ser, Thr-Ala, Ile-Trp, Thr-Arg, Ile-Tyr, Thr-Asp, Ile-Val, Thr-Glu, D-Melibiose, Ala-Ile, D-Galactose, Ala-Leu, Methyl alpha-D-galactopyranoside, Ala Lys.HCl, Methyl-beta-D-galactopyranoside, Ala-Met, N-Acetyl-neuraminic acid, Ala-Phe, Pectin, Ala-Pro, Sedoheptulose anhydride monohydrate, Ala-Ser, Thymidine, Ala-Thr, Uridine, Ala-Trp, Adenosine, Ala-Tyr, Inosine, Ala-Val, D-Ribose, Arg-Ala, Leu-Ala, Thr-Gln, Leu-Arg, Thr-Gly, Leu-Asn, Thr-Leu, Leu-Asp, Thr-Met, Leu-Glu, Thr-Phe, Leu-Gly, Thr-Pro, HCl, Leu-His, Thr-Ser, Leu-Ile, Trp-Ala, Leu-Leu, Trp-Arg·, Leu-Met, Trp-Asp, Leu-Phe, Trp-Glu, Leu-Pro·HCl, Trp-Gly, Ribitol, Arg-Arg, L-Arabinose, Arg-Asp, D-Arabinose, Arg-Gln, D-Xylose, Arg-Glu, Methyl beta-D-Xylopyranoside, Arg-Ile, Xylitol, Arg-Leu, myo-Inositol, Arg-Lys, meso-Erythritol, Arg-Met, Propylene glycol, Arg-Phe, Ethanolamine, Arg-Ser, Glycerol, Arg-Trp, rac-Glycerol 3-phosphate, Arg-Tyr, Leu-Ser, Trp-Leu, Leu-Trp, Trp-Lys, Leu-Tyr, Trp-Phe, Leu-Val, Trp-Ser, Lys-Ala, Trp-Trp, Lys-Arg, Trp-Tyr, Lys-Asp, Trp-Val, Lys-Glu, Tyr-Ala, Lys-Gly.HCl, Tyr-Gln, Lys-Ile, Tyr-Glu, Lys-Leu, Tyr-Gly, Lys-Lys.2 HCl, Tyr-His, Citric acid, Arg-Val, Tricarballylic Acid, Asn-Glu, Sodium Lactate, Asn-Val, Methyl D-lactate, Asp-Ala, Methyl pyruvate, Asp-Asp, Pyruvate, Asp-Glu, 2-Oxoglutarate, Asp-Gln, Succinamic acid, Asp-Gly, Succinate, Asp-Leu, mono-Methyl hydrogen succinate, Asp-Lys, L-(−)-Malic acid, Asp-Phe, D-(+)-Malic acid, Asp-Trp, Lys-Met, Tyr-Ile, Lys-Phe·HCl, Tyr-Leu, Lys-Pro, Tyr-Lys, Lys-Ser, Tyr-Phe, Lys-Thr, Tyr-Trp, Lys-Trp, Tyr-Tyr, Lys-Tyr, Tyr-Val, Lys-Val, Val-Ala, Met-Arg, Val-Arg, Met-Asp, Val-Asn, Met-Gln, Val-Asp, Met-Glu, Val-Glu, meso-Tartaric acid, Asp-Val, Acetoacetate, Glu-Ala, gamma-Amino-N-butyric acid, Glu-Asp, Sodium 2-Oxobutyrate, Glu-Glu, Sodium 2-Hydroxybutyrate, Glu-Gly, DL-beta-Hydroxybutyric acid, Glu-Ser, 4-Hydroxybutyric acid, Glu-Trp, Sodium Butyrate, Glu-Tyr, 2,3-Butanediol, Glu-Val, 3-Hydroxy 2-Butanone, Gln-Glu, Propionic acid, Gln-Gln, Sodium Acetate, Gln-Gly, Met-Gly, Val-Gln, Met-His, Val-Gly, Met-Ile, Val-His, Met-Leu, Val-Ile, Met-Lys, Val-Leu·HCl, Met-Met, Val-Lys, Met-Phe, Val-Met, Met-Pro, HCl, Val-Phe, Met-Thr, Val-Pro, Met-Trp, Val-Ser, Met-Tyr, Val-Tyr, Met-Val, and Val-Val.

26. The method of claim 15, wherein said suspension medium comprises 10,000 to 800,000 animal cells/ml.

27. The method of claim 15, wherein said suspension media comprise vitamins, salts, and free amino acids, in the absence of D-glucose, sodium pyruvate, and phenol red, wherein said free amino acids are at a concentration of less than 1.2 mM.

28. The method of claim 15, wherein a serum supplement is provided to said suspension media.

29. The method of claim 28, wherein said serum is dialyzed.

30. The method of claim 23, wherein said step d) comprises pre-incubating said suspension medium for a method of 12 to 60 hours.

31. The method of claim 23, wherein said step f) comprises incubating said suspension medium for a period of 0.5 to 36 hours.

* * * * *